US008552183B2

(12) United States Patent
Wiessler et al.

(10) Patent No.: US 8,552,183 B2
(45) Date of Patent: Oct. 8, 2013

(54) PROCESS FOR THE COVALENT COUPLING OF TWO MOLECULES BY MEANS OF A DIELS-ALDER REACTION WITH INVERSE ELECTRON REQUIREMENT

(75) Inventors: Manfred Wiessler, Frankenthal (DE); Eduard Müller, Schwetzingen (DE); Peter Lorenz, Dossenheim (DE); Christian Kliem, Heppenheim (DE); Heinz Fleischhacker, Dossenheim (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 463 days.

(21) Appl. No.: 12/304,982

(22) PCT Filed: Jun. 18, 2007

(86) PCT No.: PCT/EP2007/005361
§ 371 (c)(1),
(2), (4) Date: Apr. 21, 2009

(87) PCT Pub. No.: WO2007/144200
PCT Pub. Date: Dec. 21, 2007

(65) Prior Publication Data
US 2010/0016545 A1    Jan. 21, 2010

(30) Foreign Application Priority Data
Jun. 16, 2006    (EP) .................... 06012414

(51) Int. Cl.
*C07D 221/22* (2006.01)
*C07D 237/26* (2006.01)
*C07D 491/04* (2006.01)
*C07D 491/08* (2006.01)

(52) U.S. Cl.
USPC ........... 544/179; 544/182; 544/233; 536/23.1

(58) Field of Classification Search
USPC .......................... 544/179, 182, 233; 536/23.1
See application file for complete search history.

(56) References Cited

FOREIGN PATENT DOCUMENTS

| DE | 1770098 A1 | 9/1971 |
|----|------------|--------|
| EP | 1243579 A | 9/2002 |
| WO | WO98/16508 | 4/1998 |

OTHER PUBLICATIONS

Iwamoto et al Chem. Pharm. Bull. 1995, 43(5), 679-682.*
Boger et al J. Am. Chem. Soc. 1999, 121, 2471-477.*
Boger et al J. Am. Chem. Soc. 1987, 109, 2717-27.*
Barlow et al J.C.S. Perkin I, 1982, 1245-49.*
Katagiri et al , Chem. Pharm. Bull. 1988, 36(9), 3354-72.*
Kiselev et al Tetrahedron, 1999, 12201-10.*
Lipinska Tetrahedron, 2005, 61, 8148-58.*
International Search Report for PCT/EP2007/005361, mailed Nov. 7, 2007.
d'A. Rocha Gonsalves, A., et al., "Diels-Alder Reactions of 1,2,4-Triazines with Cyclic Vinyl Ethers", Elsevier Science Publishers, Amsterdam, NL, Bd. 49, Nr. 24, 1993, pp. 5277-5290.
Kiselev, V.D., et al., "Volume, Enthalpy and Entropy of Activation of the Diels-Alder Reaction of Dimethyl 1,2,3,5-tetrazine-3,6-dicarboxylate with 1-Hexene", Tetrahedron, Elsevier Science Publishers, Amsterdam, NL, Bd. 55, Nr. 41, Oct. 8, 1999, pp. 12201-12210.
Linpinska, T., "Experimental and theoretical FMO interaction studies of the Diels-Alder reaction of 5-acetyl-3-methytio-1,2,4-triazine with cyclic enamines", Tetrahedron, Elsevier Science Publishers, Amsterdam, NL, Bd. 61, Nr. 34, Aug. 22, 2005, pp. 8148-8158.
Panek, J.S., et al., "Synthesis of Aromatic 1,2-Diazines by Inverse Electron Demand Diels-Alder Reaction of Polymer-Supported 1,2,4,5-Tetrazines", Tetrahedron Letters, Elsevier, Amsterdam, NL, Bd. 37, Nr. 45, Nov. 4, 1996, pp. 8151-8154.
Sparey, T.J., et al., "Inverse Electron Demand Diels-Alder Reactions of 3,6-Dichloro-[1,2,4,5]tetrazine", Tetrahedron Letters, Elsevier Science Publishers, Amsterdam, NL, Bd. 39, Nr. 32, Aug. 6, 1998, pp. 5873-5874.
Stehl, A., et al., "Racemic and enantiopure 4-(piperidine-2'-yl)-pyridazines: novel synthesis of ananbasine-analogues with potential nicotinic acetylcholine receptor agonist activity—a new approach via Diels-Alder reaction with inverse electron demand", Tetrahedron, Elsevier Science Publishers, Amsterdam, NL, Bd. 58, Nr. 7, Feb. 11, 2002, pp. 1343-1354.
Taylor, Edward C., et al., "Intramolecular Diels-Alder Reactions of 1,2,4-Triazines. Synthesis of 2,3-Cyclopentenopyridines and 5,6,7,8-Tetrahydroquinolines", Journal of Organic Chemistry, American Chemical Society, Easton, US, Bd. 56, Nr. 5, May 1991, pp. 1807-1812.

(Continued)

*Primary Examiner* — Shaojia Anna Jiang
*Assistant Examiner* — Ganapathy Krishnan
(74) *Attorney, Agent, or Firm* — Perkins Coie LLP; Viola T. Kung

(57) ABSTRACT

The present invention relates to a process for linking two molecules by means of a Diels Alder reaction with inverse electron requirement (DARinv), comprising the following steps: reaction of a (a) triazine or tetrazine with one or more electron-attracting substituents on the ring as a diene component, the electron-attracting substituents being selected from:
  COOR
  C(O)NR$_2$
  CX$_3$ (X=halogen)
  halogen
  CN
  SO$_2$—R or SO$_3$—R
  PR$_2$
wherein R=H, alkyl, aryl, heterocycle, which in turn may be substituted, where appropriate, with alkyl, OH, SH, halogen, aryl, heterocycle, nitro, carboxyamido or amine group. —heterocyclic rings having 1, 2 or 3 N, O or S atoms with a ring size of 5 or 6 ring members, which are substituted with at least one carboxyl, sulfonic acid or phosphone group with (b) an isolated double bond or triple bond in a (hetero)carbocyclic ring or an isolated olefinic double bond or triple bond in a linear or branched hydrocarbon chain which may also contain heteroatoms, where appropriate, as a dienophile component.

9 Claims, 2 Drawing Sheets

(56) References Cited

OTHER PUBLICATIONS

Wan, Z-K, et al., "Dienophilicity of imidazole in inverse electron demand Diels-Alder reactions: cycloadditions with 1,2,4,5-tetrazines and the structure of zarzissine", Tetrahedron, Elsevier Science Publishers, Amsterdam, NL, Bd. 57, Nr. 26, Jun. 25, 2001, pp. 5497-5507.

\* cited by examiner

Diels Alder reaction with inverse electron requirement n = 1-8

PROCESS FOR THE COVALENT COUPLING OF TWO MOLECULES BY MEANS OF A DIELS-ALDER REACTION WITH INVERSE ELECTRON REQUIREMENT

This application is a National Stage of International Application PCT/EP2007/005361, filed Jun. 18, 2007; which claims the priority of Application No. EP06012414.6, filed Jun. 16, 2006.

TECHNICAL FIELD

The present invention relates to a process for covalently binding/linking two molecules by means of a Diels Alder reaction with an inverse electron requirement.

BACKGROUND OF THE INVENTION

When they investigate biological systems, molecular biologists and chemists time and again meet with the necessity of having to covalently bind two molecular units with each other, e.g. an oligosaccharide with a peptide, a reporter molecule with a biopolymer, two biopolymers with each other or a low-molecular therapeutic agent with a biopolymer. Usually, all of said compounds have a number of chemical functions whose respective reaction behaviour has to be observed under the conditions of the ligation reaction. Hence it follows that the chemoselective ligation reactions should have a clear reaction course without the other existing chemical functions or groups being attacked or actively interfering with the reaction event. This can only be realized if two functional groups reacting selectively with each other are involved in the ligation step. Furthermore, it would be desirable that such a ligation reaction can proceed without the use of protective groups in every environment and at a pH adapted to the respective biopolymer.

One of the few chemical reactions which can fully comply with all of these conditions is the cycloaddition, either of the 4+2 type, which is known as the Diels Alder reaction (FIG. 1; J. Sauer, 1966, Angew. Chem. 78, 233), or of the 3+2 type, which is known as 1,3 dipolar cycloaddition. The sharpless ligation was developed on the basis of this reaction (lit). A method also further developed in the past few years is the Staudinger ligation (Review: Angew. Chem. 2004, 116, 3168-3178).

DE-A-100 41 221.1 shows the application of the classical Diels Alder reaction as a ligation reaction, the diene being provided with electron-donating substituents and the dienophile being provided with electron-attracting substituents. In this connection, furan and its derivatives were used as dienes, and substituted maleinimides were used as dienophiles. This system was selected due to the simple accessibility of the respective components and the simple chemistry thereof. Many furans can easily be produced from saccharides and are available in major amounts. Like many chemical reactions, the Diels Alder reaction (hereinafter referred to as "DAR") can be reversed, above all at elevated temperatures. This reversibility is particularly developed in the furan/maleinimide system, which is caused by the high reactivity of the maleinimides for nucleophilic additions. This can readily be read off the use of maleinimides for labeling peptides or the linkage thereof. In this connection, the thiol group of the protein adds to the double bond of the maleinimide in a very rapid, irreversible reaction. Already the small amounts of maleinimide which are present by the back reaction of the DAR in the equilibrium are trapped by such an addition thus shifting the equilibrium towards the starting substances. This is a real drawback of the DAR since this significantly minimizes the yield of the desired product.

SUMMARY OF THE INVENTION

It is therefore the object of the present invention to provide a process by which even intricately synthesized compounds can be linked covalently and irreversibly with one another and which can also be used for establishing substance libraries.

This object is achieved by the subject matters of the claims.

The object is achieved by a Diels Alder reaction with inverse electron requirement, comprising the following steps: reaction of a (a) 1,2,4-triazine or 1,2,4,5-tetrazine or a 1,2-diazine with one or more electron-attracting substituents on the ring as a diene component, the electron-attracting substituents being selected from:
COOR
$C(O)NR_2$
$CX_3$ (X=halogen)
halogen
CN
$SO_2$—R or $SO_3$—R
$PR_2$
    wherein R=H, alkyl, aryl, heterocycle, which in turn may be substituted, where appropriate, with alkyl, OH, SH, halogen, aryl, heterocycle, nitro, carboxyamido or amine group.
    heterocyclic rings having 1, 2 or 3 N, O or S atoms with a ring size of 5 or 6 ring members, which are substituted with at least one carboxyl, sulfonic acid or phosphone group
with
(b) an isolated double bond or triple bond in a (hetero)carbocyclic ring or an isolated olefinic double bond or triple bond in a linear or branched hydrocarbon chain which may also contain heteroatoms, where appropriate, as a dienophile component.

DETAILED DESCRIPTION OF THE INVENTION

Figure 1:
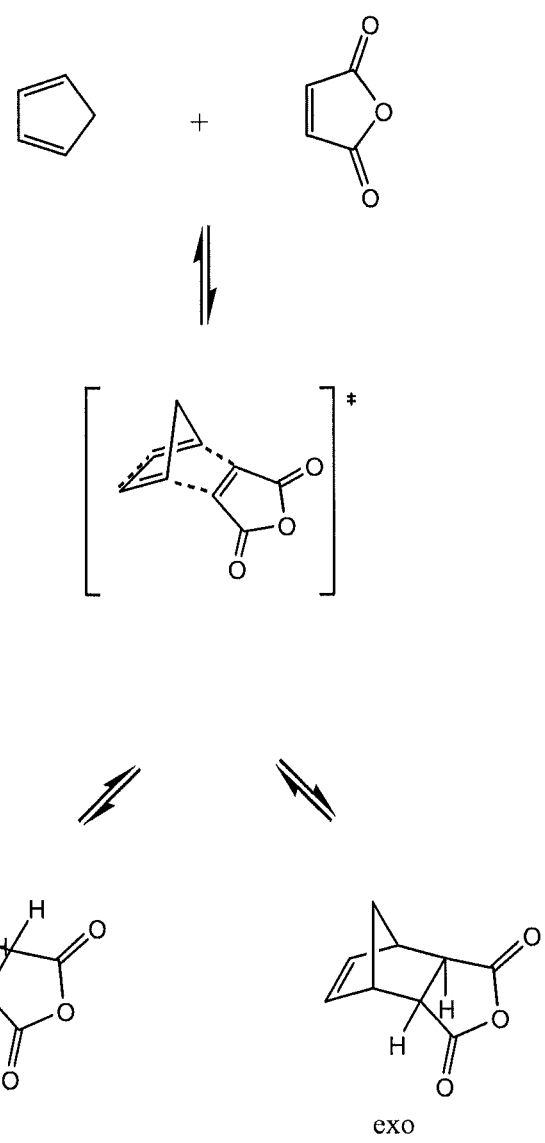
FIG. 1 illustrates the Diels Alder reaction.
Figure 2:
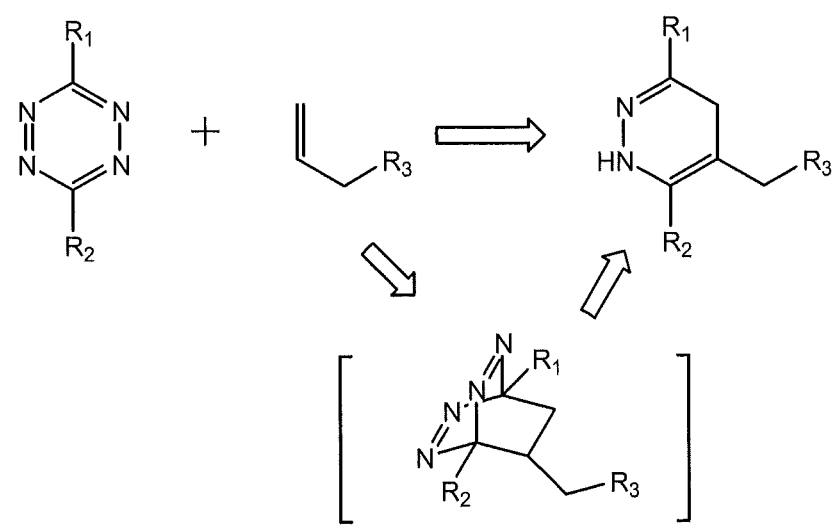
FIG. 2 illustrates the Diels Alder reaction with inverse electron requirement.
Figure 2:
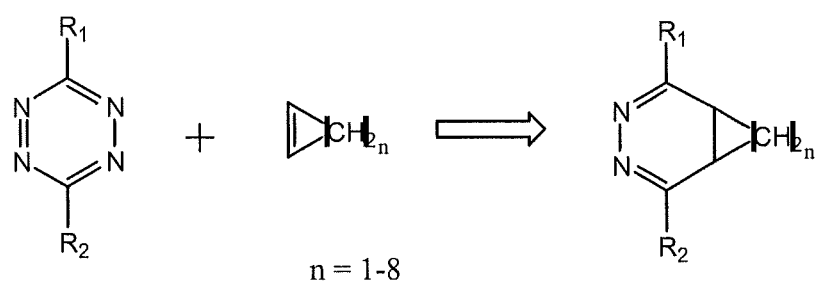

The inventors have turned to such Diels Alder reactions which proceed by splitting off a molecule portion thus fully shifting the equilibrium of the reaction towards the product. If the split-off molecule portion is volatile, a back reaction is rendered impossible. Along with some special dienes on the basis of the classical DAR, such as the cyclopentadienone, this reaction type is above all represented by the Diels Alder reaction with inverse electron requirement (FIG. 2). This reaction has been well investigated and above all introduced into the heterocycle synthesis. With this kind of DAR, the kind of the substituents in the diene and in the dienophile, as defined by O. Diels and K. Alder, are turned around or inverted. The diene is then provided with electron-attracting substituents thus becoming electron-deficient while the dienophile becomes rich in electrons due to its substitution. The DAR of the tetrachlorocyclopentadiene
with olefins is already characterized as a DAR with inverse electron requirement (hereinafter referred to as "DARinv"). As described by Sauer, such Diels Alder reactions with inverse electron requirement can already fully proceed at room temperature.

The criteria defined already at the beginning for the development of an effective ligation reaction are thus complied with by the inverse DAR in an almost model way. However, the precondition for this is the synthesis of suitably functionalized 1,2,4,5-tetrazines, 1,2,4-triazines and 1,2-diazines as dienes and of olefins as dienophiles. Since the compounds tailored for this purpose have not been known to date, the development of these syntheses for the particular intended use is based on the present application. Both possible variants of the DARinv could be verified as a ligation reaction: on the one hand, the introduction of the diene into the target molecule, e.g. a peptide, followed by the reaction with the saccharide formed as a dienophile, as well as the reverse procedure. Both the diene and the dienophile shall have maximum reactivity accompanied by maximum stability to be able to carry out the DARinv, if possible, in all solvents and at room temperature.

Diene Component

The objective of the synthesis of suitable dienes for functionalizing peptides, oligonucleotides, of surfaces or of therapeutic agents is the preparation of symmetrically or asymmetrically substituted 1,2,4,5-tetrazines, 1,2,4-triazines and 1,2-diazines, which can readily be incorporated into said biomolecules. However, the already known 3,6-dicarboxylic acid ester of the 1,2,4,5-tetrazine is not well suited as a starting product for the preparation of suitably functionalized 1,2,4,5-tetrazines as dienes. On the one hand, this compound which forms magnificently red crystals, in alcoholic and aqueous solvents does not have adequate stability, on the other hand nucleophilic substitution reactions on the ester groups are not possible since the attack of the nucleophile takes place on the tetrazine ring as such under these conditions. (Kämpchen T. et al. 1982, Chem. Ber., 115, 683-694.)

However, in the three-stage synthesis of this tetrazine, starting with the diazoacetic acid ester, the stage of the dihydro-1,2,4,5-tetrazine dicarboxylic acid ester is involved. As found by the inventors, nucleophilic substitution reactions can be carried out without any problems with this compound due to the major reactivity of the ester groups. Since the second nucleophilic substitution, above all with secondary amines, proceeds more slowly than the first one, it is also possible to produce monoamides. By a suitable reaction control it is possible to force back the second nucleophilic substitution so that dihydrotetrazine monoamides, such as benzylamide, can be obtained in pure form by simple recrystallization. This is also an important step for the production of functionalized dihydrotetrazine diamides for the derivatization of peptides. In this connection, it may be advantageous to initially introduce the much more stable dihydrotetrazines as subsequent diene components. Having terminated all reactions to be carried out, the oxidation to give tetrazine with the immediately following DARinv is carried out. Further possibilities for the preparation of more stable monofunctionalized tetrazines on the basis of diaryltetrazines are shown below.

A synthesis route for the preparation of triazines consists of the reaction of 1,2-diketo derivatives with amide hydrazones. In this way, the tricarboxylic acid ester of 1,2,4-triazine can also be produced in major amounts according to the literature. Here, the ester functions can be reacted without any problems with nucleophiles, such as amines. It has not yet been possible to discriminate between the ester functions in the reaction with amines. An ester function is sufficient for a selective introduction of the triazine residue into any molecules. However, in order to obtain the diene activity of the triazine, sufficient electronegative substituents should be present.

Triazines-1,2,4 are generally less reactive in the DARinv than the tetrazines. However, their reaction rate still suffices for ligation reactions, above all when they are reacted with a very reactive dienophile.

The 1,2-diazines, which are formed by oxidation of the dihydropyridazines forming in the DARinv of tetrazines with olefins, have a DARinv activity even lower than that of dienes. They form directly in the DARinv of tetrazines
with triple bonds or enamines. As a result, there is also the possibility to link any two molecules containing a dienophilic anchor group in given way with each other in a sequence, based on a tetrazine via the diazine by two successive DARinv reactions, discontinued by the oxidation of the dihydropyridazine into pyridazine.

Tetrazines, triazines and diazines, which can be monosubstituted or polysubstituted with electron-attracting functional groups are suited as the diene component according to the invention. These electron-attracting functional groups can be selected from:

COOR (preferably: COOH)
$C(O)NR_2$
$CX_3$ (X=halogen) (preferably $CF_3$)
halogen (F, Cl, Br or I)
CN
$SO_2$—R or $SO_3$—R
$PR_2$ The functional groups R, which preferably provide a functionality for linkage to further molecules (e.g. to peptides, saccharides or nucleic acids), can be selected from H, alkyl, aryl, heterocycle, wherein R can in turn be substituted, where appropriate, with alkyl, OH, SH, halogen, aryl, heterocycle, nitro, carboxyamido or amine group. Said functional groups can also be directly linked with the tetrazine, triazine or diazine.

Heterocyclic rings having 1, 2 or 3 N, O or S atoms with ring sizes having 5 or 6 ring members are also in consideration as electron-attracting substituents which may be directly bound to the tetrazine, triazine or diazine. At least 1 carboxyl group, sulfonic acid or phosphone group should be bound to these rings for binding further functionalities.

"Alkyl" means $C_1$-$C_{20}$, preferably methyl, ethyl, iso-propyl, tert.-butyl, etc. The aryl and/or heterocycle substituents may be selected from: phenyl, thienyl, thiophenyl, furyl, furanyl, cyclopentadienyl, pyranyl, pyrrolyl, imidazolyl, pyrazolyl, pyridyl, pyrazinyl, pyrimidinyl, pyrazinyl, pyridazinyl, thiazolyl, oxazolyl, indolyl, furazannyl, pyrrolinyl, imidazolinyl, pyrazolinyl, thiazolinyl, triazolyl, tetrazolyl group, as well as the positional isomers or the heteroatom(s) which said groups may comprise, a residue consisting of carbocyclic condensed rings, such as the naphthyl group or the phenanthrenyl group, a residue consisting of condensed heterocyclic rings, e.g. benzofuranyl, benzothienyl, benzimidazolyl, benzothiazolyl, naphtho[2,3-b]thienyl, thianthrenyl, isobenzofuranyl, chromenyl, xanthenyl, phenoxathionyl, indolizinyl, isoindolyl, 3H-indolyl, indolyl, indazolyl, purinyl, quinolizinyl, isoquinolyl, quinolyl, phthalzinyl, naphthyridinyl, quinoxalinyl, quinazolinyl, quinolinyl, pteridinyl, carbazolyl, β-carbolinyl, cinnolinyl, acridinyl, phenazinyl, phenothiazinyl, phenoxazinyl, indolinyl, isoindolinyl, imidazopyridyl, imidazopyridmidinyl or also the condensed polycyclic systems consisting of heterocyclic monocycles, as defined above, such as thionaphthenyl, furo[2,3-b]pyrrole or thieno[2,3-b]furan, and in particular the phenyl groups, furyl groups, such as 2-furyl, imidazolyl, such as 2-imidazolyl, pyridyl, such as 2-pyridyl, 3-pyridyl, 4-pyridyl, pyrimidinyl, such as pyridmid-2-yl, thiazolyl, such as thiazol-2-yl, thiazolinyl, such as thiazolin-2-yl, triazolyl, such as triazolyl-2-yl, tetrazolyl, such as tetrazol-2-yl, benzimidazolyl, such as benzimidazol-2-yl, benzothiazolyl, benzothiazol-2-yl, purinyl, such as purin-7-yl, or quinolyl, such as 4-quinolyl.

However, the diene component can also carry amino acid, peptide, saccharide, lipid or oligonucleotide or nucleic acid substituents at one or more positions. All kinds of pharmaceutical active substances, tags, dyes, complexes (e.g. carborane, ferrocene), quantum dots, chelating/complexing agents, diagnostic agents or therapeutic agents and combinations thereof can be coupled to the diene compounds.

Preferred diene components are all esters of the prepared tetrazines, triazines and diazines and the compounds derived therefrom: e.g. tetrazine monoamides, tetrazine diamides, tetrazine-3-trifluoromethyl-6-carboxylic acid amide, triazine tricarboxylic acid monoamides, diamides, and triamides, 3-carboxyamide-5,6-bis-trifluoromethyl-triazine1,2,4,1,2-diazines 3,6-diaryl 4,5-dicarboxylic acid amides. Likewise, the homologs thereof can be used with an ethyl or propyl group instead of a methyl group. The tetrazines mentioned can rather easily be produced by oxidation from the corresponding dihydro compounds, which are accessible via the dihydrotetrazine dicarboxylic acid ester which, in turn, can be readily produced from the purchasable diazoacetic ester in two stages.

Dienophile Component

A terminal olefinic double bond without additional activation suffices as a dienophile for the DARinv, a function which does not occur, or only occurs rarely, in biological systems suffices as a dienophile for the DARinv. A twofold substituted double bond as occurring in fatty acids or lipids, only reacts very slowly under normal conditions in the sense of DARinv. A methylene group, such as in the perilla alcohol, also reacts very slowly at room temperature (60 hours) in the sense of the DARinv thereby forming the expected adduct. However, as soon as a double bond is integrated within a carbocyclic ring system, it reacts much more rapidly than dienophile, the reactivity decreasing with increasing ring size, starting with the cyclopropene, and passing through a minimum with cyclohexene. In ring systems greater than seven rings, triple bonds can also react as inverse dienophiles.

According to the invention, a carbocyclic ring is understood to mean every monocyclic, bicyclic or tricyclic carbon ring. These rings may also contain heteroatoms. (N, O, S, Si)

An isolated olefinic double bond or triple bond is also in consideration as the dienophile component in a linear or branched hydrocarbon chain which, where appropriate, may also contain heteroatoms (N, O, S, Si).

Since the reaction rates of different dienophiles differ from the same diene in the DARinv by decimal powers, specific reactions can be carried out in the presence of two different dienophiles in a template. For example, Sauer (Eur. J. Org. Chem. 1998, 2885-2896) describes a difference in the reactivity between the cyclobutene and cyclopentene by a factor of 12 with respect to the unsubstituted tetrazine whereas a factor of 1200 is observed between cyclopentene and cyclohexene. Hence it follows that in the presence of a cyclobutene and a cyclohexene in the same molecule, a difference in the reaction rate by about a factor of 1200 is observed. Based on the yield this means a contamination of about one one-tenth of a percent. Differently substituted tetrazines, triazines and diazines have as dienes, of course, also different reactivities as compared to the same dienophile so that reactivity scales of dienes and dienophiles can be defined which permit very specific and selective multiple reactions. When this scheme is extended by the classical Diels Alder reaction, which as to the electronic demands on diene and dienophile is absolutely orthogonal with respect to the inverse variant, a widely variable and efficient network of ligation reactions comes about. The dienophile for a DARinv is often created by an upstream classical DAR. A very nice example of this sequence is the DAR between cyclopentadiene and MSA (maleic acid anhydride) thereby forming the norbornene anhydride or the DAR between cyclooctatetraene and MSA where an adduct forms which simultaneously contains a cyclobutene ring and a cyclohexene ring in the same molecule. Since both the norbornene anhydrides (exo and endo) as well as the bicyclic COT anhydride can readily be further derivatized with amines, they can easily be converted into functional molecules suited for the ligation. By means of the metathesis reaction, it is also possible to generate ring systems having double bonds. By photochemical ring closure reactions of cyclic 1,3-dienes it is possible to produce ring systems having double bonds. Cyclobutenes can also be produced as reactive dienophiles by photochemical ring closure reactions of cyclic 1,3-dienes so that the ligation technique based on the DARinv can be combined with photolithography.

Literature describes that the surfaces of carbon (diamond, fullerenenes, carbonanotubes), germanium and silicon behave like dienophiles in the classical DAR. (Roucoules V. et al., 2005, Langmuir 21, 1412-1415). They react with cyclopentadiene thereby forming the norbornene ring system, a dienophile suitable for DARinv again forming. Thus, these surfaces can be functionalized without any problems by DARinv. In combination with the photochemical activation by cyclization of 1,3-dienes into cyclobutenes, completely novel spatial functionalization possibilities form as a result of the sequence: 1.) Covalent anchorage of a cyclic 1,3-diene to a surface or a semiconductor 2.) photochemical cyclization to cyclobutene, 3.) DARinv with a diene to which a protein or a saccharide, for example, is covalently bound.

Preferred dienophile components are acids and anhydrides, the functionalized imides and amides derived therefrom and the reduction products thereof, as well as the associated esters and the substitution and reduction products thereof which contain a strained or a terminal double bond, e.g. exo- or endo-norbornene dicarboxylic acid anhydride, both norbornene monocarboxylic acid esters, cyclobutene monocarboxylic acid esters, cyclobutene dicarboxylic acid anhydride, sym. cyclopentene carboxylic acid, cyclohexene dicarboxylic acid anhydride, sym. cycloheptene carboxylic acid, the readily accessible tricyclic COT-MSA adduct, or the corresponding mononcarboxylic acid from COT and acrylic acid. The also readily accessible 2-allyl-2-propargyl-malonic ester also has two differently reactive dienophile groups. Further preferred dienophile components are dehydroproline, allyl proline, allylmalonic ester, allylgalactose, allyl silsesquioxane, as well as all compounds carrying an allyl, butenyl or pentenyl group. Where appropriate, the dienophile component can also be monosubstituted or polysubstituted with functional groups. The functional groups can be selected from e.g. alkyl chains ($C_2$-$C_{20}$, preferably methyl, ethyl, isopropyl, tert.-butyl, etc., where appropriate, halogen substituted), OH, SH, halogens, aryl, carboxyl, carbonyl, nitro, carboxyamido, keto, sulfoxide, sulfone, sulfonic acid, sulfide, sulfate, phosphoric acid or amino groups which are bound directly or via alkyl residues. The dienophile component can also contain aromatic or heterocyclic residues. It can be selected from: phenyl, thienyl, thiophenyl, furyl, cyclopentadienyl, furanyl, pyranyl, pyrrolyl, imidazolyl, pyrazolyl, pyridyl, pyrazinyl, pyrimidinyl, pyrazinyl, pyridazinyl, thiazolyl, oxazolyl, indolyl, furazannyl, pyrrolinyl, imidazolinyl, pyrazolinyl, thiazolinyl, triazolyl, tetrazolyl group, as well as the positional isomers of the heteroatom(s), which may comprise these groups, a residue consisting of carbocyclic condensed rings, e.g. the naphthyl group or the phenanthrenyl group, a residue consisting of condensed heterocyclic rings, e.g. benzofuranyl, benzothienyl, benzimidazolyl, benzothiazolyl, naphtho[2,3-b]thienyl, thianthrenyl, isobenzofuranyl, chromenyl, xanthenyl, phenoxathionyl, indolizinyl, isoindolyl, 3H-indolyl, indolyl, indazolyl, purinyl, quinolizinyl, isoquinolyl, quinolyl, phthalzinyl, naphthyridinyl, quinoxalinyl, quinazolinyl, quinolinyl, pteridinyl, carbazolyl, β-carbolinyl, cinnolinyl, acridinyl, phenazinyl, phenothiazinyl, phenoxazinyl, indolinyl, isoindolinyl, imidazopyridyl, imidazopyridmidinyl or also the condensed polycyclic systems consisting of heterocyclic monocycles, as defined above, for example, such as thionaphthenyl, furo[2,3-b]pyrrole or thieno[2,3-b]furan, and in particular the phenyl, furyl groups, such as 2-furyl, imidazolyl, such as 2-imidazolyl, pyridyl, such as 2-pyridyl, 3-pyridyl, 4-pyridyl, pyrimidinyl, such as pyridmid-2-yl, thiazolyl, such as thiazol-2-yl, thiazolinyl, such as thiazolin-2-yl, triazolyl, such as triazolyl-2-yl, tetrazolyl, such as tetrazol-2-yl, benzimidazolyl, such as benzimidazol-2-yl, benzothiazolyl, benzothiazol-2-yl, purinyl, such as purin-7-yl, or quinolyl, such as 4-quinolyl.

The versatile possible substitutions in the diene and dienophile allow a diene active in the DARinv to simultaneously contain a diene structure or a dienophilic group of the classical DAR in the same molecule without a reaction occurring. The same applies naturally to the inverse dienophile as well. As a result, a plurality of selective ligation possibilities form by simultaneously proceeding, directed DAR and DARinv.

However, the dienophile component can also carry amino acid, peptide, saccharide, lipid or oligonucleotide or nucleic acid substituents on one side. All kinds of pharmaceutical active substances, tags, dyes, complexes (e.g. carborane, ferrocene), quantum dots, chelating/complexing agents, diagnostic agents or therapeutic agents can also be linked to the dienophile component.

Exploratory kinetic DARinv measurements for the produced dienes and dienophiles show the expected broad reaction behavior.

The below Table 2 shows rate constants k ($s^{-1}*mol^{-1}*l$) for the reaction between tetrazines (column 1) with the respective dienophiles (line 1).

TABLE 2

| | exo 28 | 17 | endo 27 | 26 | 13 |
|---|---|---|---|---|---|
| 5 | $2.2*10^{-2}$ | $1.3*10^{-1}$ | $3.6*10^{-3}$ | $2.8*10^{-3}$ | 3.4 |
| 8b | $2.8*10^{-2}$ | $1.8*10^{-1}$ | $6.9*10^{-3}$ | $5.6*10^{-3}$ | $2.8*10^{-2}$ |
| 8c | $2.3*10^{-2}$ | $6*10^{-2}$ | $6.7*10^{-3}$ | $5.3*10^{-3}$ | $2*10^{-1}$ |

TABLE 2-continued

| Structure | | | |
|---|---|---|---|
| tetrazine-C(O)NH-CH2-CO2Me / C(O)NMe2 | $<10^{-4}$ | $<10^{-4}$ | $1.4*10^{-2}$ |
| 16 (bicyclic imide with NHBoc, CO2H) | 14 (bicyclic imide with CH2CH2OH) | 27 (CH2=CHCH2-CH(CO2Et)2) | |
| 5 (dimethyl tetrazine-3,6-dicarboxylate) | $4.4*10^{-1}$ | 1.63 | $4.8*10^{-3}$ |
| 8b (bis-glycine methyl ester amide of tetrazine) | $4.4*10^{-1}$ | $4.8*10^{-2}$ | $7.3*10^{-3}$ |
| 8c (bis-ethanolamine amide of tetrazine) | $1.1*10^{-1}$ | $6.9*10^{-1}$ | $8*10^{-3}$ |

TABLE 2-continued

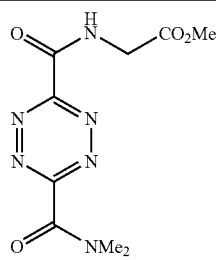

Legend:
rate for the rection for the reaction DARinv of dienes with dienophiles in liter mol$^{-1}$s$^{-1}$;
n.d. means not yet measured.
n.d.(+) means: reaction is carried out, however, is too slow for the measurements, DAR adduct is characterized.

Legend: rate constants for the reaction for the reaction DARinv of dienes with dienophiles in liter mol$^{-1}$s$^{-1}$; n.d. means not yet measured. n.d.(+) means: reaction is carried out, however, is too slow for the measurements, DAR adduct is characterized.

The conduction is very simple since the tetrazines have an absorption maximum of sufficient intensity at 520 nm whose reduction can be very well traced by means of photometry. The kinetic analysis supplies a rate law of second order. The results are summarized in the above table.

The analysis of the rate constant clearly shows that irrespective of the kind of substitution the N,N'-monoalkyl diamides of tetrazine 8b and 8c only have a diene activity slightly lower than diester 5. This is an important precondition for the use of the diamides as reactive dienes in DARBinvB for the ligation of molecules. A consideration of the rate constants of the dienophiles reveals very well the decrease in the order Reppe-ester, exo-norbornene, endo-norbornene and allyl compounds by a decimal power each. The measured rate constants show that the tricyclic Reppe-ester 13 and its derivatives 14 and 16 represent extremely reactive dienophiles. At 25° C. and with equimolar amounts of the reactants, the reactions are concluded within 10-60 minutes. In comparison with the Reppe-Ester 13, the cyclobutene dicarboxylic acid anhydride shows a clearly lower reactivity and behaves like the endo-norbornene derivatives. Here, a repelling interaction of the carbonyl groups of the anhydride ring with the carbonyl groups of the particular diene obviously occurs in the transitional state. This assumption is supported by the differences in the reaction rates of the exo- and endo-norbornene anhydrides and the derivatives thereof where such interactions can only occur with the endo compounds so that they have a reaction rate lower by a factor of 10 with respect to the exo compounds. When the carbonyl groups are removed by reduction, as in the tricyclic amino alcohol 15, the second double bond can also react in the molecule as a dienophile, which was proven by kinetic measurements. The conduction of the sequential DARinv is shown below with this amino alcohol.

The introduction of only one dimethylamide group as in 11b causes a marked reduction of k and only shows a measurable reaction rate with reactive dienophiles, such as 13. Thus, the reactivity of the tetrazine diamides can be controlled by the degree of the substitution on the nitrogen atom of the amide group. As a result, this structural variation can also be utilized to increase the selectivity in the reaction with different dienophiles.

Like the corresponding exo and endo norbornene derivatives, the tricyclic Boc-lysine 16 can be incorporated N-terminally into structurally differing peptides (see Ills. 12 and 18). All peptides react at 20° C. with tetrazine 8c as a model compound, the rates being only slightly less than those of the lysine building block 16. However, a dependence of the reaction rate on the peptide structure can be seen. Although peptides 22 and 23 contain the same dienophile, the strongly basic peptide 22 P[37]P responds much more slowly. It might be that the spatial structure of this basic peptide is responsible for a reduction in the reaction rate. These results suggest that as a function of their structure larger peptides still enter into the DARinv at a sufficient rate. Along with the described dicyclic and tricyclic dienophiles, amino acids, such as the commercially available allyl proline and dehydroproline, might also be incorporated into the peptide chain as dienophiles. The inventors have found that both amino acids react very rapidly with the tetrazine thereby forming the adducts to be expected. Non-natural amino acids can be incorporated enzymatically into peptides P[38]P; thus, peptides having dienophilic anchor groups are also selectively accessible by means of biosynthesis.

TABLE 3

Summary of the determined rate constants for the reaction between tetrazine 8c and peptides 21-25.

| Sequence | Tetrazine | K (sP − 1P * molP − 1P * l) | Mass DA adduct |
|---|---|---|---|
| Nor-Lys-EILDV (21) (M = 861.45) | 8c | 8.5 * 10P − 3P | Calc.: 1089.5 Found: 1089.5 (MP + P); 1121.6 ([M + CHB3BOH]P + P) |
| Nor-Lys | 8c | 1.0 * 10P − 2P | Calc.: 620 Found: 621.3 ([M + H]P + P) |
| COT-Lys-GPKKKRKV (22) (M = 1194.7) | 8c | 1.5 * 10P − 3P | Calc.: 1424.9 Found: 1424 ([M + H]P + P); 1456 ([M + CHB3BOH + H]P + P) |
| COT-Lys-GRGDSP (23) (M = 899.4) | 8c | 2.1 * 10P − 1P | Calc.: 1127.5 Found: 1128.5 ([M + H]P + P); 1159.5 ([M + CHB3BOH]P + P) |
| COT-LysPBOCP (24) (M = 430.2) | 8c | 2.9 * 10P − 2P | Calc.: 658.3 Found: 659 [M + H]P + P, 681 [M + Na]P + P |
| COT-Lys-EILDV (25) (M = 899.4) | 8c | 5.2 * 10P − 2P | Calc.: 1127.5 Found: 1128.5 [M + H]P + P, 1160.6 [M + CHB3BOH + H]P + P |

The inverse Diels Alder reaction is a reaction where rather low activation energies are to be overcome so that these reactions can already proceed at room temperature or at slightly elevated temperatures. It strongly depends on the temperature, which suggests a highly negative entropy as can be expected for a DAR. Diels Alder reactions can be accelerated by high pressure. In recent years, a number of catalysts have become known which can effectively catalyze Diels Alder reactions under mild conditions (K. Pindur et al., Chem. Rev. 1993, 93, p. 741-761; Kündig et al., Angew. Chem. 1999, 111, p. 1298-1301). Ultrasound also has an accelerating effect on the DAR. As to the yields, the inverse Diels Alder reaction offers major advantages since it proceeds without further by-products and with almost quantitative yield. The inverse Diels Alder reaction is thus used by the inventors to establish complex biological molecules and libraries. A clever substitution of both initial compounds (diene and dienophile) with functional groups or residues thus enables the access to molecules which may contain three or even four different residues.

By means of the DARinv the most widely varying molecules can be linked with one another or ligated to one another, even several times or in sequence. For example, these are amino acids, peptides, proteins, antibodies, saccharides, nucleic acids, nucleosides, solid phase surfaces, nanoparticles, dyes, therapeutic agents, diagnostic agents, chelating/complexing agents, quantum dots, membranes, surfaces, semiconductors.

The terms "peptide" and "protein" comprise peptides and proteins, respectively, of any length and complexity and also glycoconjugates.

The term "saccharide" comprises saccharides of any kind, in particular monosaccharides, disaccharides, oligosaccharides or polysaccharides (e.g. monoantennary, diantennary, triantennary, multiantennary as well as dendritic saccharides) in all stereoisomeric and enantiomeric forms. These can be pentoses or hexoses, which are available in the L or D form. Preferred as monosaccharides are in particular glucose, more particularly α- and β-D glucose, fructose, galactose, mannose, arabinose, xylose, fucose, rhamnose, digitoxose and derivatives thereof. Examples of suitable disaccharides are in particular saccharose, maltose, lactose or gentobiose, either linked 1,4 or 1,6, as well as derivatives thereof. Saccharides are here also sugar alcohols, polyols inositols and derivatives therefore, in particular cis-inositol, epi-inositol, allo-inositol, myo-inositol, muco-inositol, chiro-inositol, neo-inositol, scyllo-inositol, pinpollitol, streptamine, quercitol, quinic acid, shikimic acid, conduritol A and B, validatol and quebrachitol, e.g. from galactinols, from both vegetable sources, such as sugar beets (obtainable therefrom: hydroxymethylfurfural; F. W. Lichtenthaler, Mod. Synth. Meth. 1993, 6, p. 273-376), as well as from milk products or compounds recovered by enzymatic enantiomer separation. In addition, saccharides usable according to the invention are glycol conjugates. They may be conjugates of e.g. saccharides with peptides, lipids, acids (--> esters), alkyl residues (---> ethers), heterocycles or other carbohydrates. An example of glycol conjugates is Z1-Z10, a mixture of 10 glyco conjugates. The Z1-Z10 compounds are naturally occurring glycopeptides, glycoproteins and lipopolysaccharides. Derivatives of said saccharides are e.g. saccharides protected with protecting groups (e.g. benzoyl, silyl, dimethoxytrityl) and/or saccharides modified with functional groups, such as amino, nitro, sulfate, carboxy, carboxyamido, keto, sulfoxide, sulfonic, sulfonic acid, phosphoric acid, phosphonic acid, mono/di/trialkylamide groups or halide groups. The above saccharides can occur in nature or be produced synthetically.

The term "nucleic acid" refers to a mononucleotide, dinucleotide or oligonucleotide. Oligonucleotides also include DNA, DNA adducts, DNA constructs, nucleic acid analogues (e.g. PNA or LNA), RNA (sense/antisense) or siRNA.

The term "solid phase surface" means any (modified) surface to which biomolecules can be bound, e.g. conventional supports for the biochip/array production, e.g. made of glass, films, membranes (PP, PE, nylon, cellulose, cellulose mixed ester, PA, semiconductor, nanotubes, chitin, chitosan, semipermeable membranes, simplex membranes, ceramics, hybrid polymers, metals, nanocomposites).

The term "nanoparticles" means particles within the size range of less than 1000 nanometers, which are used in particular for coatings or diagnostic purposes. These are e.g. "quantum dots" or gold nanoparticles which are used in particular for the electron-microscopic investigation of biomolecules.

Diagnostic agent is a generic term for the reagents used in clinical chemistry and in medical laboratories for the biochemical analysis. They assist in a medical diagnosis (Greek diágn☐sis=knowledge, assessment) or the monitoring of therapeutic measures by generating information on physiological or pathological conditions.

The investigations made therewith can be made in vivo and in vitro. The diagnostic agents can be divided into chemical, biochemical, immunological and DNA-analytical methods: The term "diagnostic agent" comprises e.g. radiochemical compounds including fluorine 18 for PET investigations, quantum dots, dyes and antibodies for in vitro and in vivo investigations.

The DARinv is a standard method of organic chemistry and the reaction conditions are well known to a person skilled in the art or can be looked up in relevant textbooks. Based on the present invention, the DARinv is preferably carried out in any solvents between 20° C. and 100° C. Preferred solvents are water or alcohols, such as methanol or ethanol, dichloromethane, dioxin, tetrahydrofuran, aprotic poly solvents, such as DMF.

The above described system is also suited for the controlled release of parts of the dienophile or diene component after concluded anchorage of this component to a polymer carrier by the DARinv. If the dienophile, for example, carries a therapeutic agent, a system is thus available that can be used for the controlled and controllable release of medicaments of a solid phase by either hydrolytic or enzymatic cleavage at the site of action. Extending the above described reactions, the method according to the invention provides a possibility of linking peptides with saccharides, peptides with nucleic acids, saccharides with nucleic acids, and the particular components with itself if one component was linked to a diene and the other to a dienophile. The resulting Diels Alder adducts can still be modified, e.g. by oxidation or also by hydrogenation of the double bond or by addition reactions to this double bond.

In order to synthesize major clusters or libraries, the steps of the method according to the invention must be carried out several times in succession.

The diene or dienophile component can be found several times in a molecule. This also applies to the above described combination possibilities with the classical DAR. Suitable, readily accessible compounds are specified under "linker systems from dienophiles". The same applies to the dienes, in particular the combination of tetrazine and triazine being of particular interest because of the different diene reactivity in the DARinv.

Some important preferred aspects of the present invention are to be emphasized below, which are not to be interpreted as a limitation of the broad method concept.

Therefore, some presentation possibilities of dienes, then dienophiles and finally the Diels Alder reaction with inverse electron requirement are described below.

Presentation of Substituted Triazines and Tetrazines (Diene Component):

Tetrazines:

Tetrazines have a high reactivity as dienes in the inverse DAR. The model compound for many investigations is the well accessible tetrazine dicarboxylic acid dimethyl ester. The modifications necessary for the purpose of this invention of this compound, e.g. nucleophilic substitutions, however, result in decomposition. On the contrary, many reactions of the ester function with nucleophiles can be carried out rapidly and without any problems with the dihydro precursor. Since the rate of the first nucleophilic substitution with amines is usually greater than the rate of the second nucleophilic substitution, it is readily possible to produce monosubstituted amides and thus also open up the route for the preparation of asymmetric diamides. The subsequent oxidation of the dihydro compounds to give tetrazines can be carried out with a plurality of oxidants, such as $Fe(III)Cl_3$, nitrite, bromine or $H_2O_2$. A selection of the prepared compounds is shown below and illustrates the possibilities of the synthesis concept. Thus, this enables the production of the suitable compound for every application. In this connection, the oxidation to give tetrazine can be carried out at the very end of a reaction sequence since tetrazine dicarboxylic acid amides are much more stable than the tetrazine dicarboxylic acid ester per se.

Dihydro-tetrazine mono-methylamides

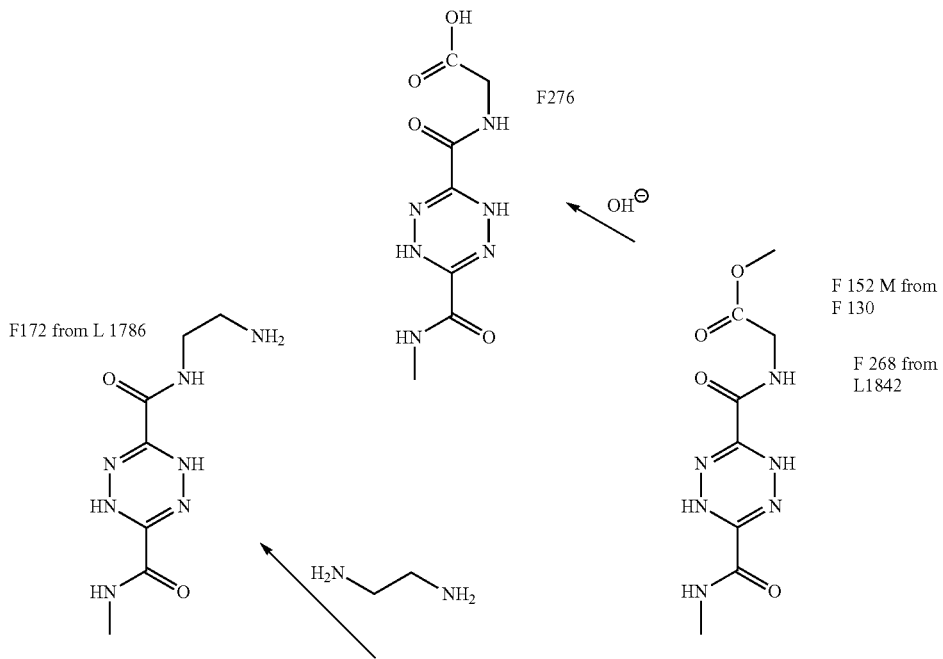

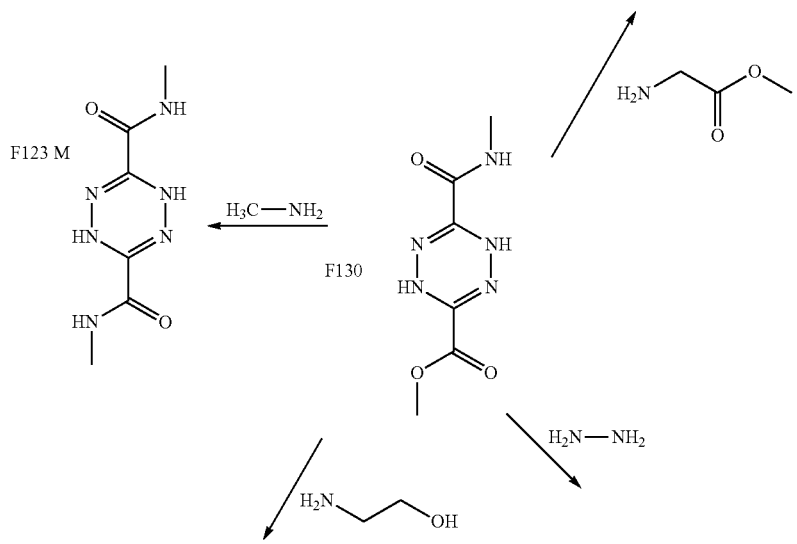

-continued
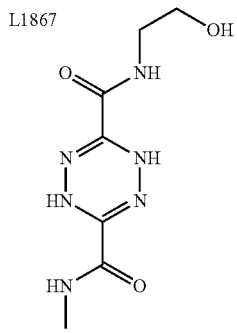
L1843 from L 1837
L1867
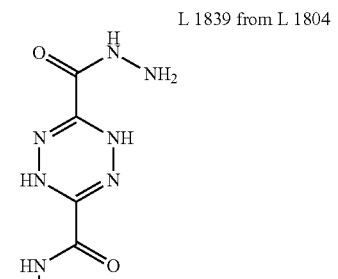
L 1839 from L 1804
Dihydro-tetrazine mono-dimethylamides
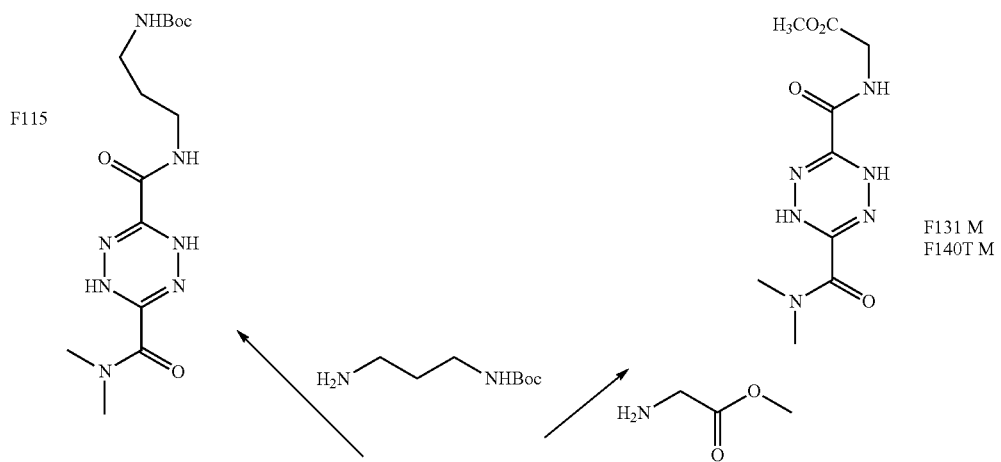
F115
F131 M
F140T M
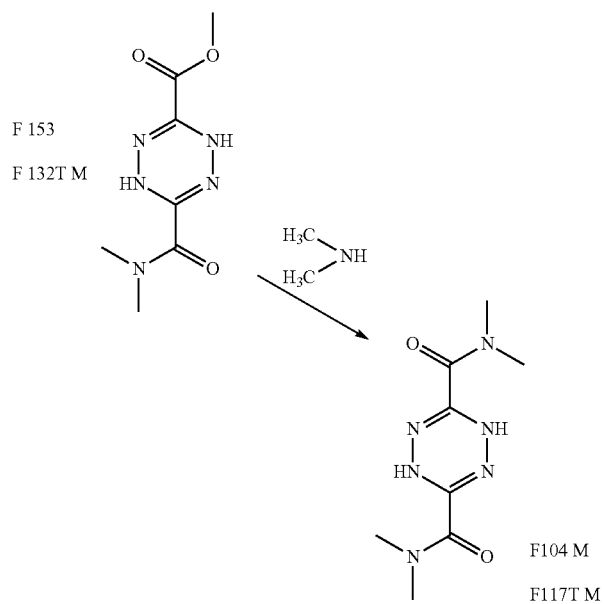
F 153
F 132T M
F104 M
F117T M -continued
Substituted by tetrazine dihydro monobenzylamide
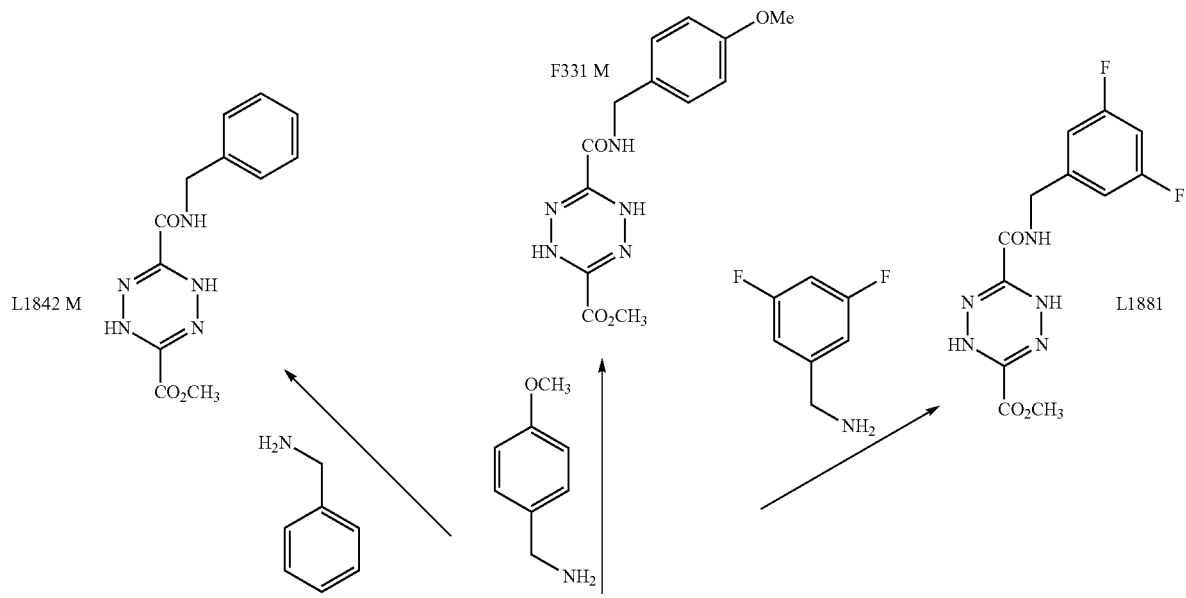
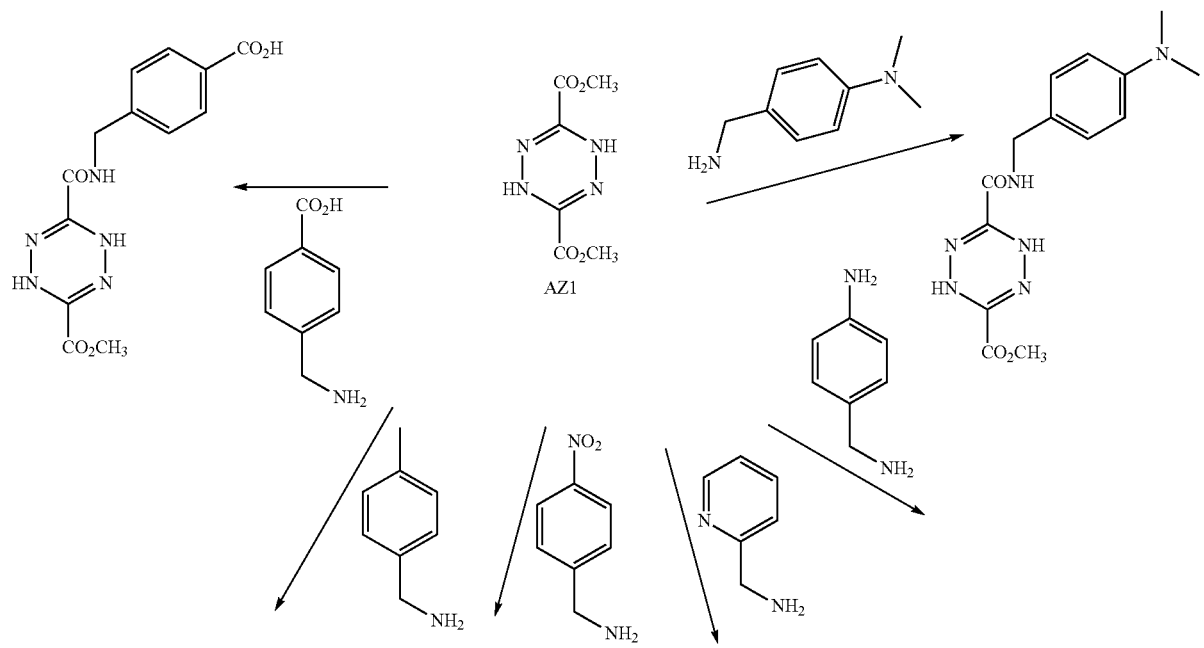

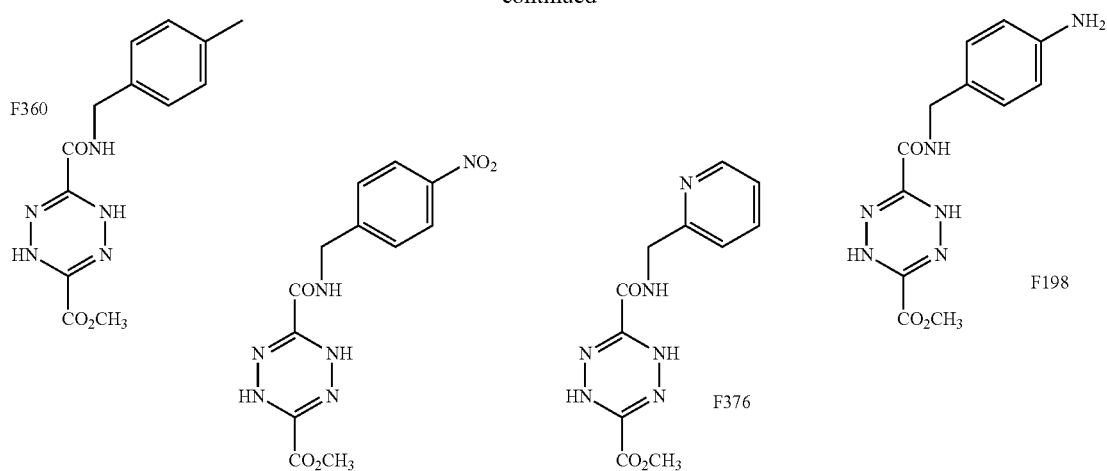
Tetrazine diamide benzyl
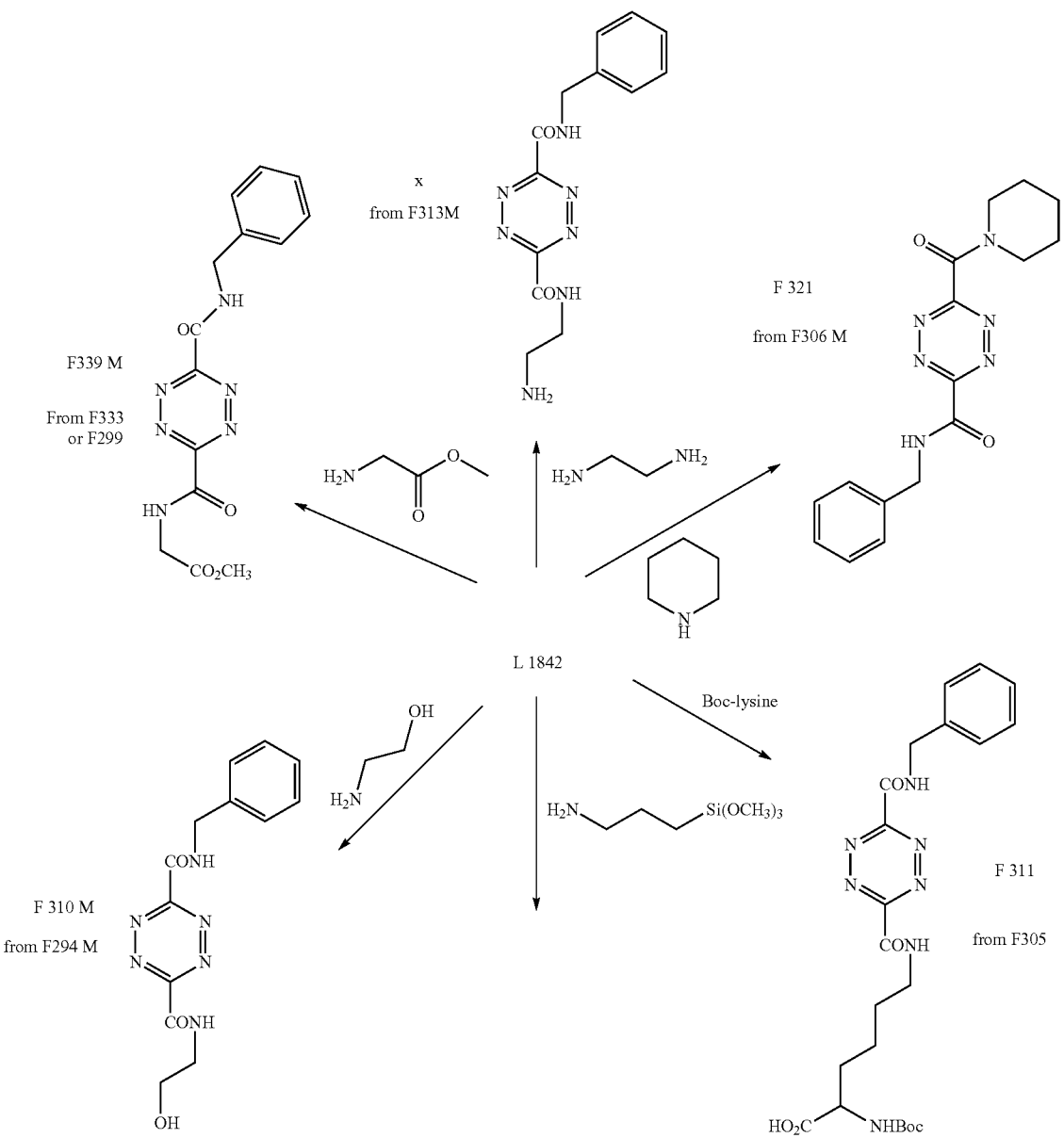
L 1842

-continued
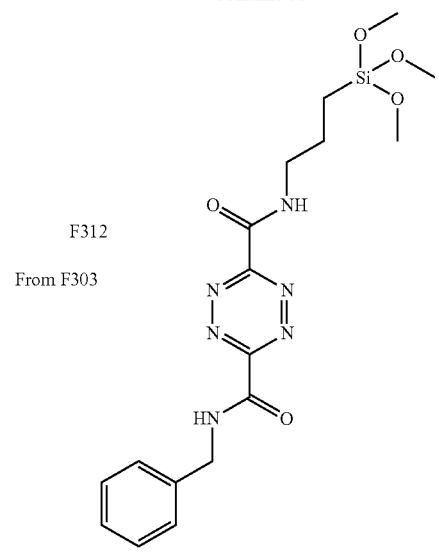
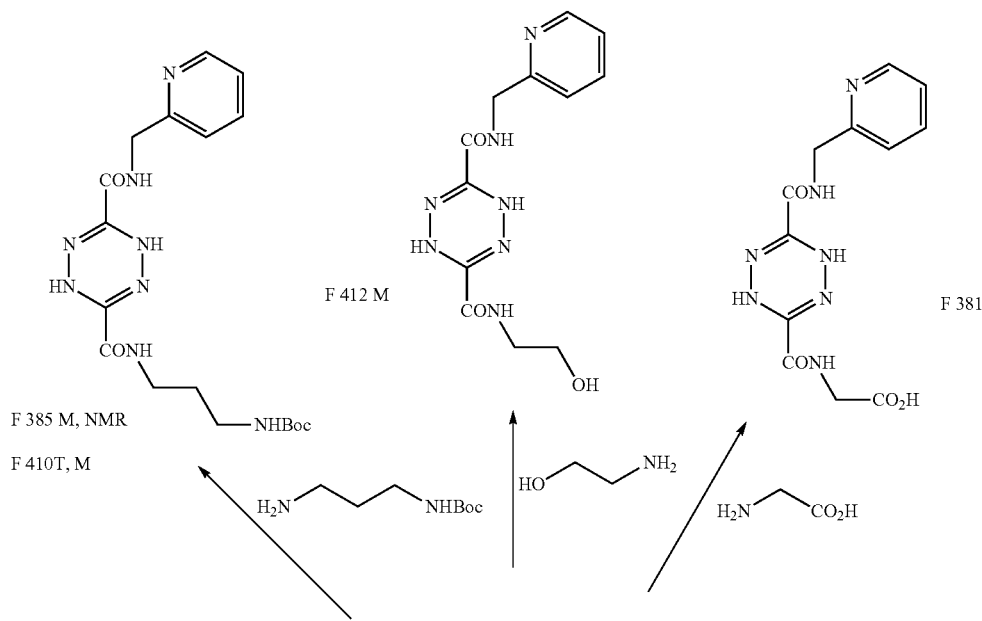

-continued
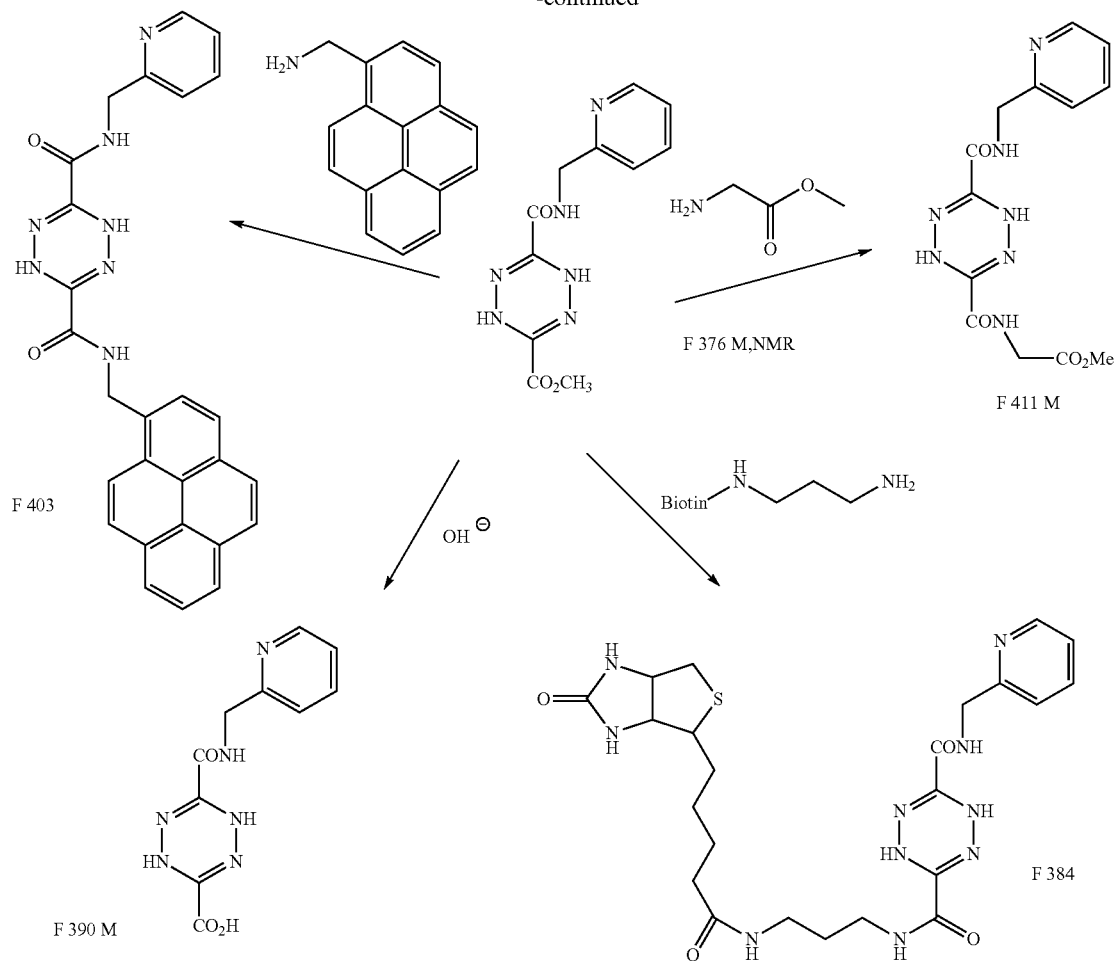
Bis-trifluoromethyl diaryl tetrazine monocarboxylic acids
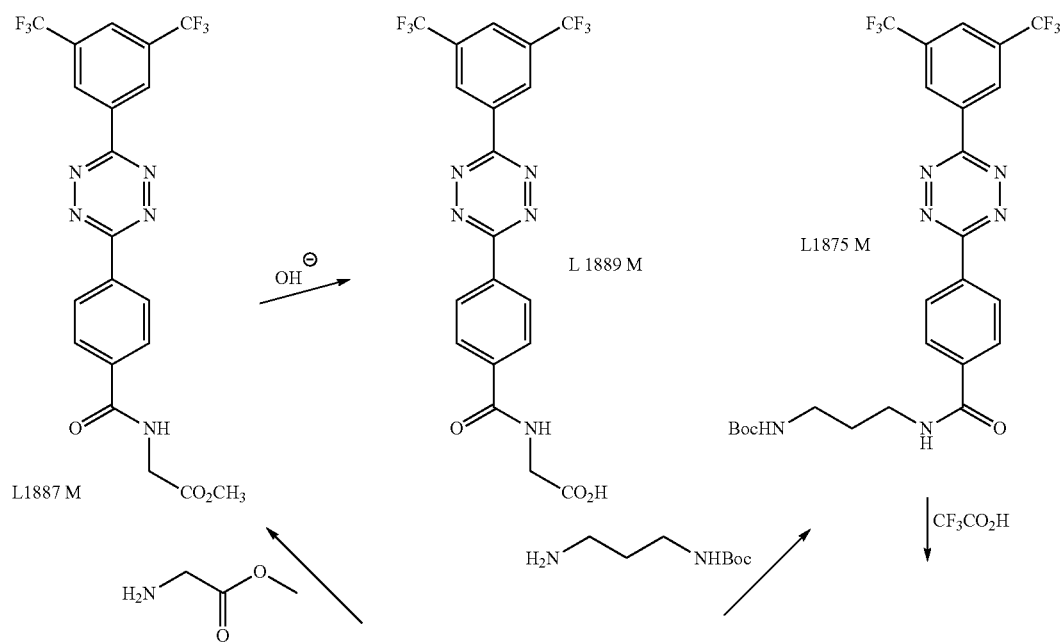

27
-continued
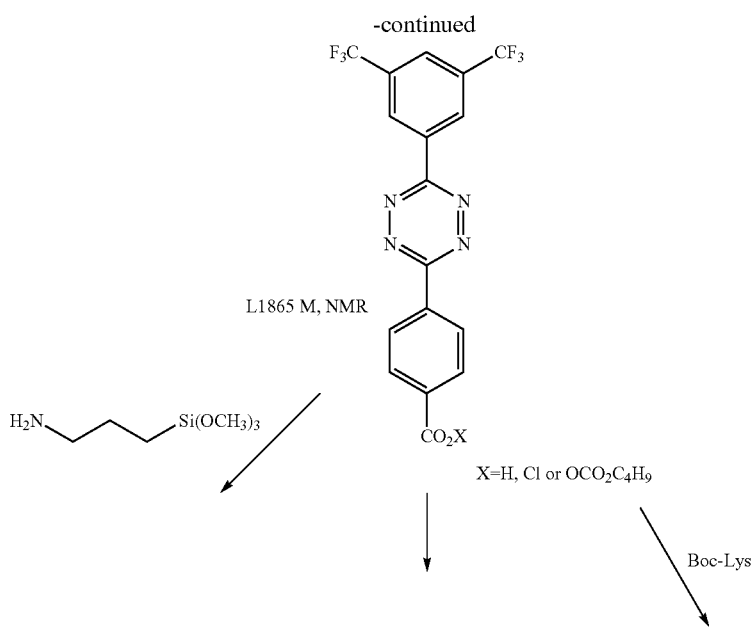
28
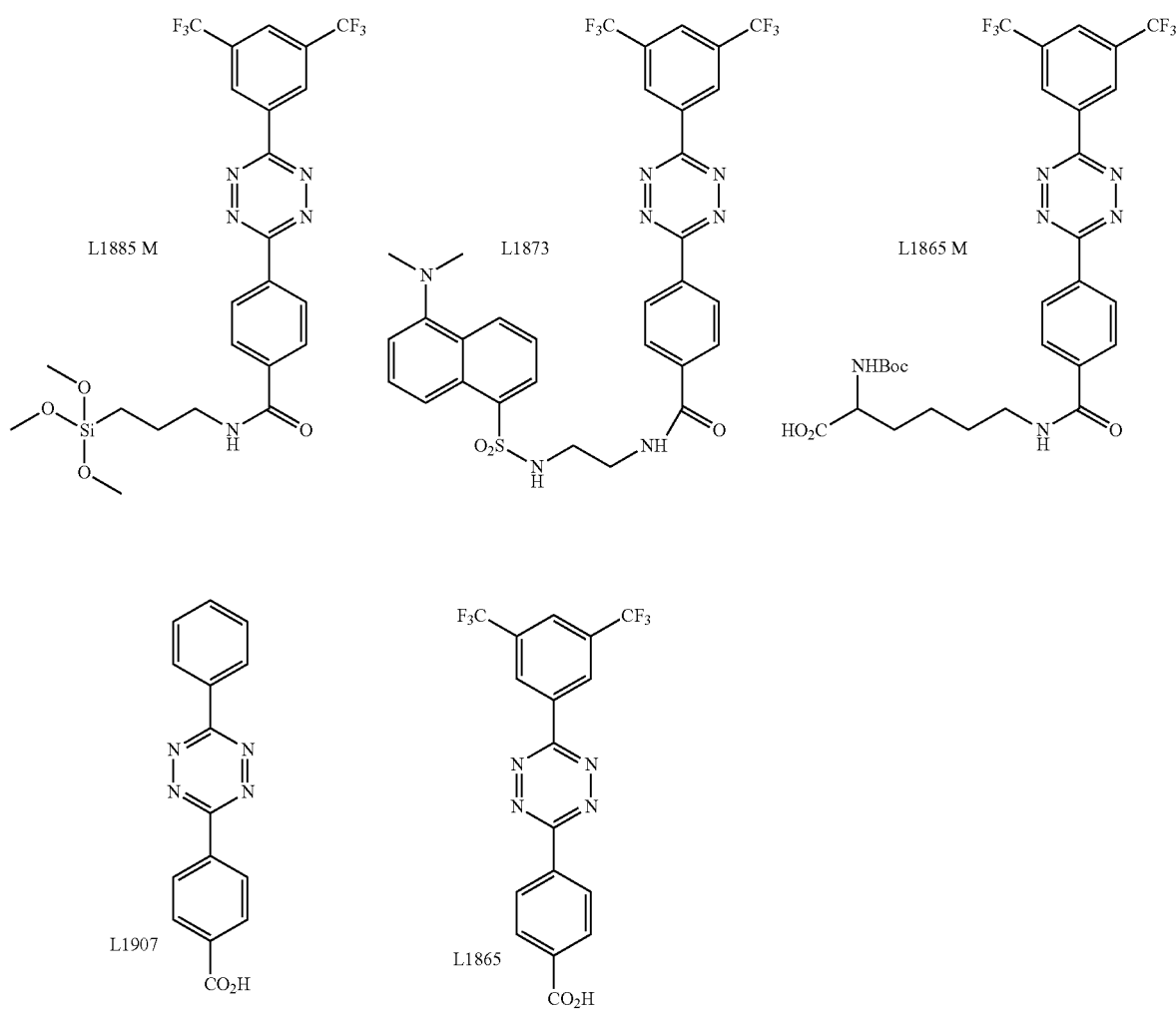

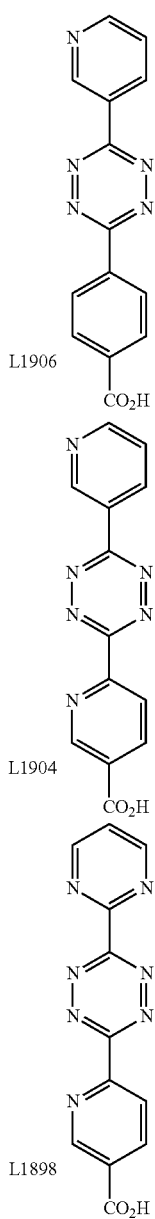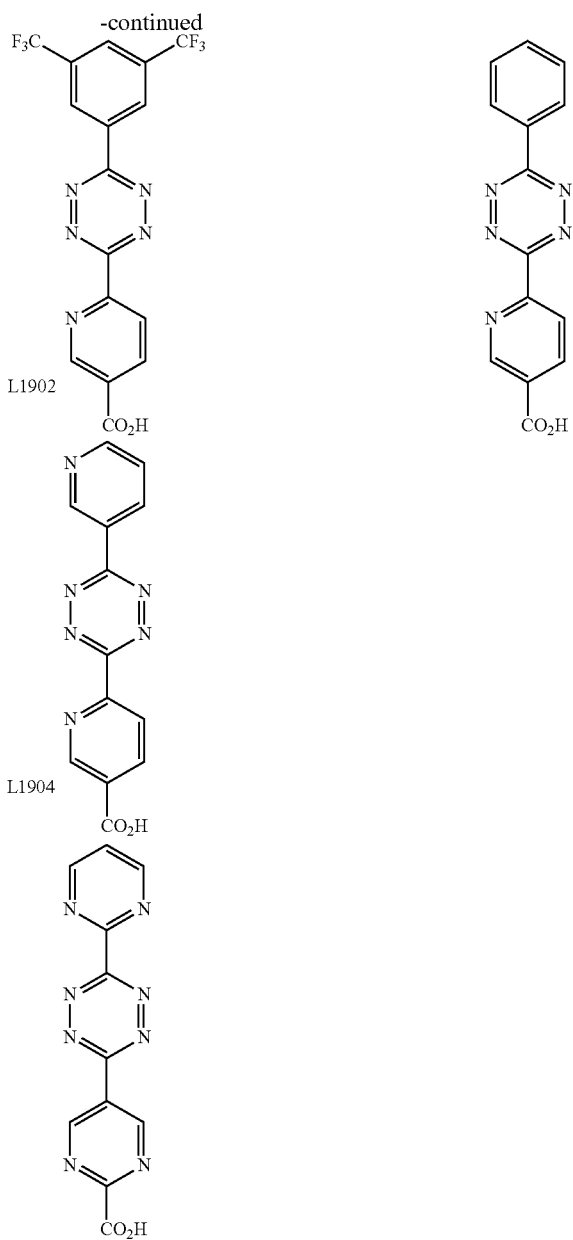

Along with the tetrazines with ester functions, many tetrazines having aromatic residues are known in the literature. With respect to the tetrazine dicarboxylic acid dimethyl ester, they have a reduced diene activity accompanied by a simultaneous marked increase in stability. The greater stability also permits reactions with nucleophiles without the tetrazine ring being destroyed. Methods are available to produce asymmetrically substituted compounds. The introduction of electron-attracting substituents, such as fluorine, trifluoromethyl or heteroatoms into the phenyl rings increases the diene activity. Here, the use of pyrimidine residues has proven extremely successful. In the presence of two pyrimidine residues, the monocarboxylic acid amides derived therefrom reach the diene reactivity of the tetrazine-3,6-dicarboxylic acid ester. The removal of only one nitrogen atom results in a marked loss of the diene reactivity so that a rate range with at least a factor of 10000 is covered by this series of diaryl monocarboxylic acids. Here, the target is also the simple preparation of monofunctional compounds for the incorporation into peptides, oligonucleotides or their anchorage to surfaces. Although methods for the preparation of such tetrazines are known in the literature, monocarboxylic acids of this type have not yet been described in the literature. The simplest preparation of aromatic asymmetric compounds consists of the reaction of two amidines or imidoesters with hydrazine or two nitriles with sulfur and hydrazine or also with hydrazine alone. This simple synthesis route which is also feasible by the use of inexpensive starting compounds is nevertheless unsatisfactory from the view-point of yield. There is the interesting observation that the dicarboxylic acids accessible in very good yields by the same synthesis route can be thermally decarboxylated to give monocarboxylic acids. The monocarboxylic acids poorly soluble in water of this type can be rendered better soluble by conversion into the corresponding N oxides. The introduction of hydrophilic residues is also feasible for this purpose.

Triazines

In contrast to the tetrazines, triazines have a markedly lower reactivity than dienes. However, the chemical stability is markedly better and is at the order of normal organic compounds. Here, the triazine tricarboxylic acid triethyl ester has turned out to be a model compound. Along with the lower reactivity, the formation of isomeric products in the DARinv has proved to be a drawback of triazines. Two problems have to be faced: on the one hand, the increase in the reactivity as diene and, on the other hand, the preparation of defined monosubstituted compounds. Both necessities can be achieved by the selective replacement of the ester groups with trihalogenmethyl groups, preferably trifluoromethyl groups. The nucleophilic substitution at the ester groups of the triazines by amines can be carried out as easily as with the tetrazines. On account of the lower reactivity differences, however, a clear monosubstitution is not so easy. It can be achieved by the use of tert-butyl esters in components so as to yield two ester groups of different reactivity in the triazine. The objective here is also the introduction of functional groups, such as carboxy, hydroxy and amino, via the nucleophilic substitution with amines. Then, reporter molecules, therapeutic agents, peptides or oligonucleotides can be introduced via these functions, as done in the tetrazines or dihydrotetrazines.

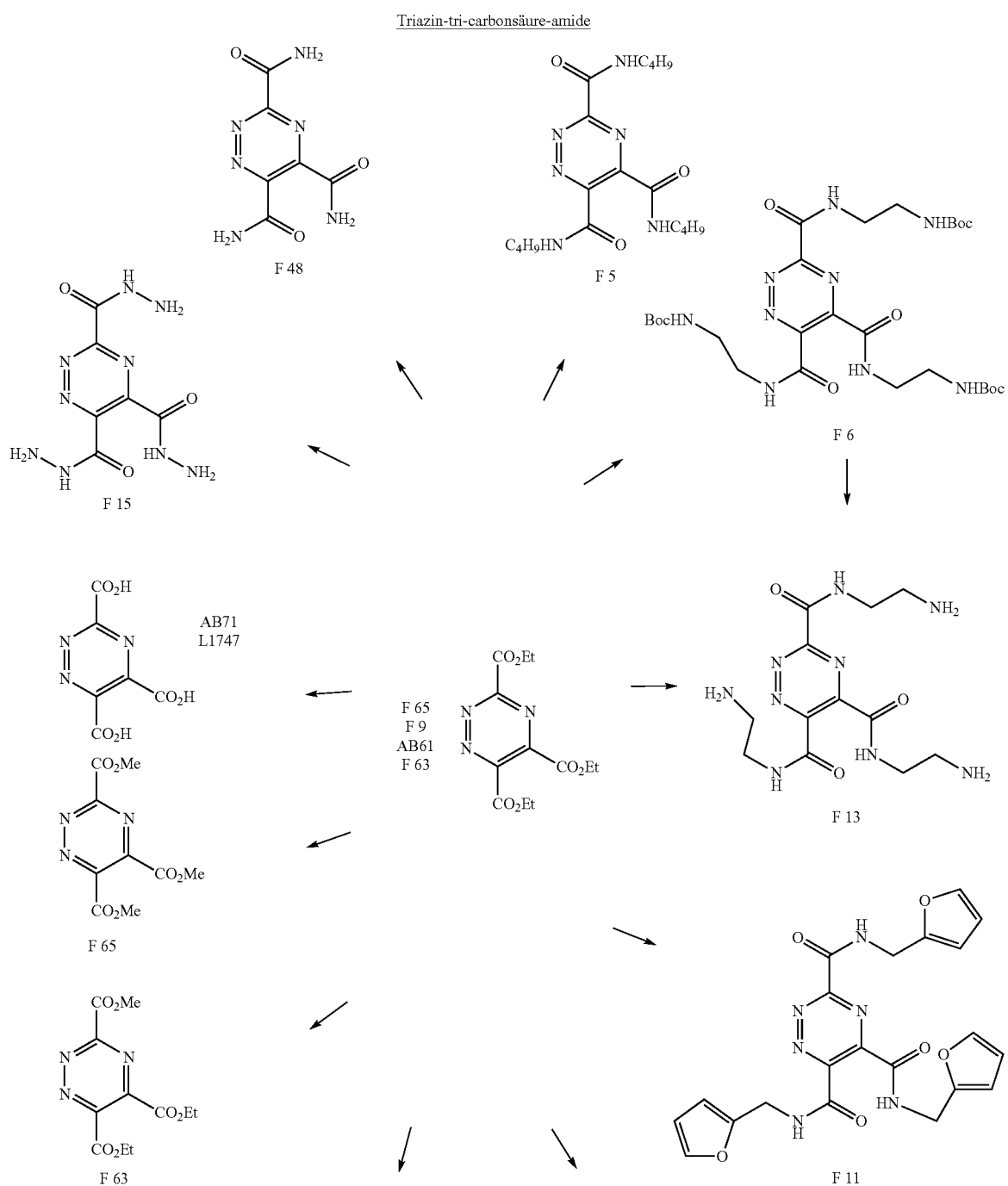

Triazin-tri-carbonsäure-amide

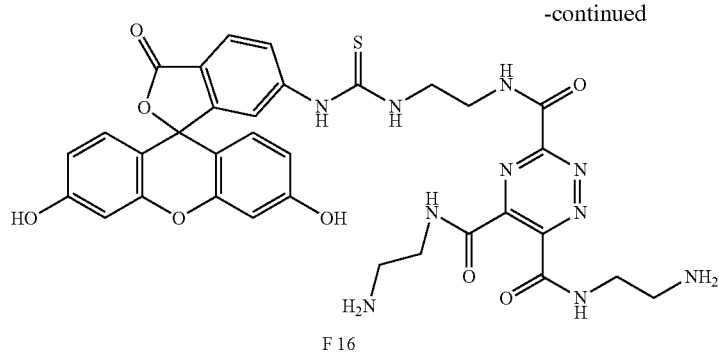

F 16

F 28

A preferred triazine is also the 3-carboxymethyl-5,6-bis-trifluoromethyl-triazine 1,2,4 prepared for the first time. This triazine only has one function via which a number of reactive groups can be introduced which are suited for the aspired intended use. As a result of the two adjacent trifluoromethyl groups, these triazines tend to form hydrates, a property many triazines are known to have. This hydrate formation can reduce inter alia the activity as a diene in the DARinv, yet the DARinv takes place.

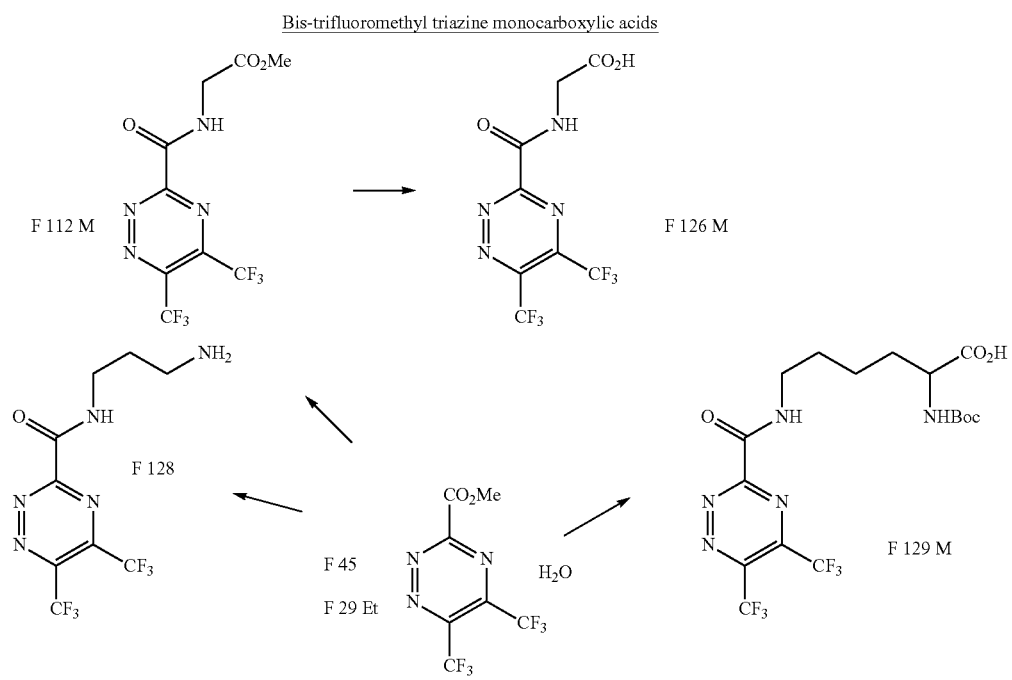

Bis-trifluoromethyl triazine monocarboxylic acids

-continued
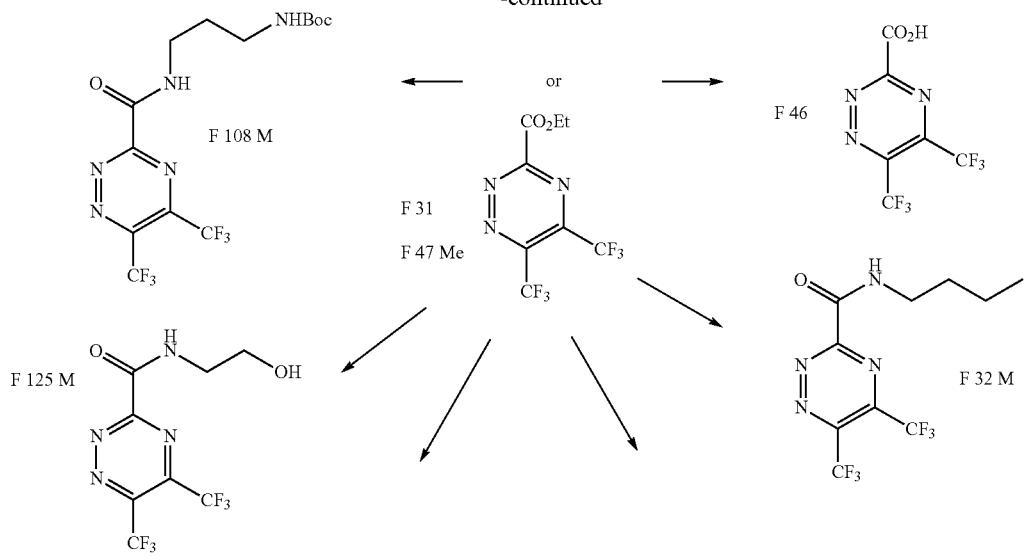
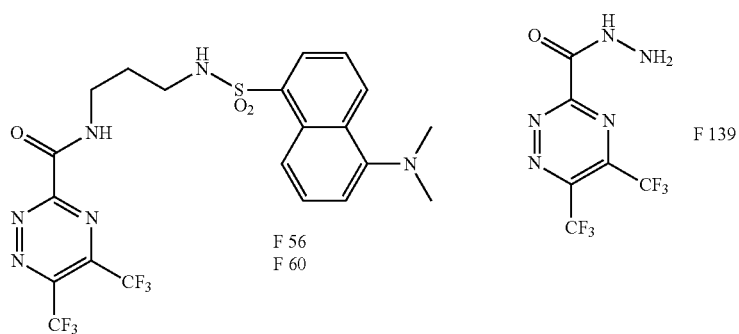
Mono-trifluoromethyltriazinedicarboxylic acid ester
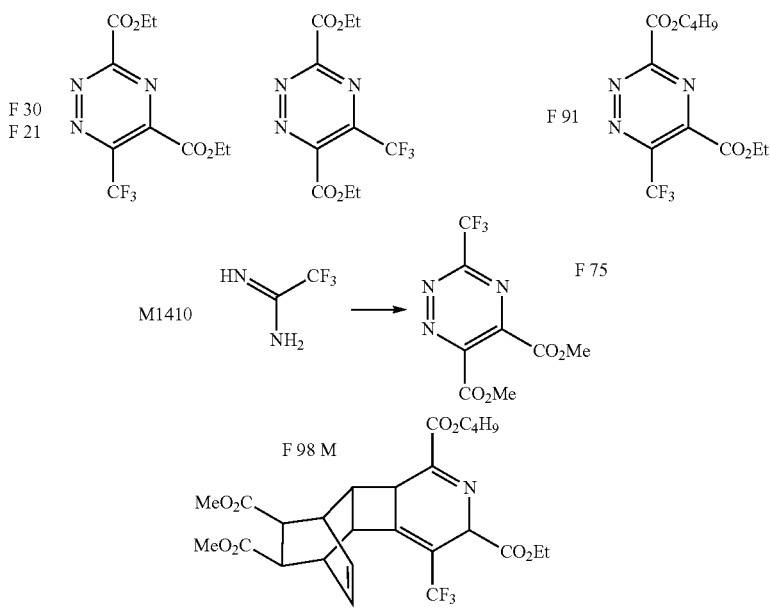

The introduction of only one trifluoromethyl group into the triazine ring already suffices to obtain a sufficient diene activity.

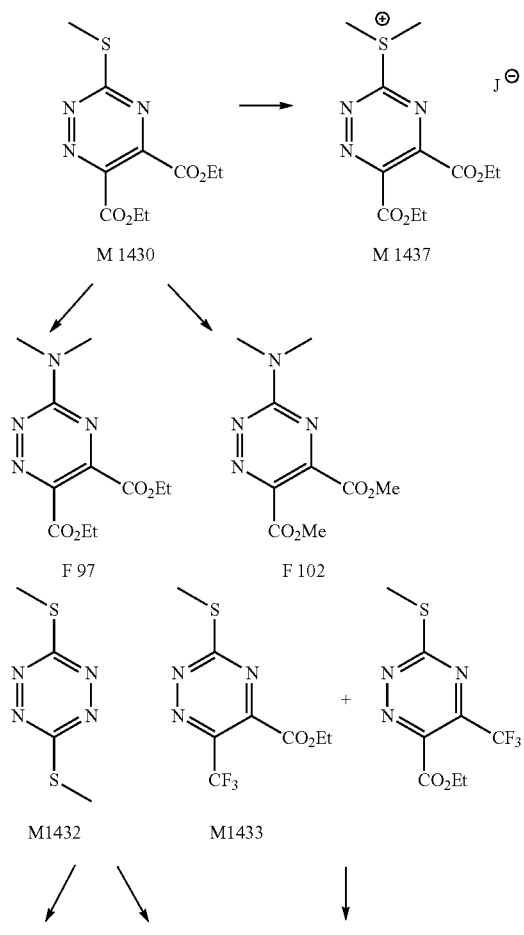

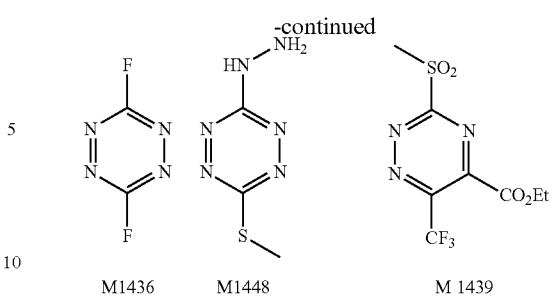

Diazines

Dihydrodiazines, from which it is easily possible to obtain diazines by means of oxidation, form by the DARinv of tetrazines with a dienophile. When the dienophile is an enamine or a substituted acetylene, the diazines form directly.

Preparation of Dienophiles

Dienophiles I

A number of known cyclic and bicyclic unsaturated anhydrides of different ring size can be reacted without any problems with substituted amines to give the corresponding acid imides. Here, reference is to be made explicitly to the exo- and endo-norbornene dicarboxylic acid anhydrides both of which can be purchased. Monocarboxylic acids, such as the cyclopentene carboxylic acid, can be linked to the amino acids or diamine ligands via their acid chlorides. The derivatives of the allylacetic acid can be prepared in the same way. They can then be covalently bound to a tetrazine carrying molecule, also to a surface, by the DARinv. The reactions with Boc or Fmoc lysine supply peptide building blocks which can be incorporated selectively at any positions into peptides. When dienophiles of different reactivity are incorporated into the same peptide chain, these peptides can be labelled several times in a selective way. The same also applies to oligonucleotides.

NORBORNENE IMIDES

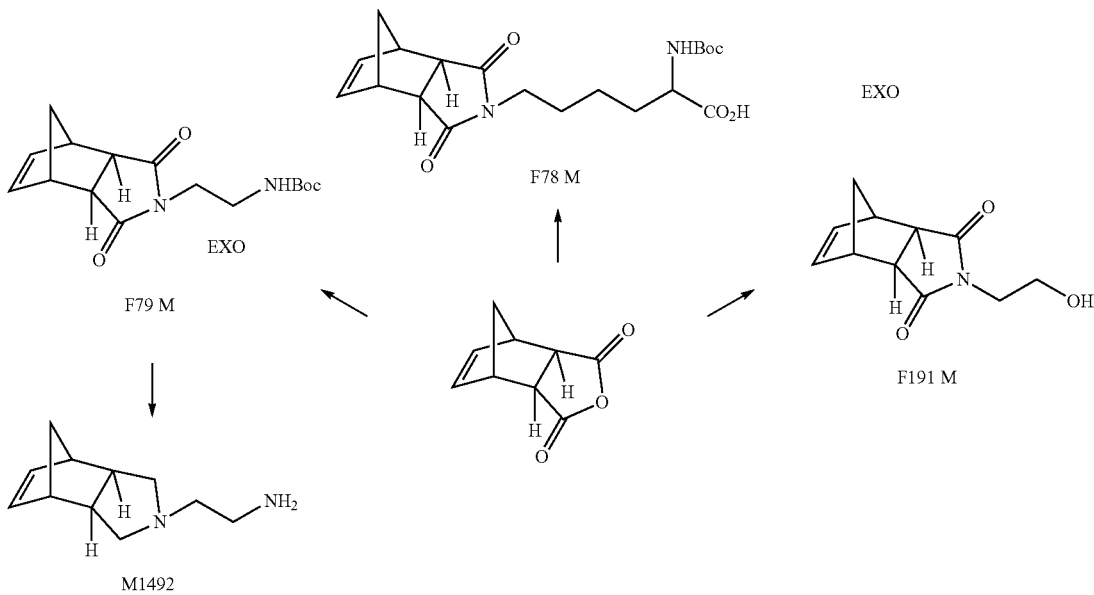

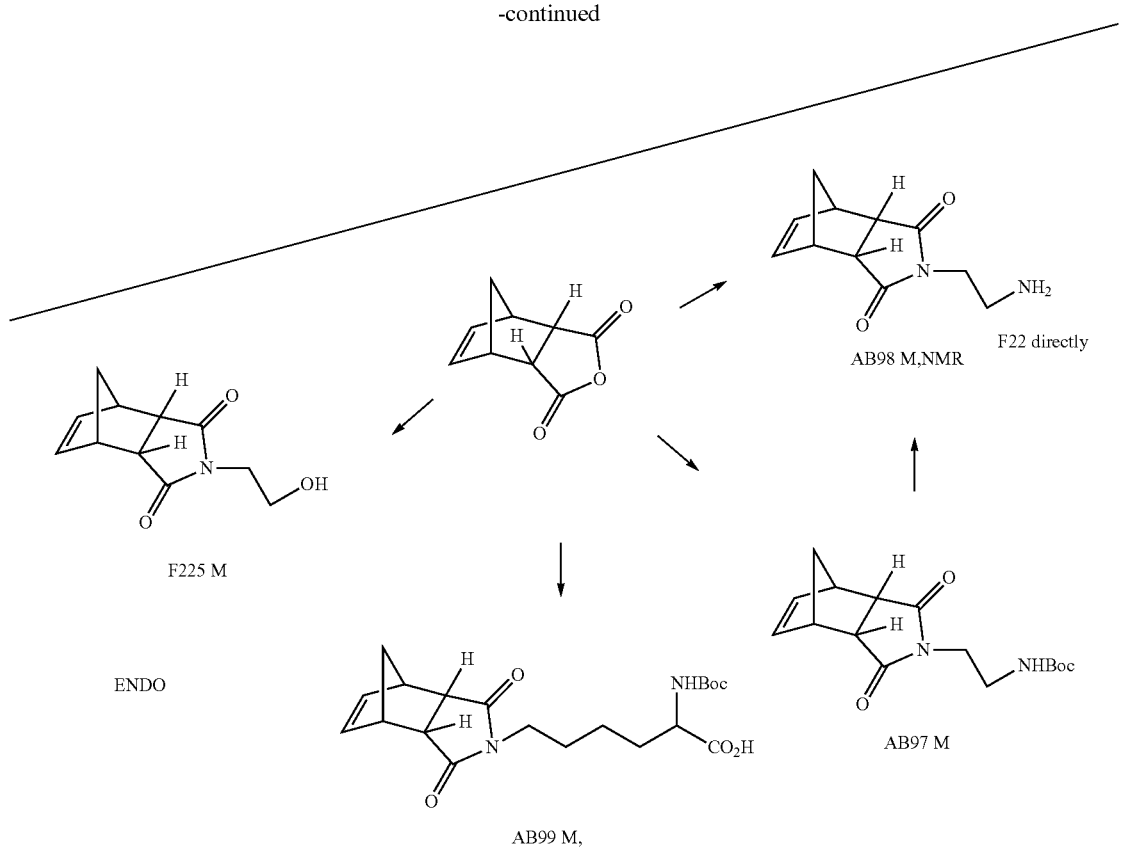
These reactions can be transferred to the exo-norbornene dicarboxylic acid anhydride, the cyclobutene dicarboxylic acid anhydride and the cyclohexene dicarboxylic acid anhydride or any other anhydrides which contain a strained or a terminal double bond.
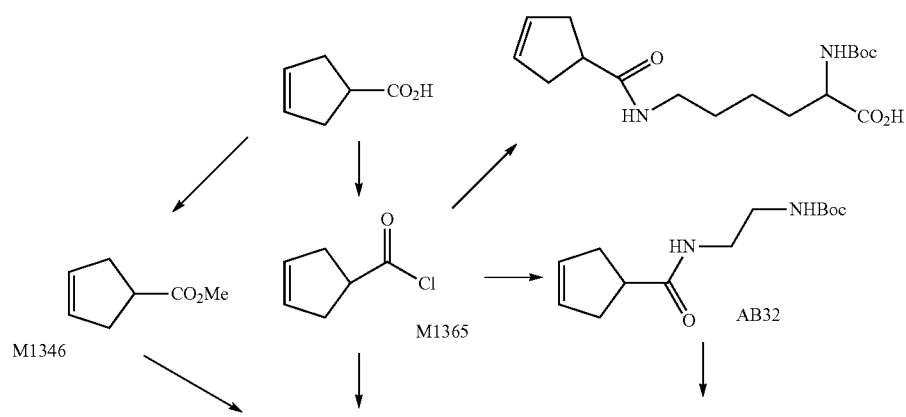

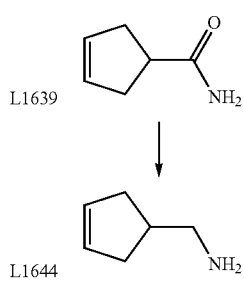
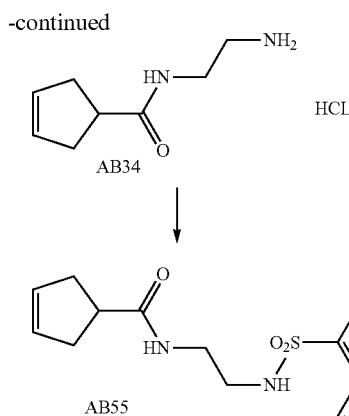
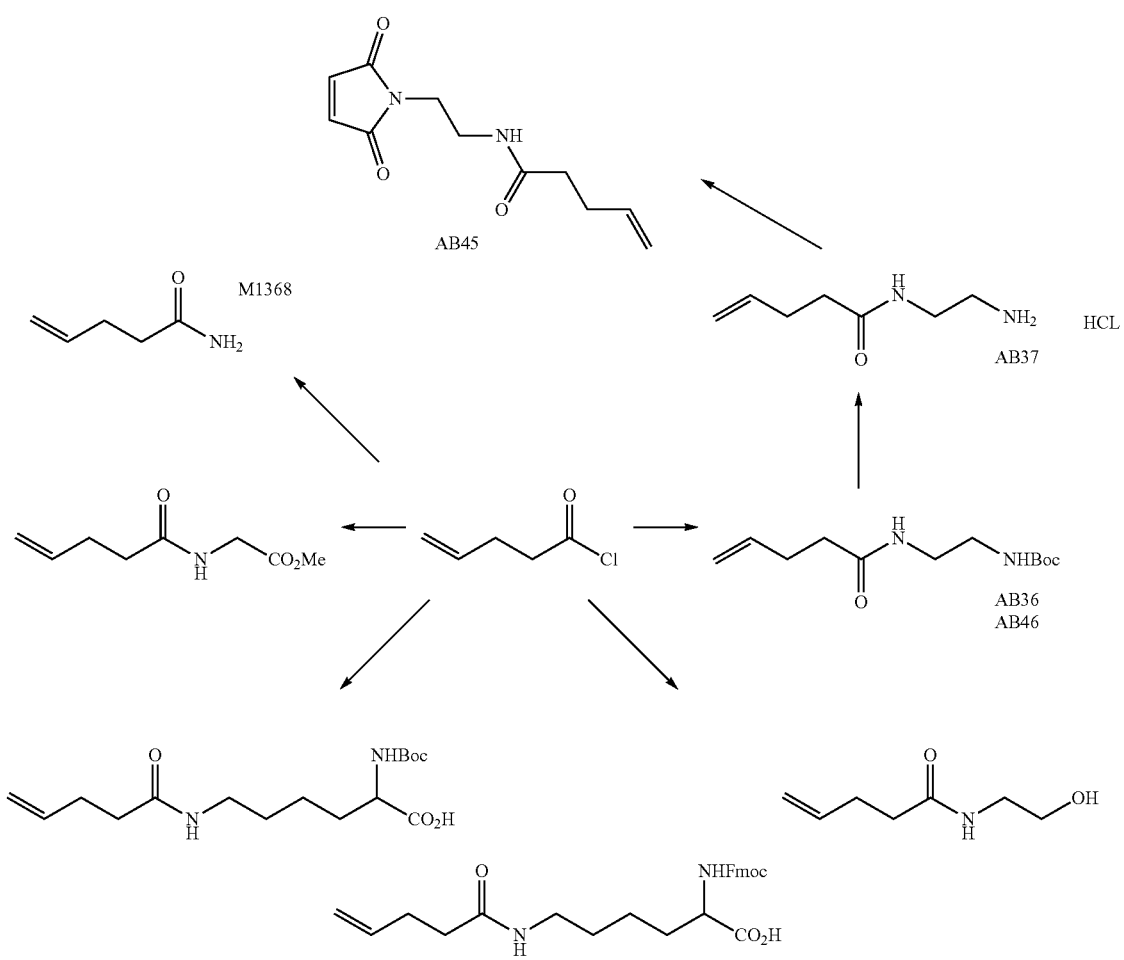

Dienophiles II

A special case is the tricyclic anhydride readily accessible from cyclooctatetraene, abbreviated as COT, and MSA. The DAR of the bicyclic form of COT leads to a molecule containing two differently reactive dienophiles for the DARinv. As usual, further functions can be introduced via the anhydride ring, such as amino acids, amines or the coupling to a solid phase.

However, only the highly reactive cyclobutene ring is available for the DARinv. The cyclohexene ring already less reactive as such cannot be reacted in this tricycle as a dienophile, i.e. a behavior that is due to the endo arrangement of the anhydride ring. This behavior was already discussed in connection with the cyclobutene dicarboxylic acid anhydride. When the carbonyl groups are removed by reduction, the resulting amine enters into the double DARinv with reactive dienes. The DARinv only takes place with a cyclobutene ring when a diene is less reactive. When a more reactive diene is added, the cyclohexene ring reacts as well. Thus, two completely different molecules which carry tetrazines of different diene activity as anchor groups, can selectively be linked with each other in predetermined way.

Dienophiles on the basis of cyclobutenes
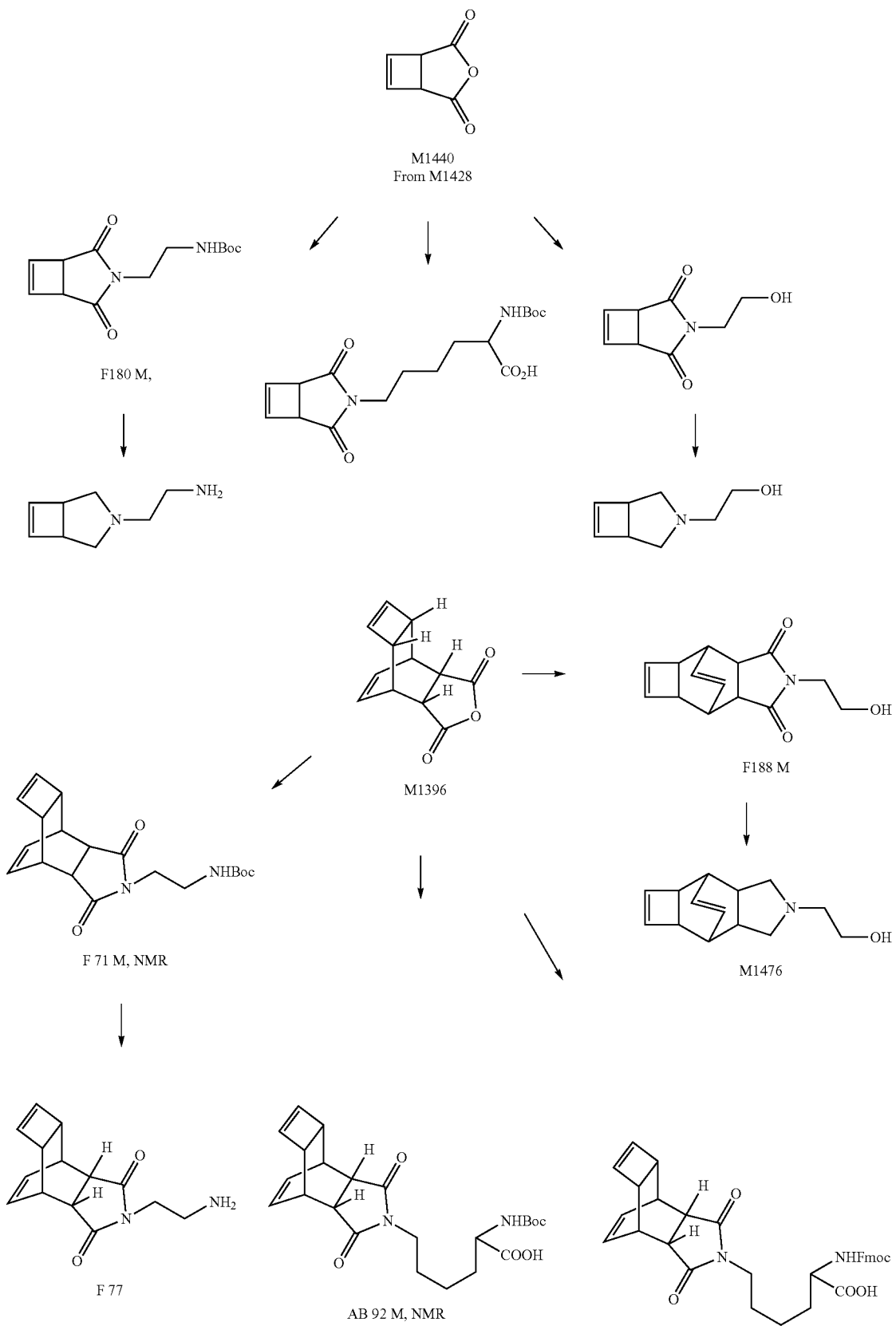

The below amino acids can be purchased and all three react as dienophiles in the DARinv. The three amino acids can be introduced at any position during the peptide synthesis and new residues can then be introduced at these positions via the DARinv; also, such peptides can be anchored to surfaces for detailed structural analyses in defined way. The enzymatic peptide synthesis also permits the introduction of amino acids with dienophilic anchor groups as shown by the Bertozzi group.

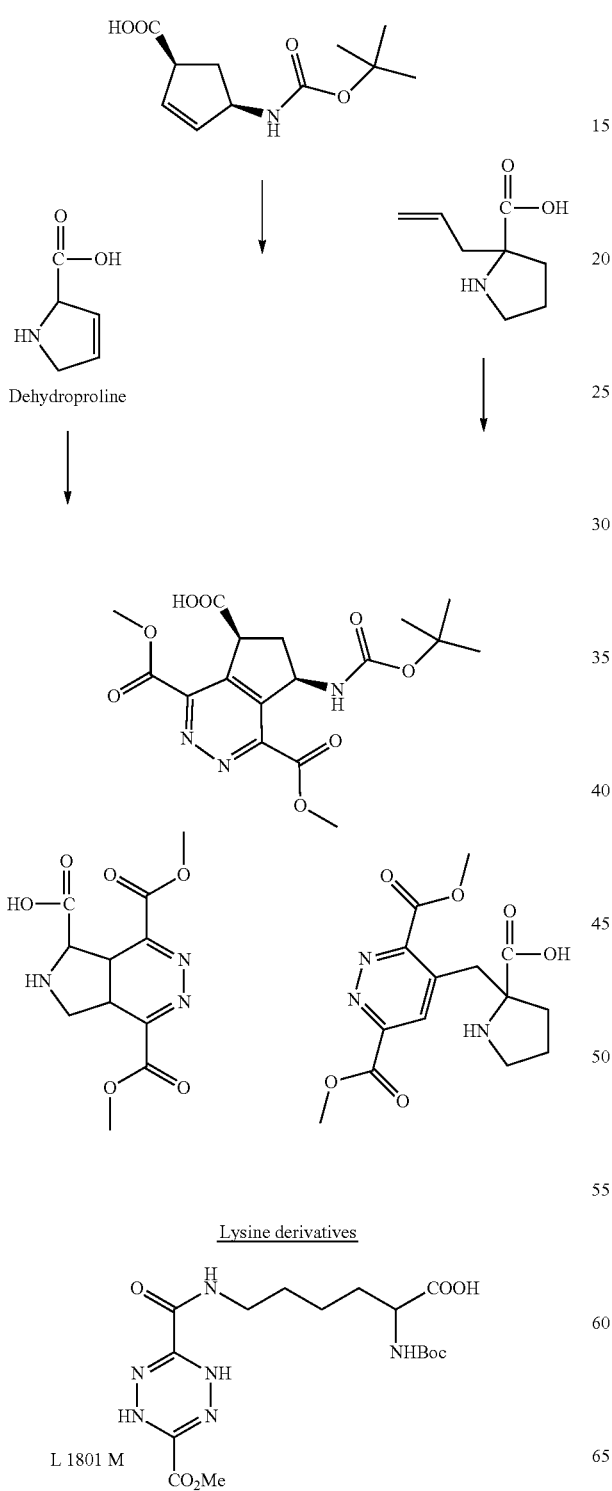

Lysine derivatives

-continued

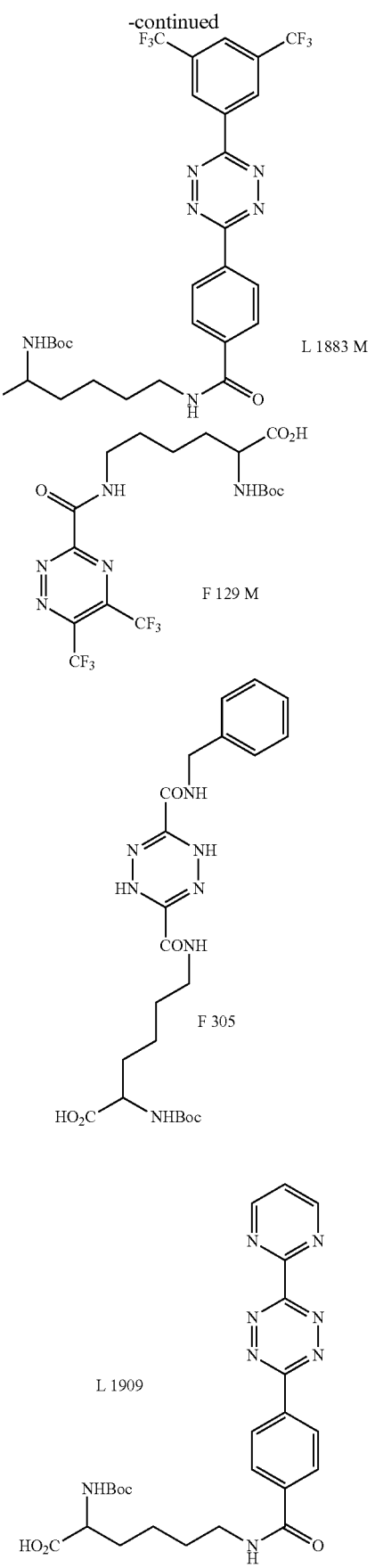

-continued

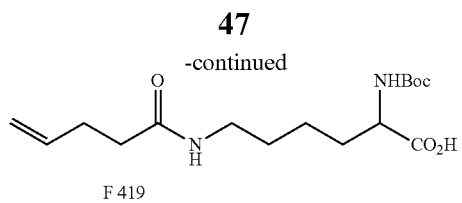

F 419

Fmoc lysines

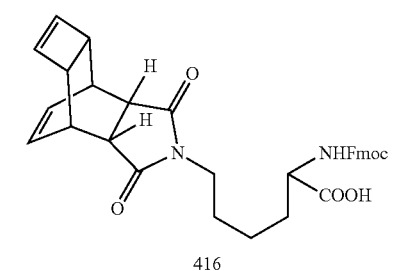

416

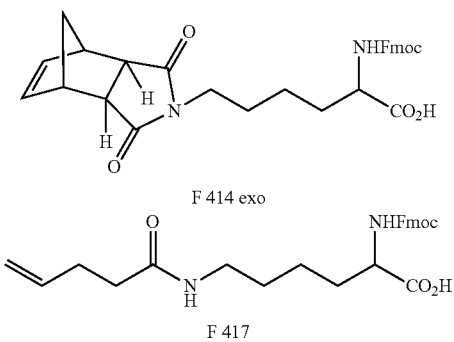

F 414 exo

F 417

F 415 endo

-continued

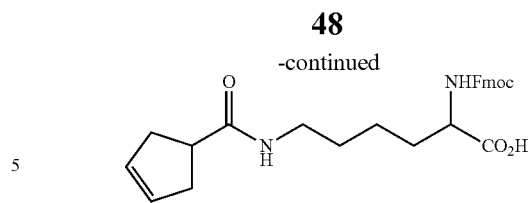

F 425

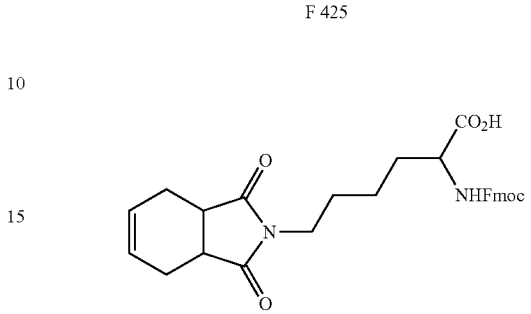

The building blocks prepared by the inventors for the peptide synthesis are summarized above. The reverse principle, namely the incorporation of the diene into the peptide can also be carried out on the solid phase. The last amino acid coupled is a lysine which is substituted at the amino group by a tetrazine. Following cleavage from the solid phase, the peptide can be isolated as a pink solid. The reaction with the COT-Lys-EILDV peptide results in a coupled dipeptide. The same peptide is isolated when the DARinv is immediately carried out on the solid phase. The incorporation of lysine building blocks of the dihydrotetrazine diamides into peptides is also possible, followed by the oxidation to give tetrazine. This procedure is useful when the tetrazine decomposes under the conditions of peptide synthesis. Hence it is shown that the coupling of biomolecules is possible by means of the DARinv and can be varied in many ways.

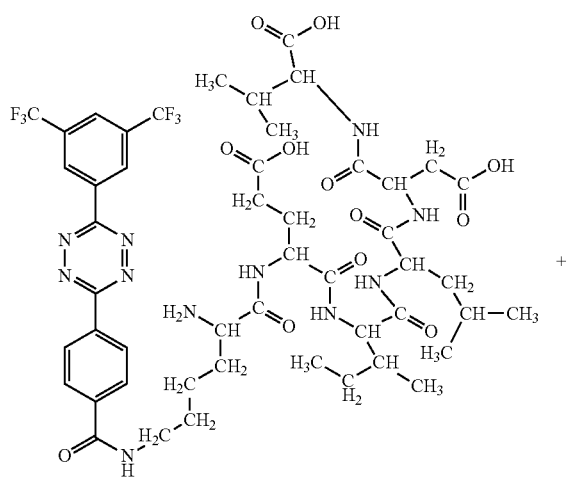

+

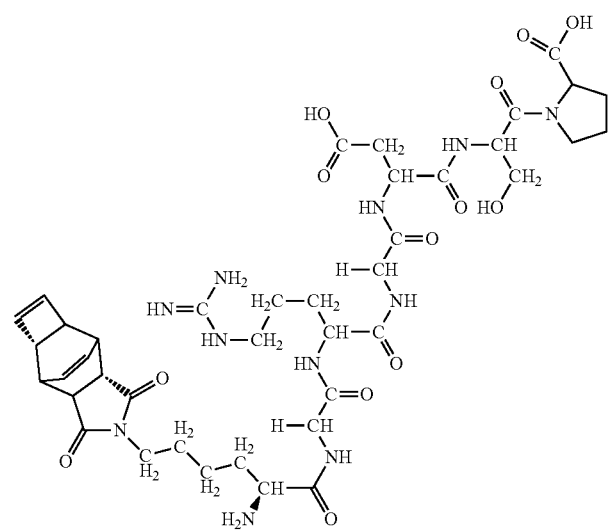

↓

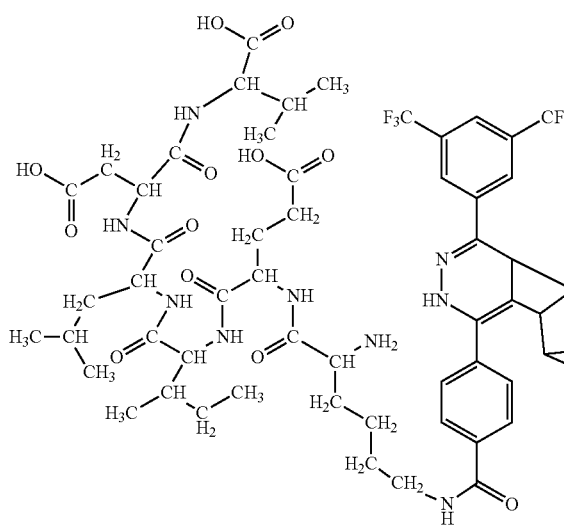
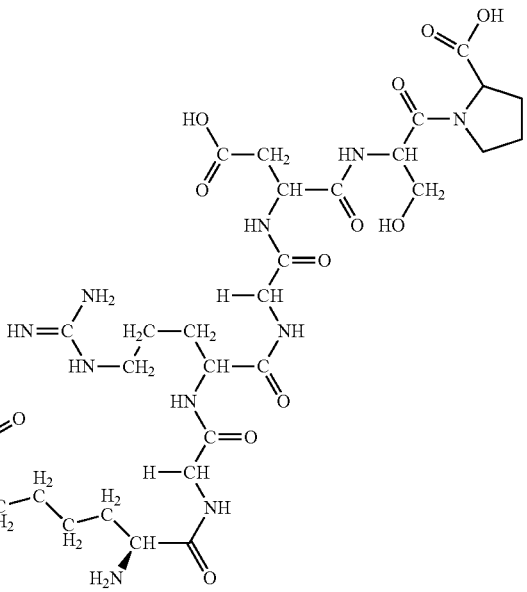
The peptides can also be labeled with dyes or biotin on the solid phase or after cleavage by the DARinv.
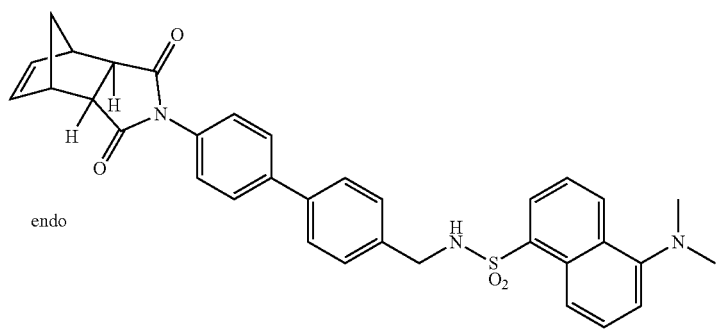
F214
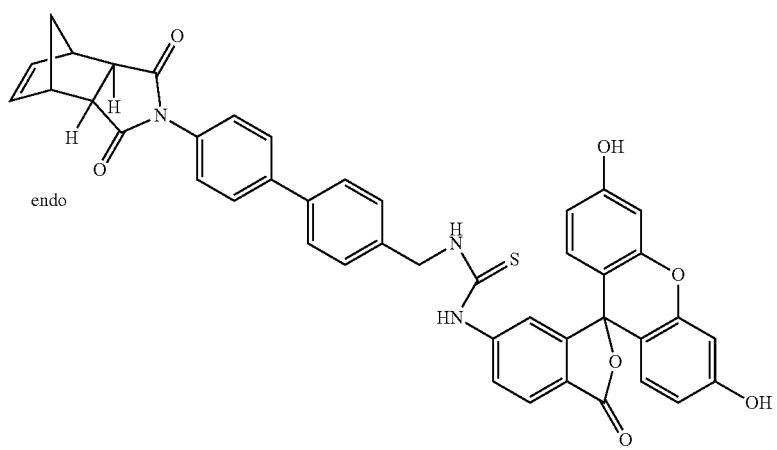
F220

51  52
-continued
F100
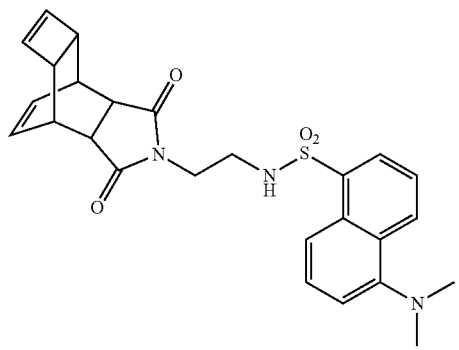
L1873
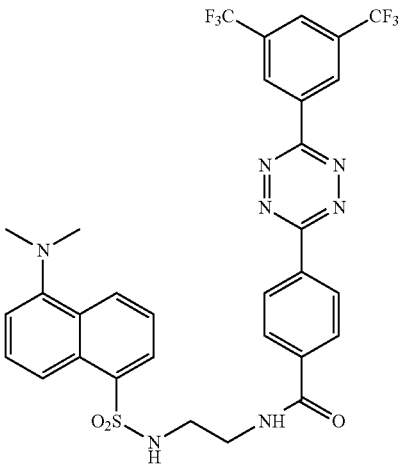
L1920
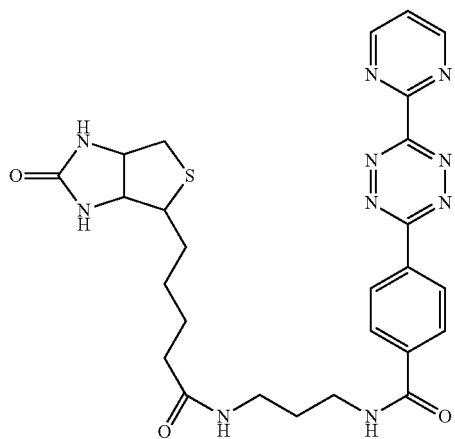
F 82
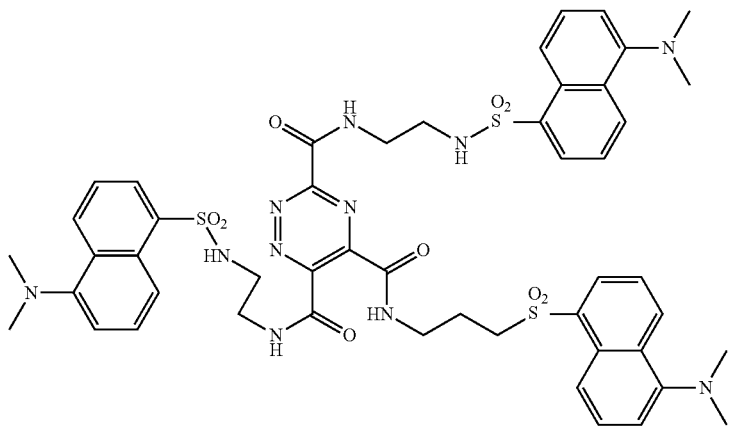
F 109
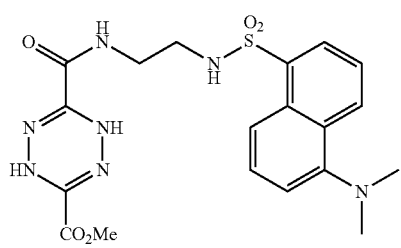

A sequential double DARinv is shown below which proceeds with two differently reactive tetrazines at the bifunctional dienophile.
Sequential DARinv of M 1476
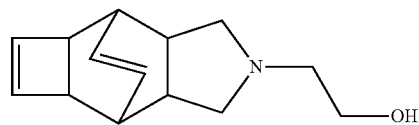
M 1476
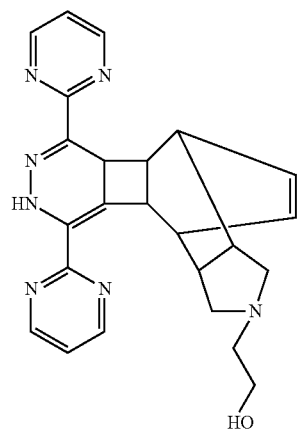
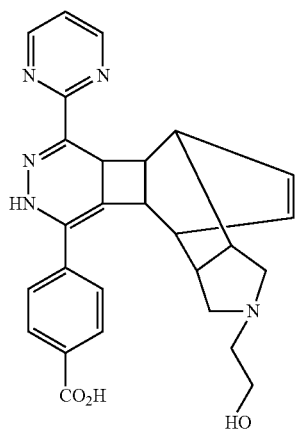
F 466
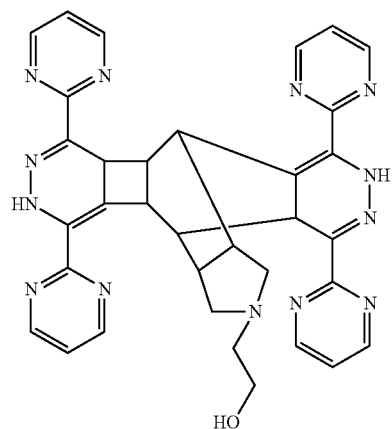
F 464
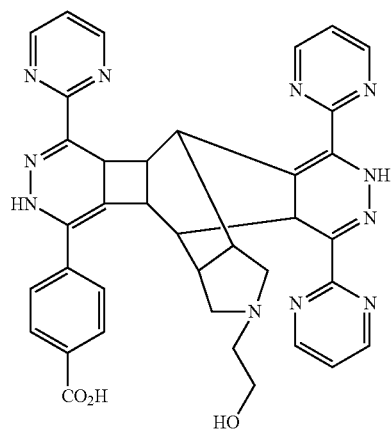
F 470

All compounds which have a terminal double bond react as dienophiles in the DARinv. Reactions with purchasable compounds are listed below. They include allyl malonic ester, allyl galactose, and allyl silsesquioxan.

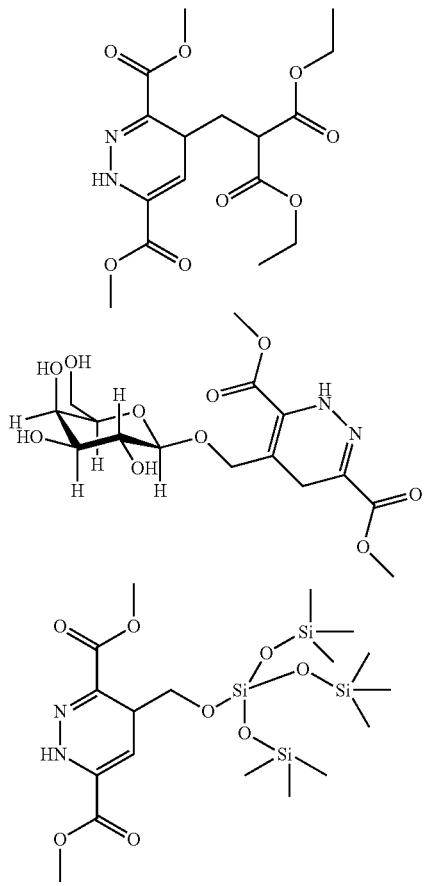

The field of application of the ligation technology based on DARinv ranges from the functionalization of surfaces in the area of nanomaterials to the labeling of biopolymers with dyes or other reporter molecules. It also comprises the linkage of therapeutic agents with biopolymers on the basis of drug targeting, the linkage of proteins with saccharides to improve the pharmacokinetic parameters. Some applications are described in detail below.

Applications I Platinum Complexes

It is the object to produce platinum complexes where either the diamine ligand or the dicarboxylic acids used as a leaving group are formed as a dienophile or diene. The below listed structures shall elucidate this concept. It thus becomes possible to selectively modify the respective part of the complex by the DARinv. As a result, the establishment of libraries of the original complex becomes possible. The modification of the leaving group, here the dicarboxylic acid, by the DARinv appears to be particularly interesting since this leaving group is split off during the intracellular activation of the Pt complexes and thus also the particular part attached by the DARinv. Thus, the leaving group can be selectively modified by the DARinv, e.g. by peptidic signal sequences or other biomolecules which can convey a preferred incorporation of these complexes into tumor cells. Following the covalent bond of the active platinum complex to the DNA, the development of the diamine ligand as dienophile permits the localization of the resulting adduct by a DARinv to be proven by a reporter molecule. Of course, it is also possible to give both the amine ligand and the leaving groups as dienophiles having different dienophile activity, which permits the simultaneous well-calculated ligation of both the amine ligand and the leaving group. In order to make sure that $Pt^{2+}$ does not react with olefinic double bonds during the synthesis, the here shown Pt complexes were prepared.

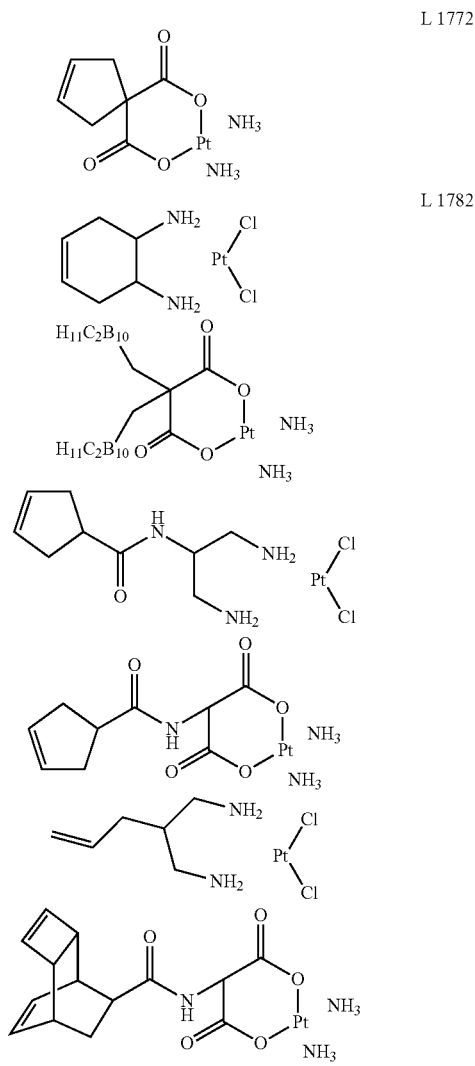

The above listed ligands and leaving groups are known in the literature.

Since the illustrated platin complex of 1,2,3-triaminopropane is known it is possible to bind to the tetrazine via its free amino group so that another building block for the incorporation of Pt complexes into proteins, saccharides and other biomolecules and therapeutic agents is present.

Applications II PET

Positron emission tomography represents a radioactive, non-invasive but very sensitive diagnostic method. The most widely used positron emitter is F18, which decays into the element oxygen with a half-life of 18 min thereby releasing a positron. Due to the short half-life, the preparation of suitable F18-labeled compounds requires special synthesis methods. They have to proceed rapidly and necessary purification methods must be simple. The compound most frequently used for the time being is 2-fluoro18-2-deoxy-glucose. The ligation reaction based on the DARinv can very well be used for labelling peptides, oligonucleotides and saccharides with F18. Nucleophilic substitution reactions on aromatic compounds are facilitated when the number of nitrogen atoms in the ring increases, e.g. in the series benzene, pyridine, pyrimidine and triazine. For example, a thiomethyl residue can very easily be replaced in 1,2,4-triazine by a number of nucleophiles, also by halogens. Since such triazines react as dienes in the DARinv, the previous introduction of F18 into such a triazine offers an elegant possibility of labeling the above mentioned biopolymers by means of the DARinv with F18 thus making them accessible to the detection by PET. However, the classical route via the nucleophilic substitution on tosylates with fluoride is also possible (see below).

Substances for PET

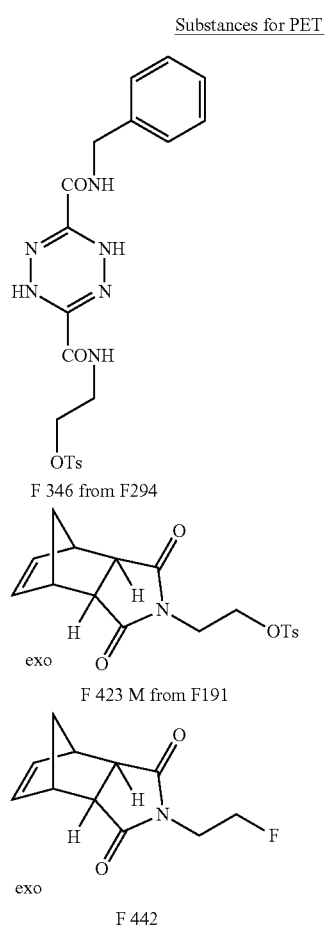

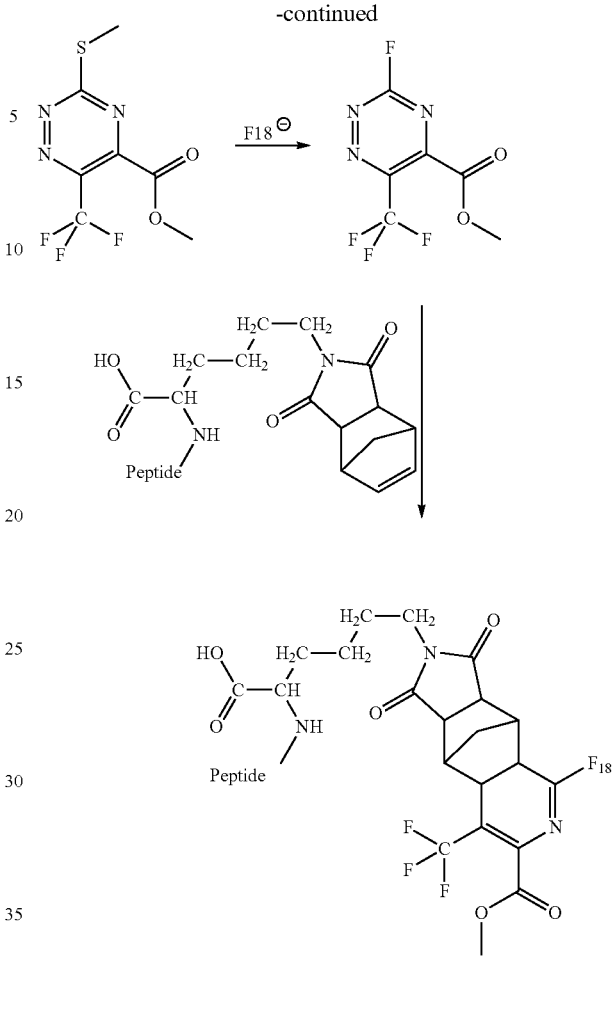

The introduction of trifluoroacetyl groups, which are F18 labeled, via the amine function of the described tetrazines and triazines can be used here. Thus, the tetrazine can be trifluoroacetylated in pyridine and the DARinv can be carried out directly in the solution. However, it is also possible to introduce F18 at the stage of dihydrotetrazines and thereafter carry out the oxidation to give the tetrazine. It is important for all these reactions that the DARinv permits very short reaction times and usually proceeds without the formation of by-products.

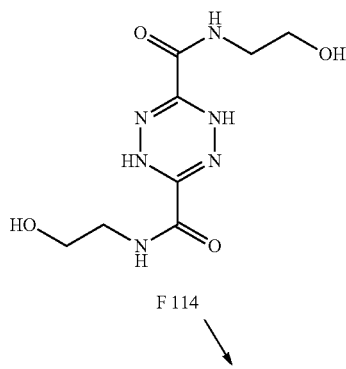

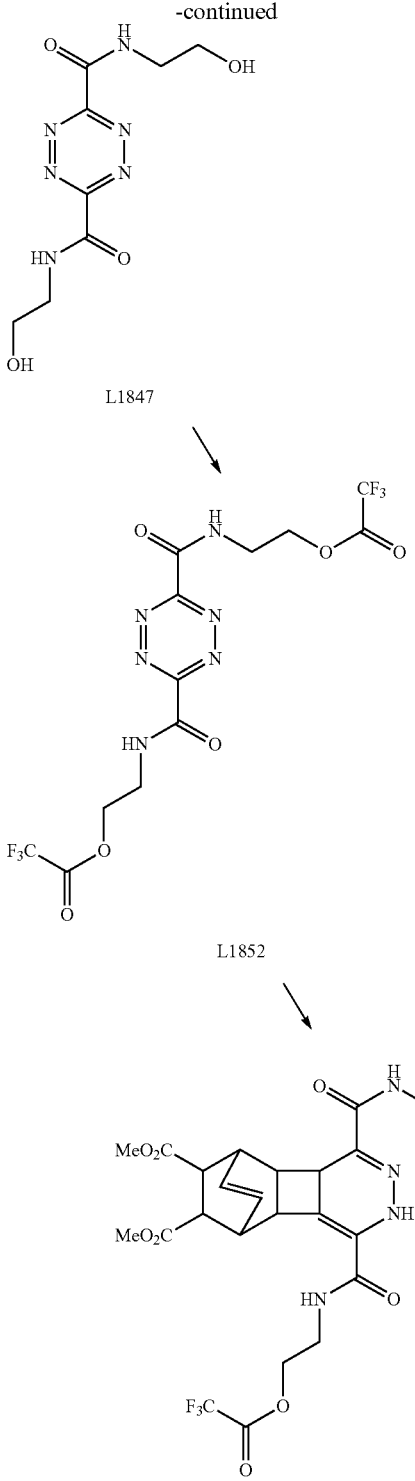

L1847

L1852

Applications III Surfaces

As already described in the preparation of dienes, the dihydro tetrazine dicarboxylic acid ester can be reacted at room temperature with primary amines to give amides. This high reactivity can be used for the synthesis of reactive solid phases. The here shown reaction sequences can be carried out in yields between 70 and 90%. As a result, the solid phases become accessible which carry either a diene or a dienophile for the DARinv. In this connection, the reactivity in the DARinv is high enough for the dienophile-carrying solid phase to be practically titrated with a tetrazine. The applications following therefrom range from the chip technology for oligonucleotides, proteins or saccharides to catalytic surfaces and solid phase reagents. The prepared trimethoxy-silyl compounds can also be used for anchorage to surfaces, both the diene and the dienophile being adapted to be anchored on the surface. However, the acid chlorides of the diaryl tetrazine monocarboxylic acids and the dihydro tetrazine glycinic acid chlorides are also available for this purpose.

61 62
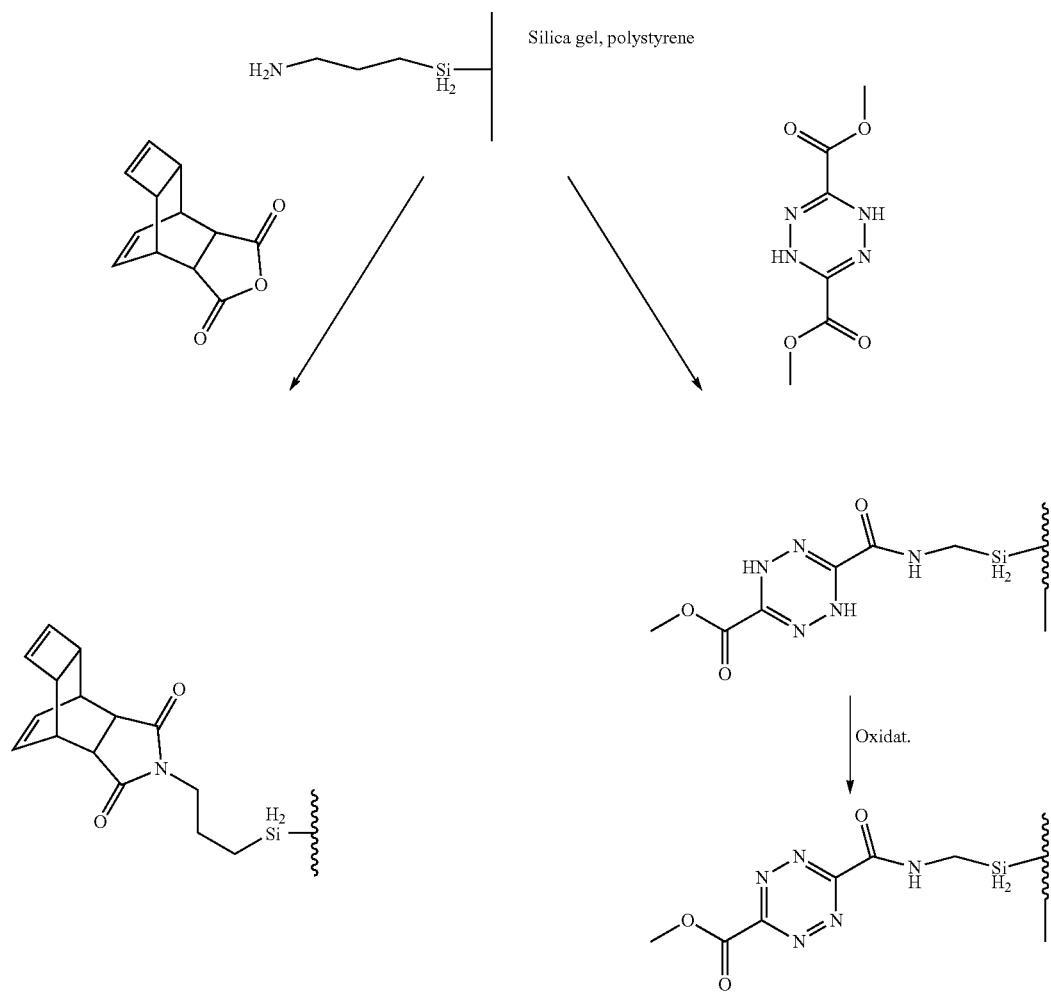
Dienophiles
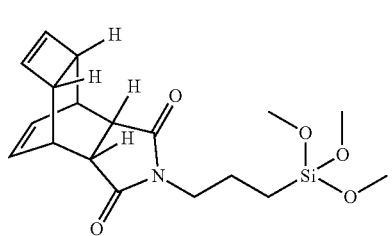
F348 M
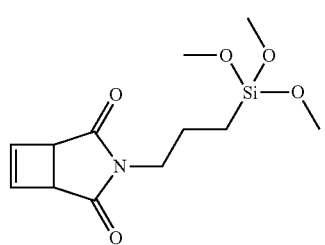
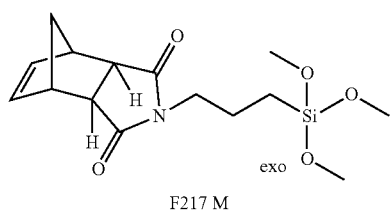
F217 M
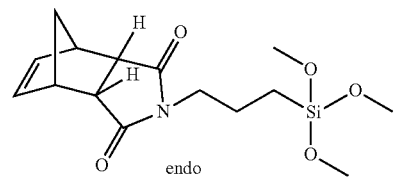
endo Dienes

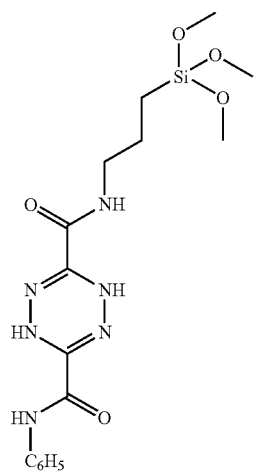

F303

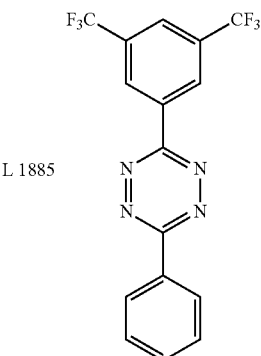

L 1885

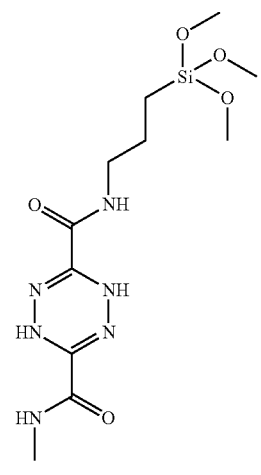

F278

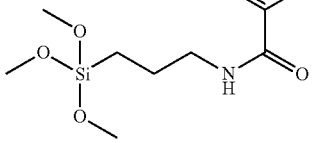

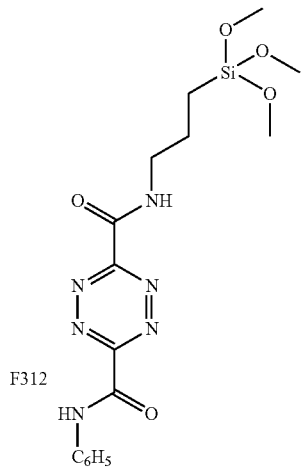

F312

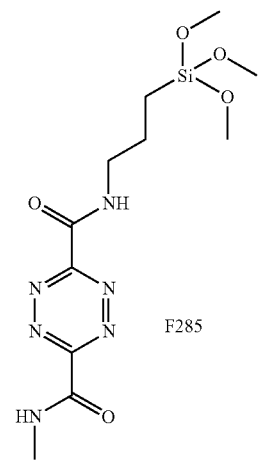

F285

Since the DARinv is a very rapid reaction, it is also possible to covalently connect two surfaces with each other in the sense of an adhesive. Reactions on surfaces usually proceed at a rate lower than that of the reactions in solution. It was observed in connection with the DARinv that the impetus of the reaction is so high that also in those cases in which the tetrazine is poorly soluble, such as in water, the reaction proceeds on the surface of the tetrazine particles under visible nitrogen generation.

Applications IV DNA adducts

The analytical methods of detecting DNA adducts cannot be automated yet. The P32 post-labeling method is still the most sensitive method. However, there is no method available yet which permits the simultaneous detection of different adduct types. Although the method of separation by means of capillary electrophoresis followed by fluorescence detection is very well suited to detect 5-methyl-cytosine, it misses the detection limit of the 32P post-labeling method by at least a factor of 100. Here, the ligation reaction described in the present application can also be used as a remedy. The amine derived from norbornene can be coupled to the phosphate group of the nucleosides by a more recent method according to the literature. Then, any fluorescent dye which is linked with a tetrazine or triazine can be coupled via the DARinv and subsequently be detected by means of the capillary electrophoresis.

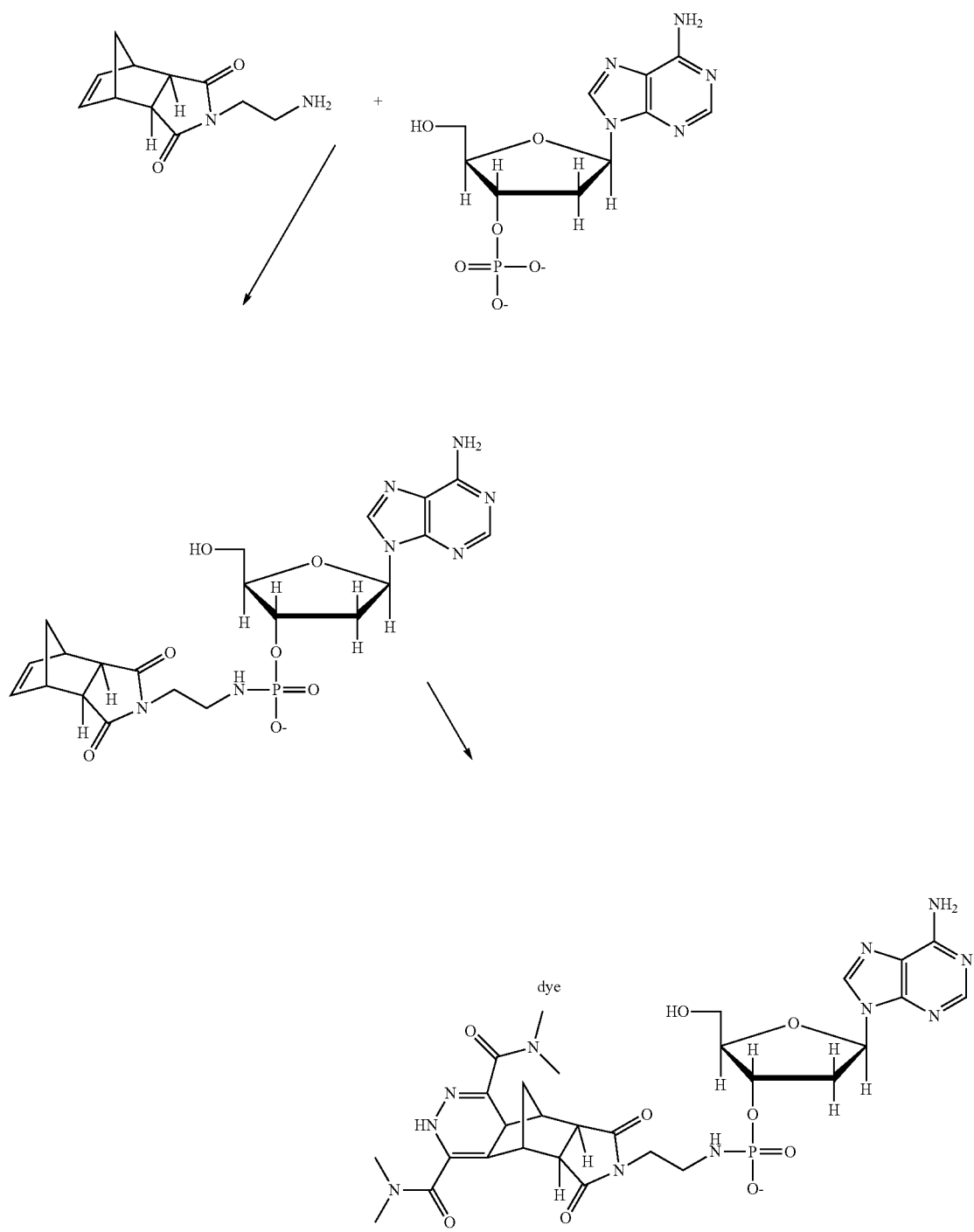

Along with this general method there is the possibility of directly detecting the DNA adducts that structurally contain a DARinv-capable double bond, such as the etheno adducts of dA and dC. These adducts play an important part in the assessment of oxidative stress.

By means of the new ligation reaction it is possible to introduce any substituents into oligonucleotides obtained by synthesis. The amidites required for this have been prepared. In this way, multiple labeling is also possible.

Amidates for labeling oligonucleotides

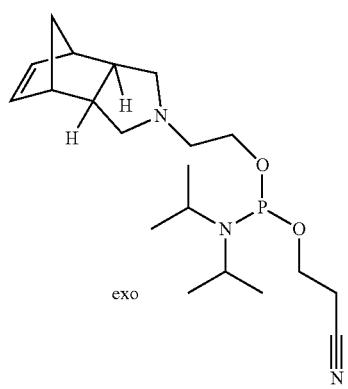

L1871 from M1484
Mass weak

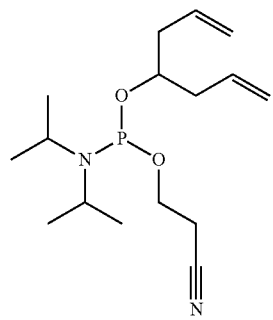

L1874

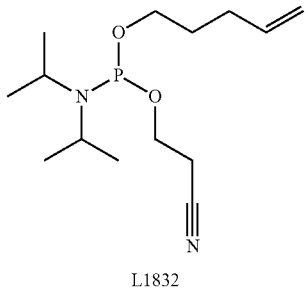

L1832

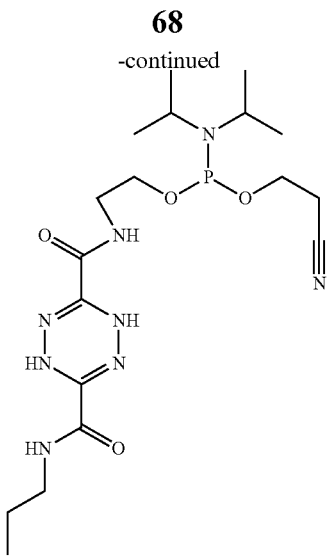

L1866 from F208

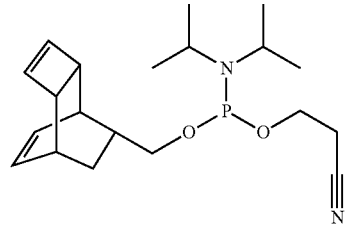 [SMILES: CC(C)N(C(C)C)P(OCCC#N)OCC1CC2C=CC1C1C=CC21]

For this purpose, the introduction of a nucleotide during the synthesis is enough, which carries an alkyl residue with a terminal double bond.

Applications V Photochemistry

The photochemical cyclization of 1,3-dienes to give cyclobutenes proceeds with high quantum yield, a highly reactive inverse dienophile being generated. Thus, the photolithography can be linked with the ligation by the DARinv. The 2+2 cycloaddition only takes place where U.V. light is irradiated, and it is only there that the DARinv can subsequently proceed. Thus, substituted tetrazines and triazines can be added to surfaces here as well.

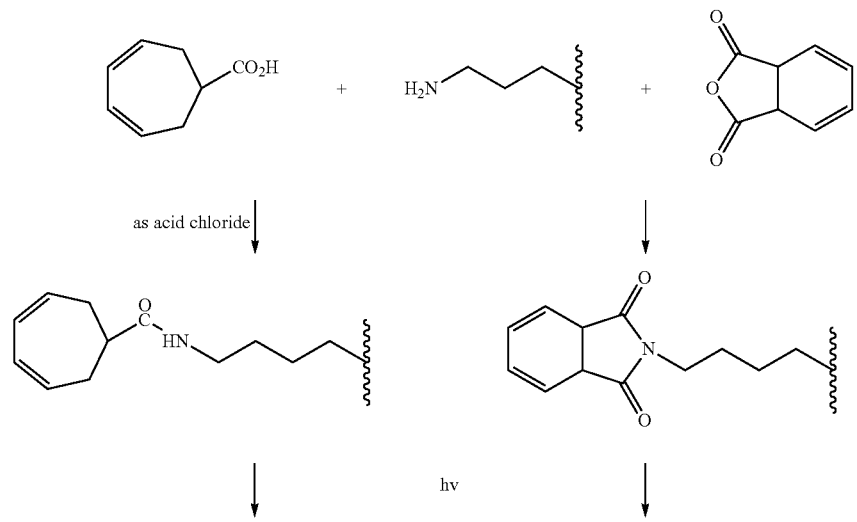

-continued

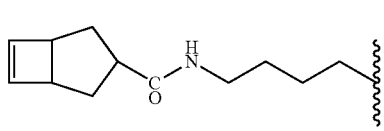
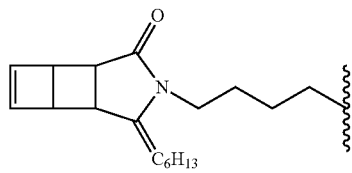

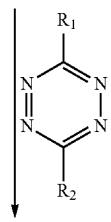 or 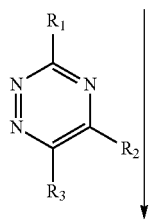

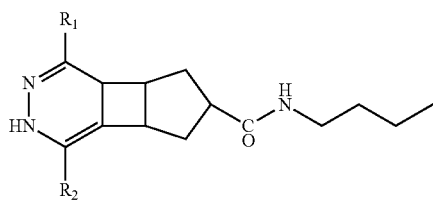
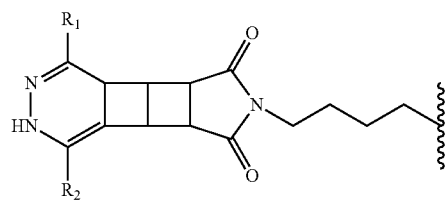

The introduction of the 1,3-dihydro-phthalic acid anhydride-5,6 by reaction with the amino function is also well suited here. The formerly unknown 1,3-cycloheptadiene-6-carboxylic acid is also well suited.

Applications VI Synthesis of Dendrimers and Polymers

The reaction of the COT-MSA anhydride is rapid and clear so that dendritic structures can be synthesized by reactions with polyamines which then can further be modified by reaction with any dienes using the DARinv. The here illustrated compounds are shown and characterized. The triple DARinv can be carried out without any problems. The amines forming after the reduction of the carbonyl groups permit the introduction of two different molecules per bicycle since the four-membered ring and the six-membered ring have markedly differing dienophile activities. However, other polyfunctional molecules, such as inositol, can also readily be provided with allyl groups and thus be used as a template for dendritic structures. These compounds also include the chitosane.

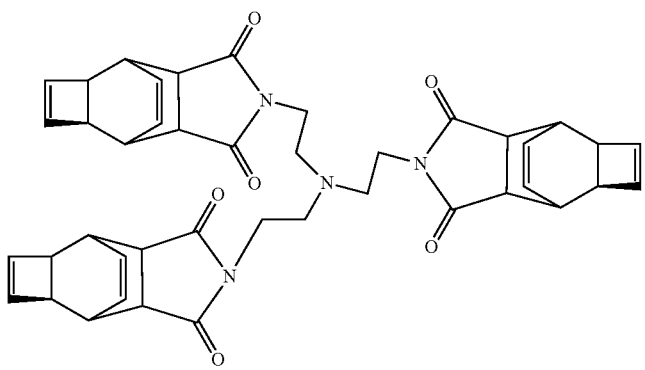

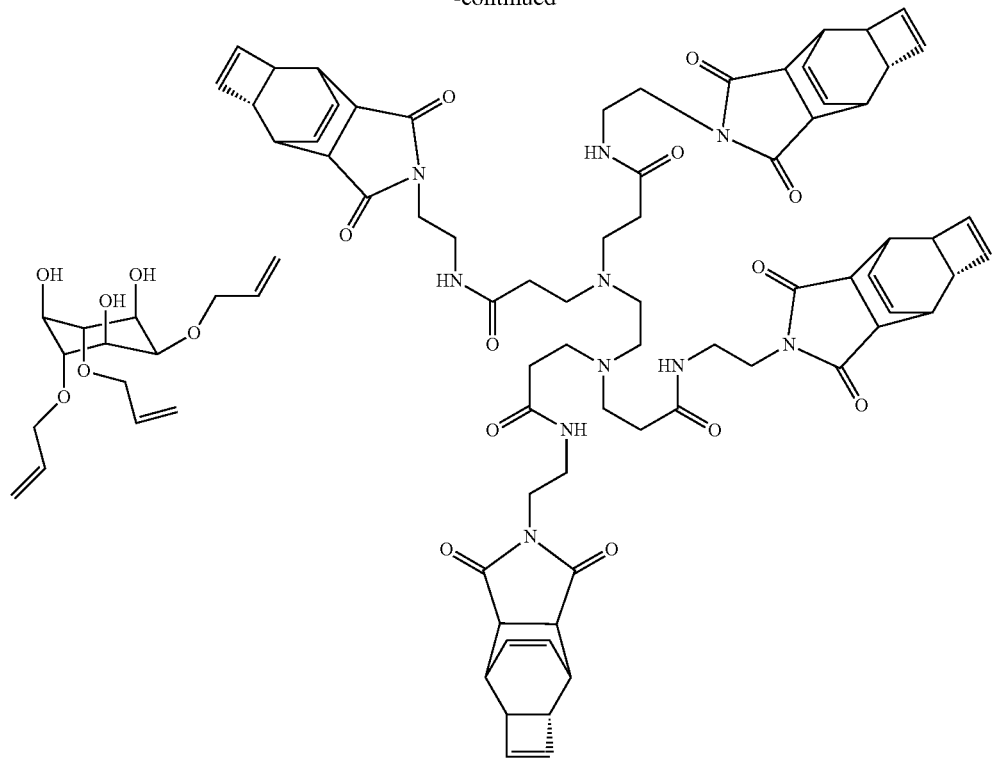

By means of such a technology it is possible to combine e.g. peptides or saccharides for use as therapeutic agents, diagnostic agents or also to study the interaction of peptides or saccharides among one another or with other biomolecules. The dihydrotetrazine dicarboxylic acid can also be incorporated into polyamides during the condensation and be modified after the oxidation to give tetrazine by the DARinv. The diaryl tetrazine dicarboxylic acids are also suited for the incorporation into polyamides of nylon/perlon type. When tetrazines having differing diene reactivity are incorporated in statistical distribution, they can selectively be modified in different ways. Oligomeric tetrazines or mixed oligomeric tetrazines/triazines can be produced with the building blocks mentioned above already and then be selectively modified by the DARinv. The corresponding polymers are conceivable here as well.

Polymeric tetrazines

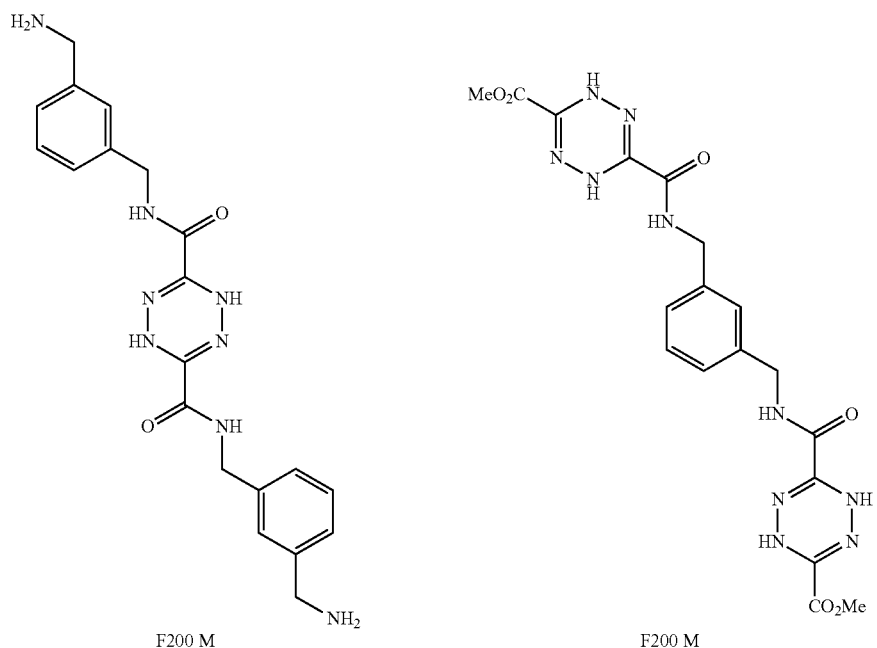

F200 M       F200 M

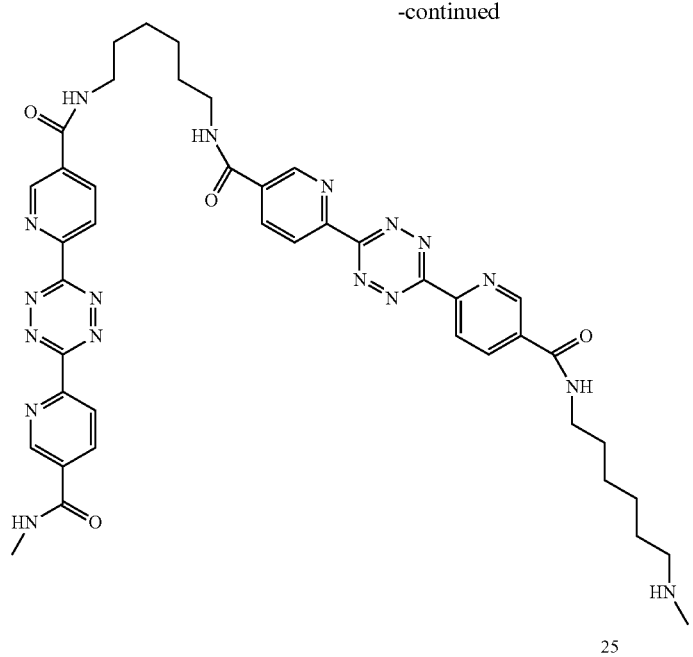

25

Applications VII Quantum Dots

Quantum dots are understood to mean nanoparticles which are composed of compounds such as CdS or CdSe and have special optical properties. Excited by lasers they fluoresce very strongly as a function of their size and therefore are more and more widely used in the diagnostic field especially since they enable the detection of individual molecules. However, a precondition for this is their doping with functional groups, which proceeds via SH groups and permits a subsequent interaction with the molecules to be detected. Gold nanoparticles are considered for electron microscopic investigations of biomolecules on account of their special properties. The anchorage of molecules on the surface is also accomplished here via SH groups. The new ligation technique can also be used by the DARinv. To this end, SH group-containing triazines and tetrazines were produced, initially the disulfides having been produced and then the mercapto compound was prepared therefrom by reduction with dithiothreitol. SH group-containing dienophiles of the norbornene type can also be produced quite analogously. The disulfides as such can also be anchored to gold surfaces.

Thus, both the dienes (tetrazines, triazines and diazines) and the dienophiles can be attached via the disulfide group to the surface of the quantum dots or other metals and are thus accessible to the DARinv. For example, antibodies, saccharides or therapeutic agents can be anchored on the surface of the quantum dots for diagnostic or therapeutic purposes.

Disulfides for anchorage on surfaces

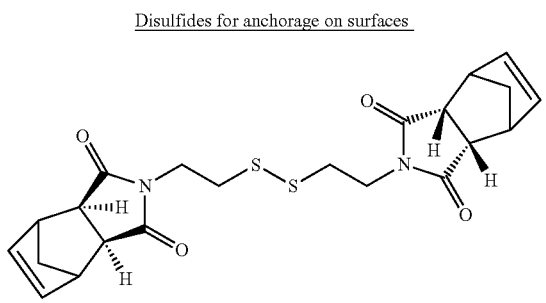

exo
F149 M, NMR

-continued

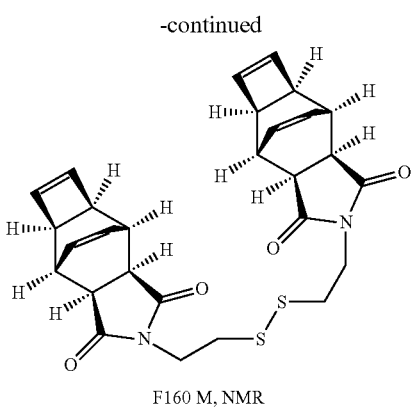

F160 M, NMR

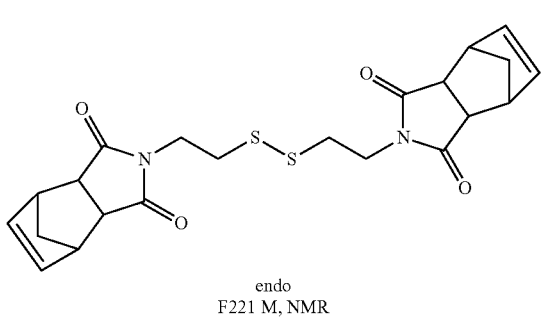

endo
F221 M, NMR

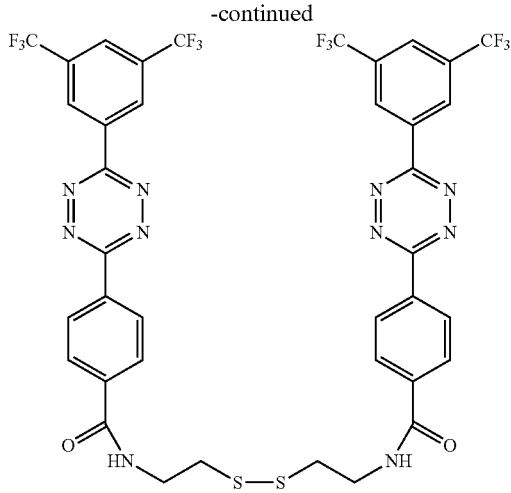

L 1900

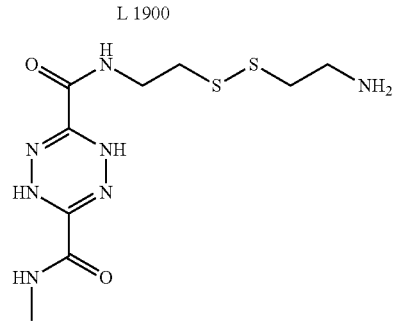

F284 M
from F130

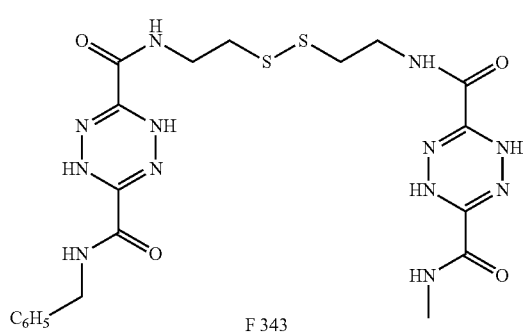

F 343

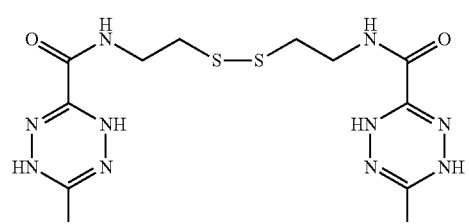

L 1822 M,

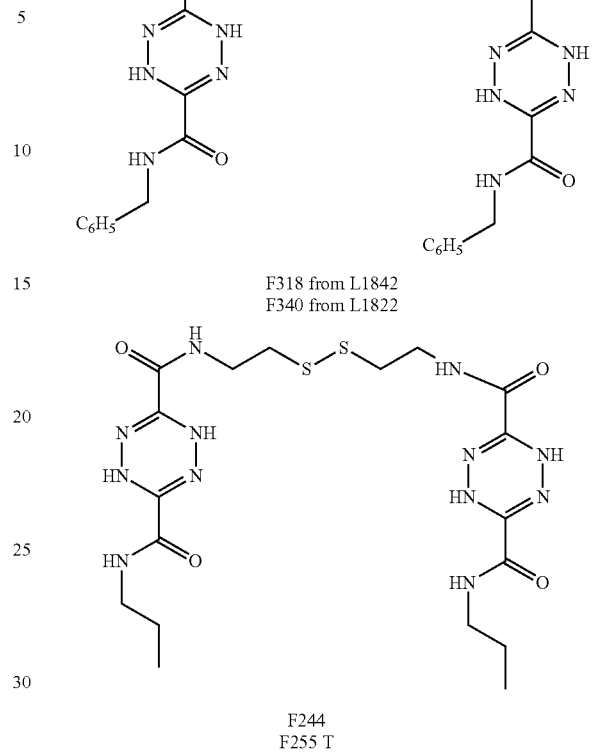

F318 from L1842
F340 from L1822

F244
F255 T

Applications VIII Saccharides

The synthesis of complex saccharide structures requires a sophisticated protecting group strategy. In this connection, the reducing end is often protected by an allyl group or a pentenoyl group.

Oligosaccharides isolated from natural sources can readily be provided with an allyl group or pentenoyl group at the reducing end. Thus, the preconditions for an anchorage of these oligosaccharides to a solid phase or surface by the DARinv are given. The furan saccharide mimetics described in DE-A-100 41 221.1 can also be anchored to either biomolecules or surfaces by means of this DARinv technology. The precondition is the introduction of an allyl ether group or the use of linker molecules as described above.

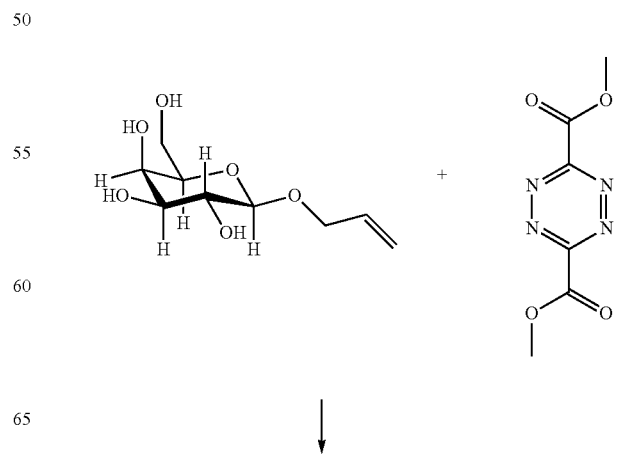

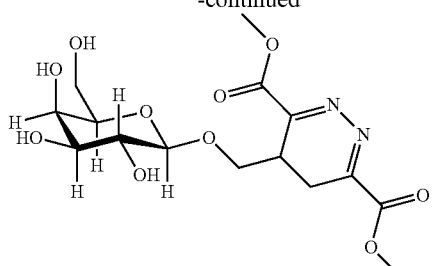

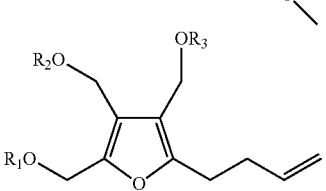

Residues R are saccharides

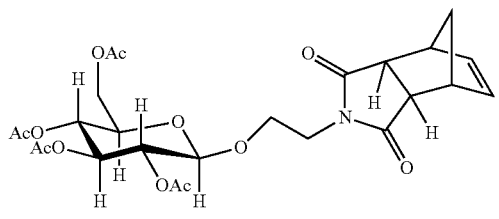

F387

In this way, the compounds described in DE-A-100 41 221.1 can be used in the here described application.

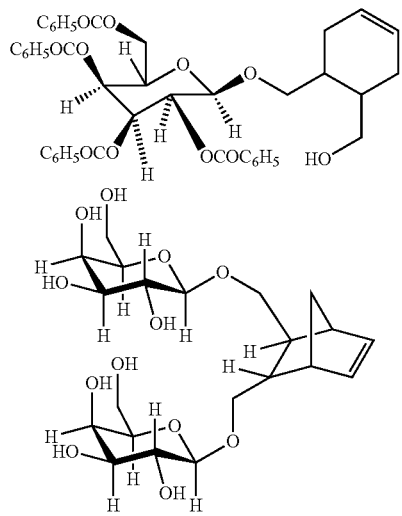

These saccharide mimetics are also suited as inverse dienophiles in the DARinv and therefore can be introduced into any biomolecules.

Applications IX Therapeutics

The side effects of the medicament therapy, in particular tumor therapy, are still clinical daily routine. This is partially due to the fact that it has not yet been possible to introduce therapeutically active substances selectively into the diseased cells. Therefore, there is a demand on simple ligation reactions permitting the linkage of therapeutic agents with molecules enabling a preferred incorporation into the cell. As to the tumor therapy reference is made to EP-A-1 051 421 where the allyl ether of a boron containing tetracarborane is produced which has now proved to be a model dienophile for linkage to peptides or saccharides by means of the DARinv. However, vitamin A, vitamin C, curcumin or other therapeutic agents can be linked by this method to proteins or surfaces where they are released by hydrolysis or enzymatic cleavage. Another example of this application is the temozolomide used for the therapy of brain tumors, which can be coupled to either a tetrazine or a dienophile via its acid function. The coupling to peptides is then possible via the DARinv. Liposomes containing double bonds active in the DARinv can also readily be modified by means of this technology so as to achieve a better targeting or modified pharmacokinetics.

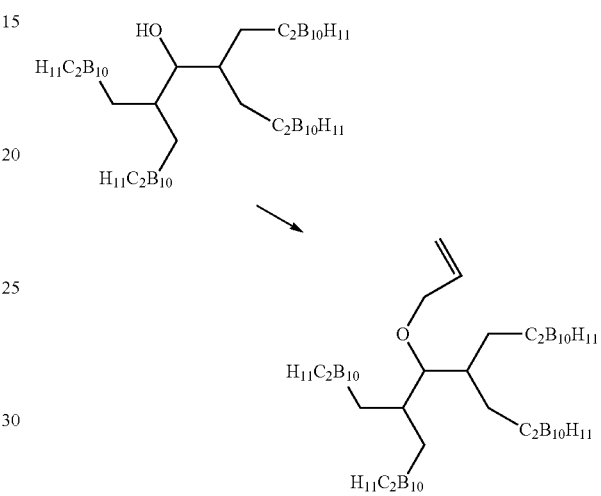

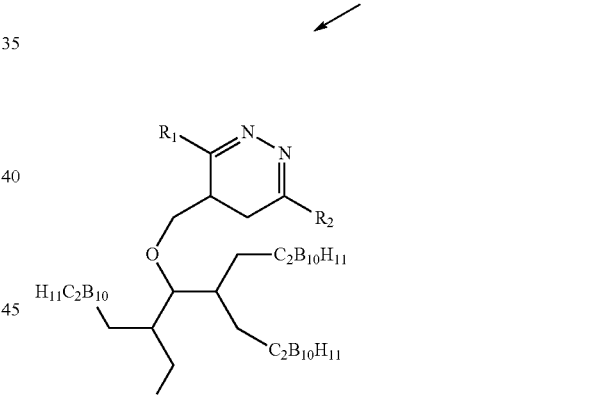

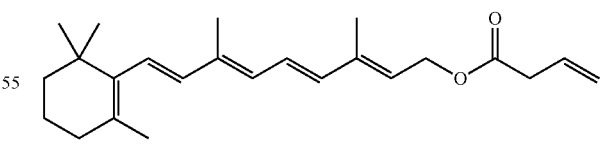

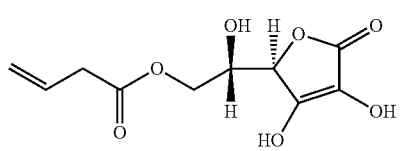

Temozolomid

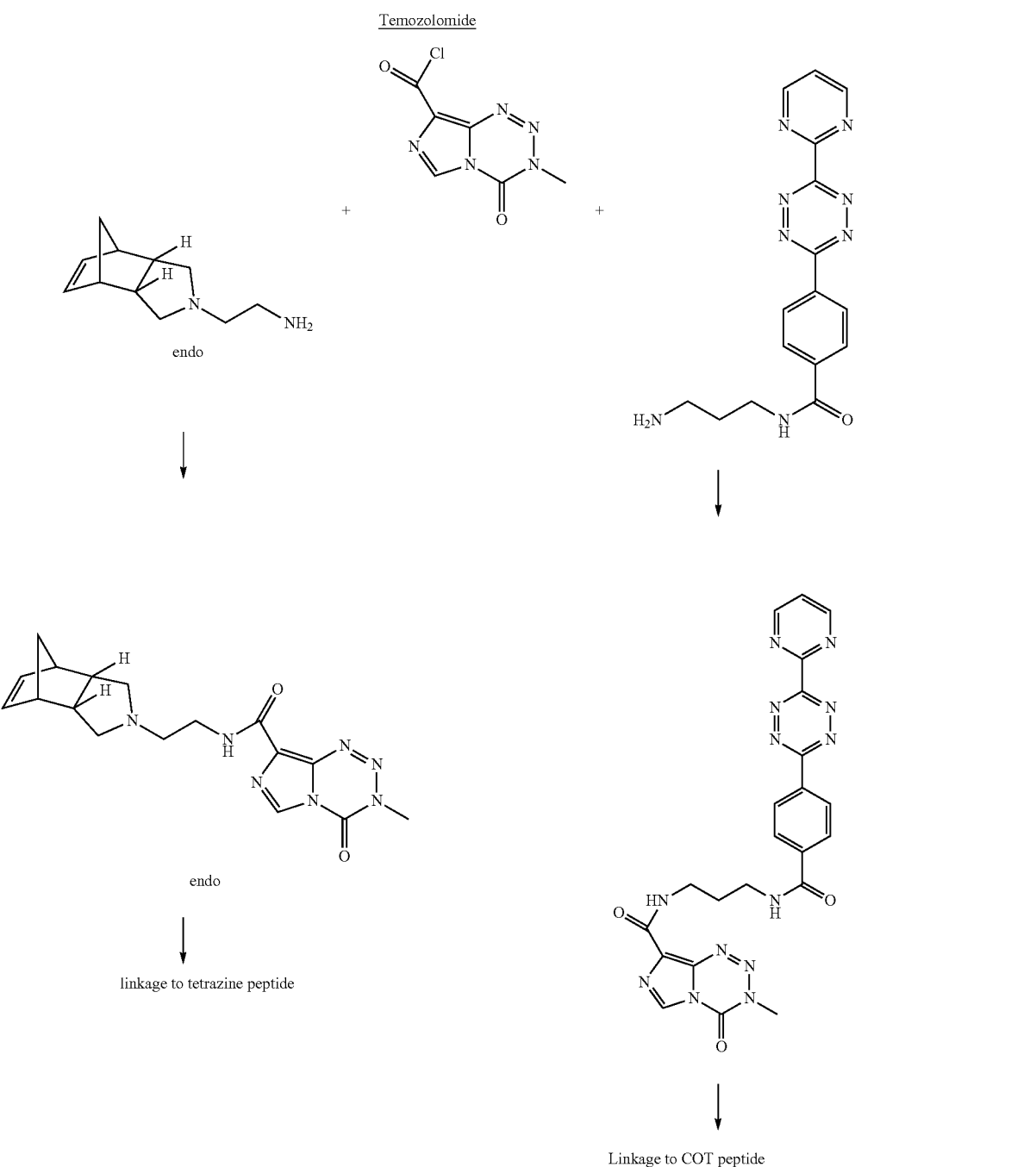

Applications X Oligonucleotides

The ligation reactions known in the literature to date of oligonucleotides by means of the DAR use cyclic dienes and as dienophile maleinimides (Tona R. and Häner Robert, 2005, Bioconjugate Chem 16, 837-842; Hill K. W. et al. 2001, JOC, 66, 5352-5358). However, the reaction rate in these systems is not very high and is up to 7 days or high excesses of reagents have to be used. Here, the DARinv offers itself as the better, because more efficient, ligation reaction. To this end, the two amidites were produced to introduce an allyl or a pentenyl group at the 5' end at the end of the oligo synthesis, which is active in the DARinv as a dienophile.

Linker systems from dienophiles I

Cyclopentadiene and p-benzoquinone

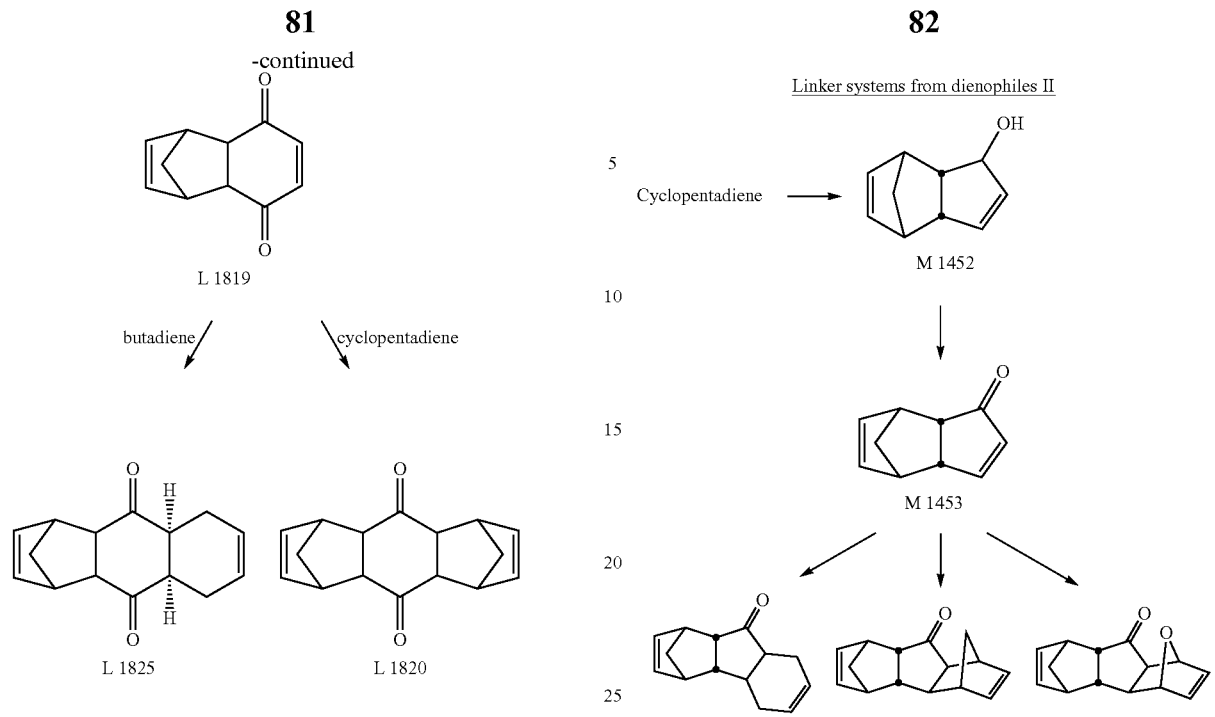

Both systems are suited for the successive linkage of molecules which carry either the same dienophile such as L 1820 or different dienophiles such as L 1825. This linkage type is also simultaneously suited for anchorage to a solid phase by reaction with the carbonyl group(s).

The ketone dicyclopentadienone is an orthogonal dienophile which is accessible to both ordinary DAR and DARinv. However, it can also be converted into a doubly inverse dienophile by reaction with butadiene (see above).

Along with these linkers from dienophiles, linkers from dienes which simultaneously allow a DAR and a DARinv, are also accessible. The combination of tetrazine or triazine with a dienophile, e.g. a maleinimide, is also possible for the classical DAR. The structures are listed below.

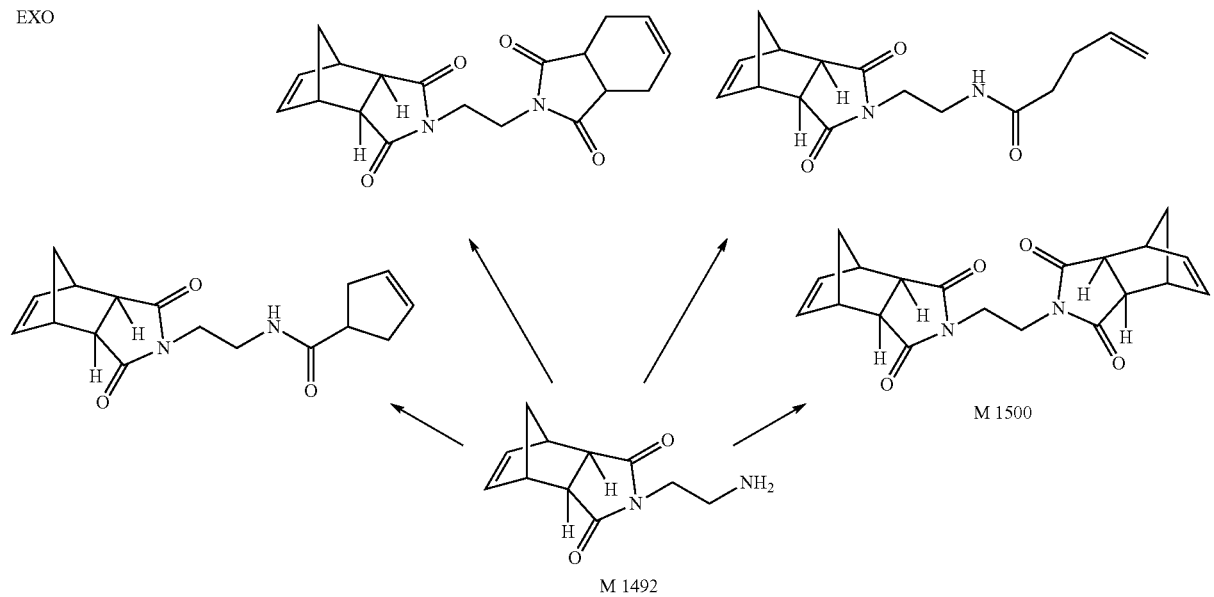

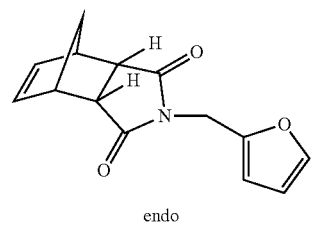
ENDO

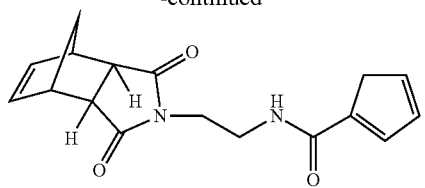
endo

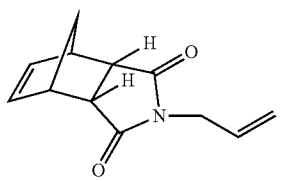

It is shown below that a DARinv can proceed simultaneously with a classical DAR When both dienophiles are present, a rapid DARinv initially takes place which is followed by a slower classical DAR. The products are characterized.

DAR and DARinv simultaneously

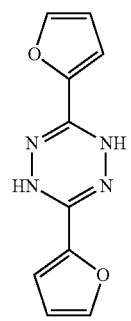

L1692

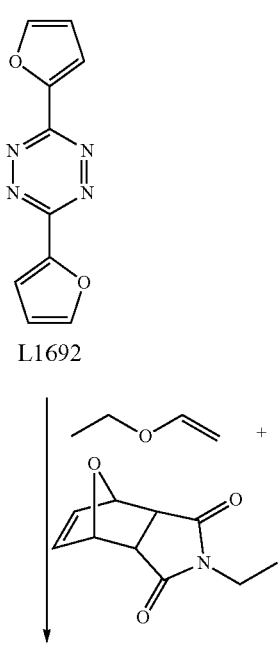

-continued

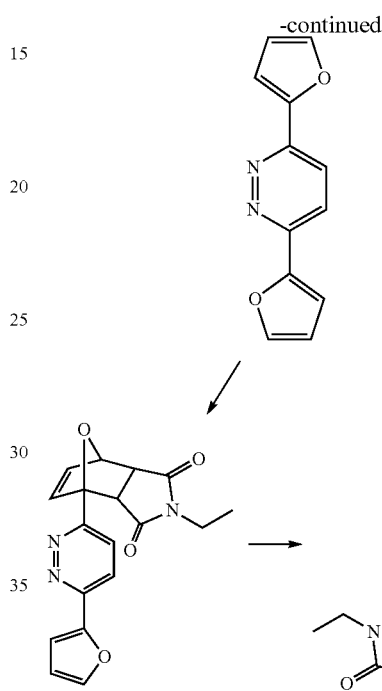

Applications XI Substance libraries

Using the above described new tetrazines, triazine and diazines as dienes in the DARinv novel substance libraries for search for new active substances can be established with dienophiles, e.g. enamines, enol ethers, etc. As described, the diamides per se are accessible by successive reactions with various amines and subsequent oxidation in large number. This reaction sequence can be automated. For the development of the therapeutic agents, sufficient water solubility is an important precondition. A possible approach for the improvement of the water solubility and thus the oral availability is the covalent linkage of active substances with saccharides thereby forming conjugates. By means of the approach according to the invention it is possible to consider the problem of a sufficient water solubility by means of a combinatory approach from the very beginning using suitable amine building blocks in the DARinv. This also offers the advantage that these building blocks become part of the active substance on the basis of saccharides and their derivatives and thus can contribute to the strengthening of the binding of the active substance to its target. These novel structures have to be referred to as peptide mimetics as regards both their synthesis and their structure. The tetrazine-3,6-dicarboxylic acid ester and thus also its diamides and the further derivatives are derived from glycine.

Libraries

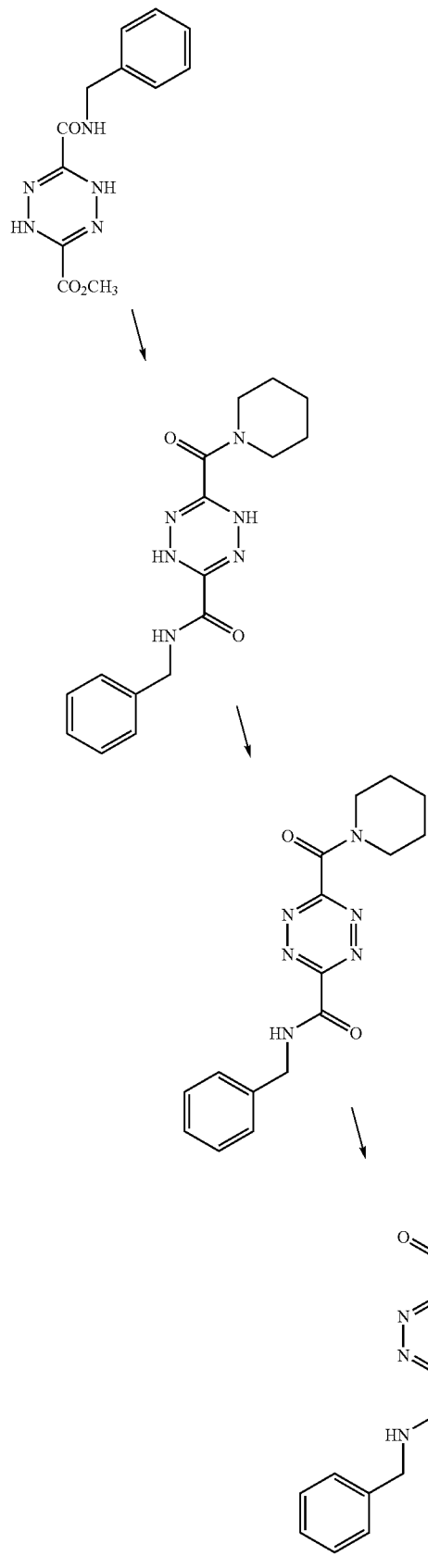

The invention is further described by means of the examples.

EXAMPLES

Example 1

Synthesis of

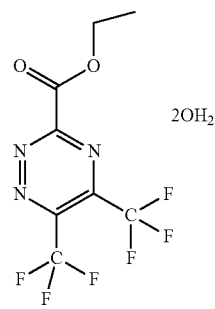 [SMILES: CCOC(=O)c1nnc(C(F)(F)F)c(C(F)(F)F)n1]

5,6-bis-trifluoromethyl-1,2,4-triazine-3-carboxylic acid ethyl ester 5 grams (25.7 mmol) hexafluorobutene were dissolved in 100 ml DMF in argon, discharged to a round-bottom flask having a volume of 500 ml and the oxalamide hydrazone in 10 ml DMF was slowly added drop-wise by cooling at 0° C. (exothermic reaction!). Having terminated the addition, the batch was further stirred at room temperature over night. For processing, the DMF was drawn off at the high vacuum at 50° C. and the remaining residue was taken up in acetic ester and washed with dilute hydrochloric acid and water and dried on sodium sulphate. Having evaporated the acetic ester, recrystallization was carried out from diisopropyl ether. The methyl ester could also be obtained according to the same instruction. Both compounds are obtained as dihydrates, a molecule of water being readily released so that the monohydrate can also be obtained in crystalline form. Mass spectrum and 1H-NMR prove the structures.

In similar way, the following triazenes could also be obtained

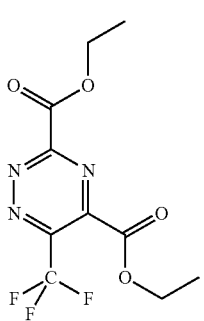 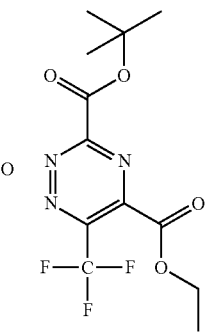

-continued

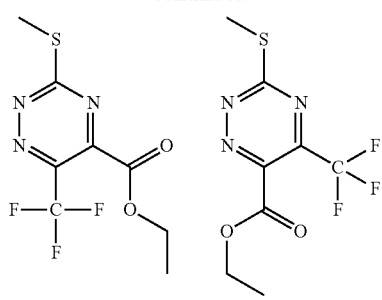

Example 2

Synthesis of

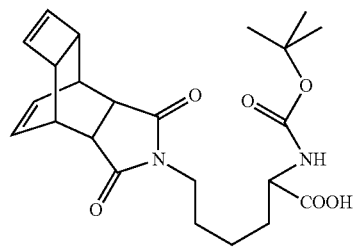 [SMILES: CC(C)(C)OC(=O)NC(CCCCN1C(=O)C2C3C=CC(C4C=CC43)C2C1=O)C(=O)O]

10 mmol of the cyclic anhydride obtained from cyclooctatetraene and maleic acid anhydride were refluxed in 50 ml methanol with 10 mmol Boc-lysine for 3 hours. The residue remaining after the evaporation of the solvent could be recrystallized directly. If the crystallization fails, chromatography on silica gel can be used for the purification, chloroform with 1% methanol. The product crystallizes while allowing to stand. Mass spectrum and NMR prove the structure.

The following compounds were prepared and characterized analogously.

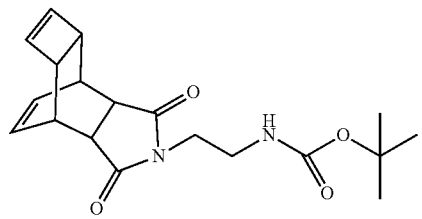

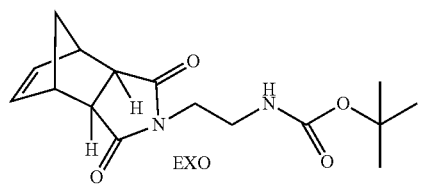

-continued

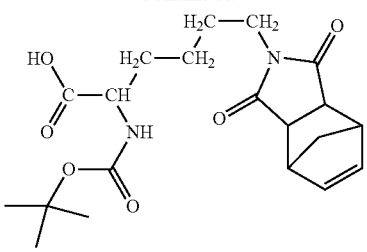

Synthesis of 1 mmol tris-(2-ethylamino)-amine were refluxed in 20 ml methanol with 3 mmol of the tricyclic anhydride for 5 hours. A precipitate forms on cooling, which is sucked off. Yield 80%. The mass spectrum shows the molecule peak at m/e 698 without fragmentation worth mentioning.

The following compound was produced analogously

Synthesis of

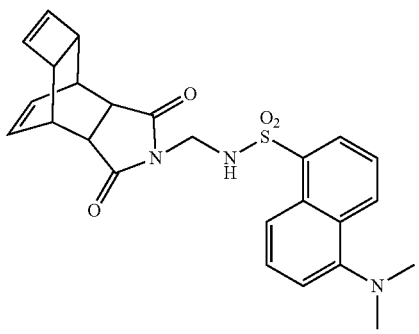

4 mmol (1.36 g) of the amide obtained by reaction of the tricyclic anhydride with N-Boc ethylene diamine of Fp. 135° C., is stirred in a mixture of 10 ml methanol and 20 ml 1 N hydrochloric acid at room temperature over night, the substance being dissolved. Following lyophylization, the hydrochloride is obtained as a white residue in quantitative yield. The mass spectrum shows the molecule peak at 244 for the amine.

0.5 mmol of this hydrochloride was suspended in 10 ml chloroform and then 0.5 mmol dansylchloride were added in solid form. While cooled at 0° C., 0.28 ml triethylamine, corresponding to 2 mmol, was then added drop-wise to 5 ml chloroform. The batch was stirred at room temperature over night. For processing, the organic phase was washed 3 times with 10 ml water each, dried on sodium sulfate and concentrated. For the purpose of purification, chromatography was carried out on silica gel with hexane/acetic acid ethyl ester 2:1. 240 mg solid product was isolated, corresponding to a yield of 50%. The mass spectrum shows the molecule peak at 477 in both the positive and negative modes.

Dienophile Modified Peptides:

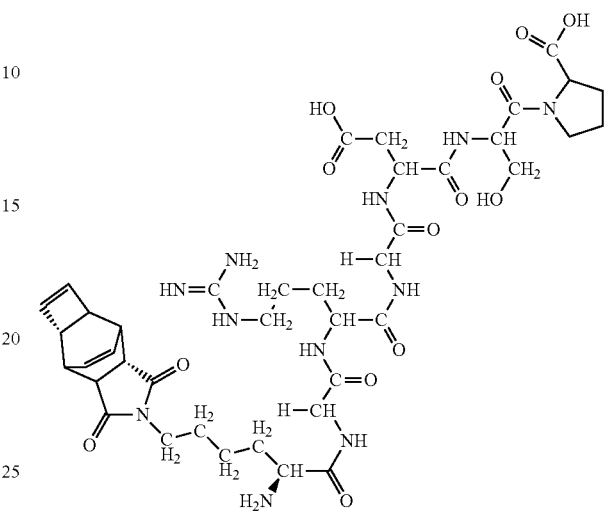

The peptide was produced on a synthesizer, the already described lysine derivative being attached with the tricyclic dienophile in the last stage. This peptide was purified by HPLC and the structure was confirmed by the mass spectrum. Molecule peak at m/e 899.

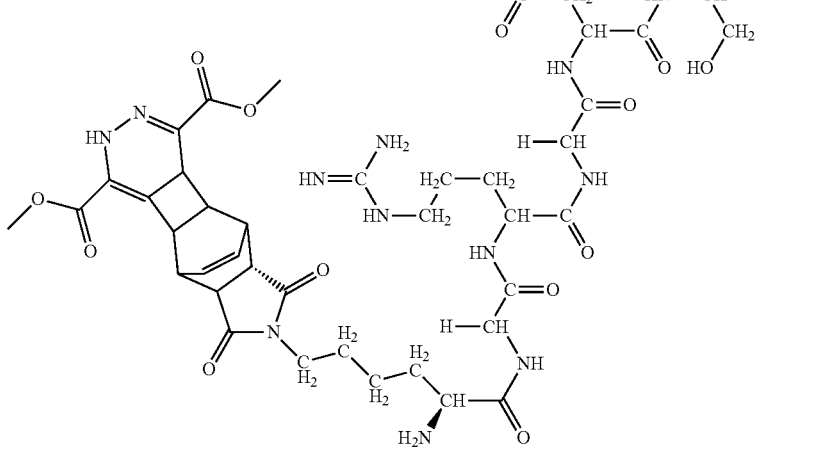

Diels Alder reaction of the above mentioned peptide with the tetrazine-3,6-dicarboxylic acid dimethyl ester:

0.01 mmol (9 mg) of the peptide are dissolved in 0.5 ml DMF and mixed drop-wise with a 0.01 molar solution of tetrazine. After every addition, the red color of tetrazine disappears immediately and tetrazine is added until the red color just disappears. The DMF is evaporated in the high vacuum. The mass of the residue shows the molecule peak at m/e 1096, along with a small amount of the unreacted peptide at m/e 899.

Example 3

Reaction of the dihydrotetrazine-3,6-dicarboxylic acid dimethyl ester with primary amines

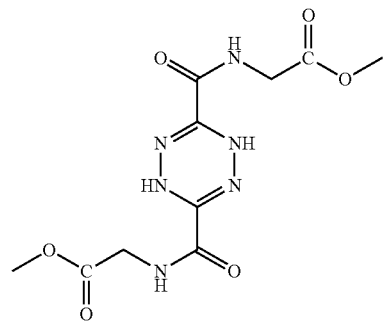

Dihydro-tetrazine-3,6-dicarboxylic acid dimethyl ester 200 mg (1 mmol) are suspended in 5 ml methanol and (2.5 mmol) glycine methyl ester are added drop-wise in 5 ml methanol—prepared from 2.5 mmol glycine methyl ester hydrochloride and 2.5 mmol triethylamine—and stirred at room temperature over night. The reddish solution has turned light yellow and a yellow precipitate has formed. After cooling to −18° C., this precipitate is sucked off and recrystallized from methanol. Yield 55%. Mass spectrum and NMR confirm the structure.

The following compounds were prepared and characterized similarly:

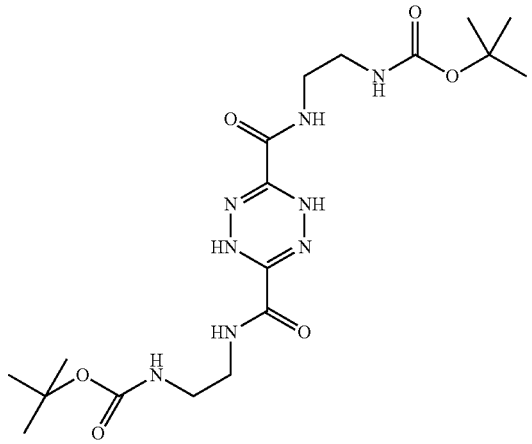

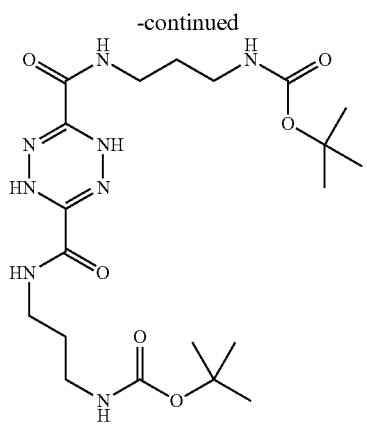

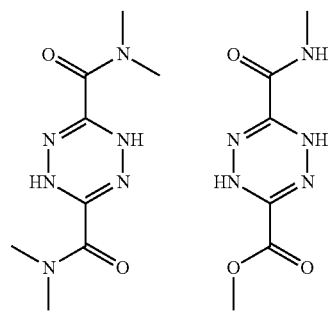

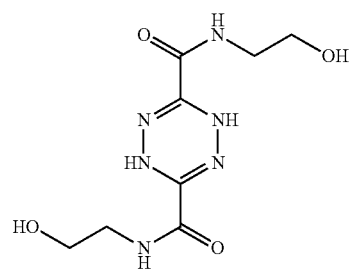

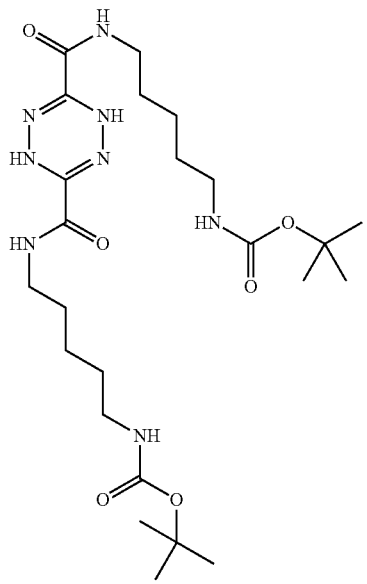

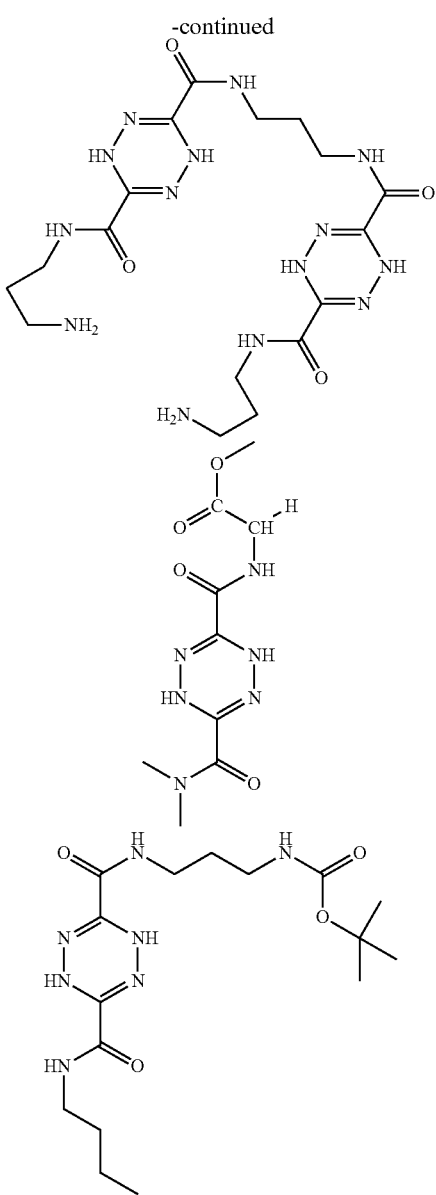

Instructions for the Preparation of Dihydrotetrazine Carboxylic Acid Methyl Ester Monobenzylamide L1842

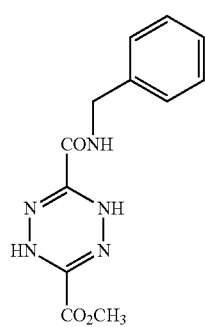

The suspension of dihydrotetrazine dicarboxylic acid dimethyl ester (5 mmol) in 30 ml methanol is heated to 50° C. and the benzylamine (5.5 mmol) in 10 ml methanol is added drop-wise in the course of 2 hours at this temperature. Subsequent stirring is effected for another 2 hours at this temperature followed by cooling to −20° C. over night. In this connection, the monoamide precipitates accompanied by some diamide. In the subsequent recrystallization from methanol, only the monoamide is dissolved and crystallizes as yellow flakes. The yield is between 50 and 80%.

Oxidation of the Dihydrotetrazine into Tetrazine

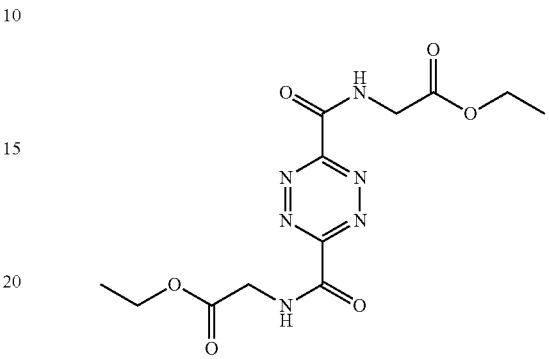

1 mmol (342 mg) of the dihydrotetrazine is dissolved in 10 ml chloroform and mixed with a small excess of isoamylnitrite. The solution adopts an intense red color and the chloroform is withdrawn on the rotary evaporator and the red residue is recrystallized from acetone. Mass spectrum and NMR confirm the structure of tetrazine.

Example 4

Reaction of dihydrotetrazine-3,6-dicarboxylic acid dimethyl ester with glycine methylester at a ratio of 1:1

Dihydrotetrazine-3,6-dicarboxylic acid dimethyl ester 200 mg (1 mmol) is suspended in 10 ml methanol and added at 0° C. to 1 mmol glycine methyl ester as hydrochloride in solid form. Then, 1 mmol triethylamine in 10 ml methanol is slowly added drop-wise. Stirring is carried out at this temperature for another 3 hours, then, cooling is stopped and the solution is heated to room temperature while stirring. The color of the solution is only light red and a yellow precipitate has formed. It is sucked off after cooling to −20° C., washed with cold methanol and with ether and dried. For further purification, recrystallization from methanol is carried out. Mass spectrum and 1H-NMR clearly prove the structure.

The following compounds were produced analogously

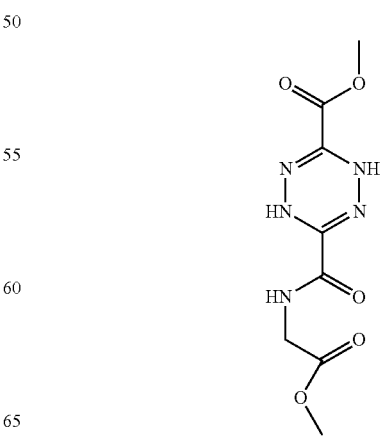

Example 5

Instructions for the preparation of the aza-diaryl tetrazine monocarboxylic acids. E.g. L1892

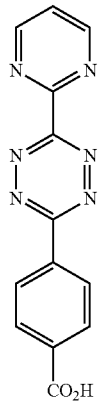

10 mmol of the corresponding nitrites are heated to boiling together with 5 times the excess in ethanol for 4 hours. After cooling, the precipitate formed is sucked off and then boiled out using acetone. In this connection, the dihydrotetrazines dissolve without carboxyl group. The remaining residue is then oxidized with nitrite in glacial acetic acid and the precipitated pink tetrazine mixture is filtrated off. While boiling in DMF, the corresponding monocarboxylic acid is dissolved, the dicarboxylic acids remain as a residue. The monocarboxylic acids accumulate in sufficiently pure form for the further syntheses.

Reactions of dienes and dienophiles for the DAR with inverse electron requirement

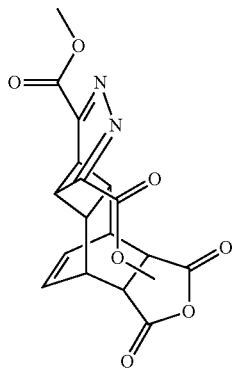

Reaction of the tricyclic anhydride with tetrazine-3,6-dicarboxylic acid dimethyl ester:

To a suspension of 1 mmol (198 mg) of tetrazine-3,6-dicarboxylic acid dimethyl ester in 5 ml tetrahydrofuran, the solution of the tricyclic anhydride in 5 ml of the same solvent was slowly added drop-wise while cooling. While generating nitrogen, a clear red solution formed whose color turned yellow with the last drop of the anhydride added. Concentration was carried out and the remaining residue was recrystallized from acetic acid ethyl ester. Yield is quantitative, Fp. 165° C. The mass spectrum shows the molecule peak of the anhydride at m/e 372.

Analysis of the Diels Alder Reaction with Inverse Electron Requirement on the Solid Phase:

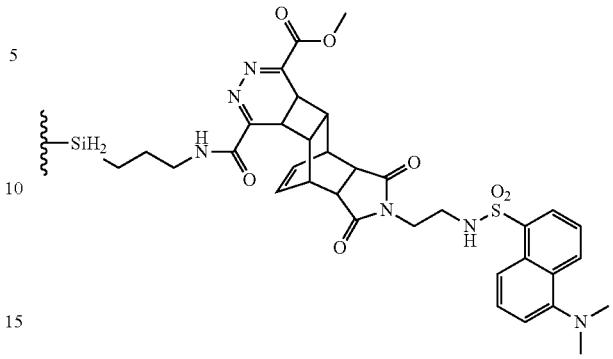

First, 1 g amino-functionalized silica gel (according to the manufacturer's instructions 1 mmol amino groups per gram silica gel) was suspended in 10 ml methanol by shaking, 2 mmol of the dihydrotetrazine-3,6-dicarboxylic acid ester were added and shaken in the closed vessel at 60° C. for 5 hours. Then, it was sucked off, washed several times with methanol and ether and dried. 900 mg silica gel were obtained. The calculation of the C/N ratio served for proving an about 70% occupation by elemental analysis. Oxidation with isoamylnitrite.

The resulting silica gel was suspended in acetic acid ester and shaken with 5 times the excess on isoamylnitrite at room temperature for 5 hours. Filtration was carried out, followed by several wash steps with acetic ester and ether and drying. The silica gel then had adopted a slightly pink color. The elemental analysis only yielded minor changes in the C/N ratio.

The Diels Alder reaction was carried out with the tricyclic anhydride used already several times. For this purpose, 100 mg of the silica gel which loaded with tetrazine was suspended in acetic acid and shaken with 0.3 mmol of the anhydride at room temperature for 2 hours. Filtration was carried out again, followed by 5 wash steps with acetic ester and drying. The C/N ratio of the elemental analysis confirmed the original determined loading of silica gel with dihydrotetrazine with about 70%.

Another Diels Alder reaction was carried out with the dansyl derivative whose synthesis has already been described in connection with the dienophiles. For this purpose, 50 mg of the silica gel which was loaded with tetrazine were suspended in acetic ester and reacted with 0.05 mmol of the dansyl tricycle for 1 hour, sucked off, washed 10 times and dried. The resulting silica gel showed a strong green fluorescence under U.V. light. For the purpose of control, the dihydrotetrazine-loaded silica gel was reacted in the same way, no fluorescence being observed on the silica gel.

Anchorage of the Tricycle as Dienophile on the Solid Phase:

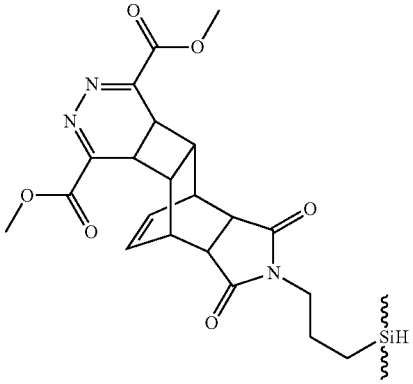

Amino-functionalized silica gel (1 g) was suspended in 10 ml ethanol, 2 mmol (400 mg) of the tricyclic anhydride were added and shaken at 80° C. for 3 hours. The resulting product was sucked off via a frit, washed several times with ethanol and finally with ether and dried. The C/N ratio was determined by elemental analysis and yielded an occupation extent of 70% of the existing amino groups.

100 mg of the functionalized silica gel was suspended in tetrahydrofuran and titrated with a 0.5 molar solution of tetrazine ester in THF. The tetrazine was discolored very rapidly by the proceeding Diels Alder reaction. An original occupation of about 70% could, in turn, be concluded from the tetrazine consumption.

The following products were produced by a Diels Alder reaction with inverse electron requirement, isolated and characterized in a similar way:

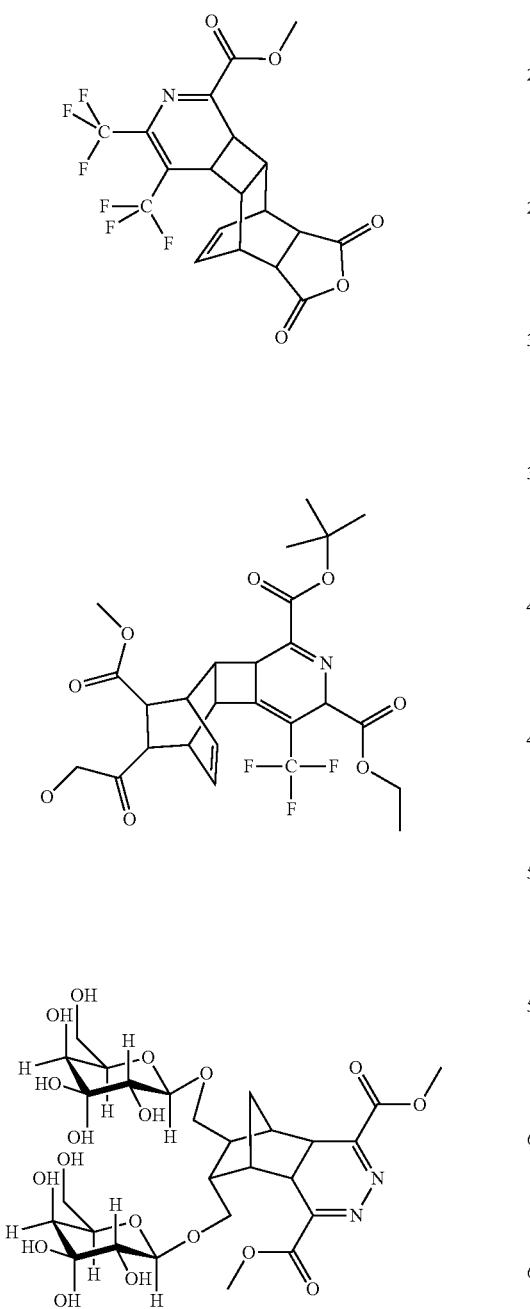

-continued

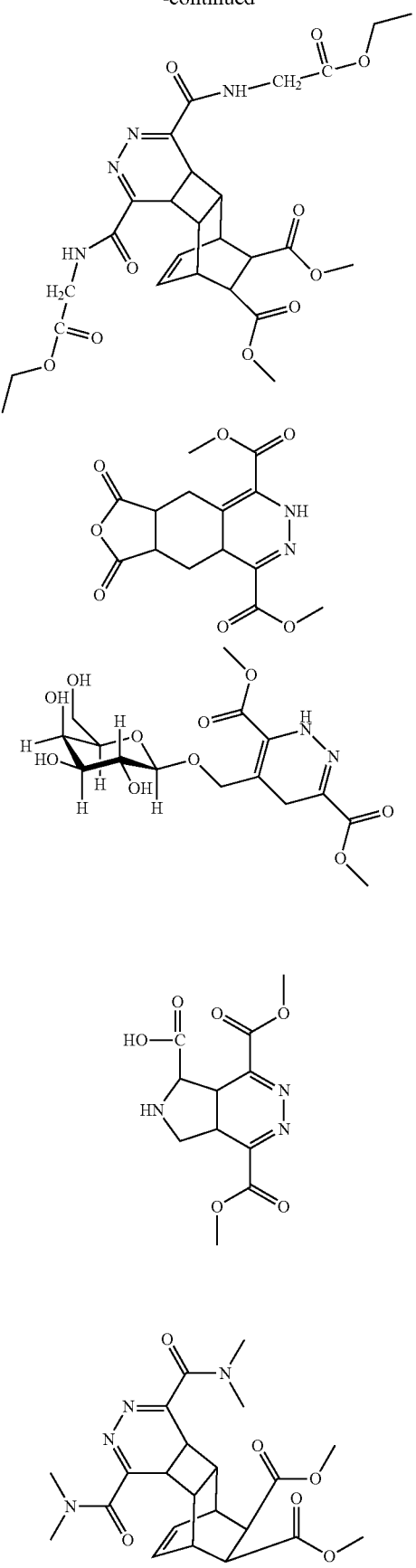

99

-continued

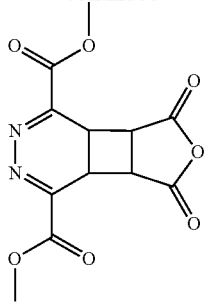

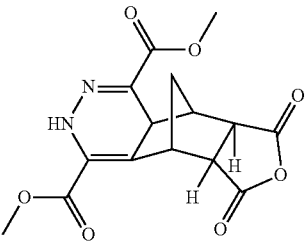

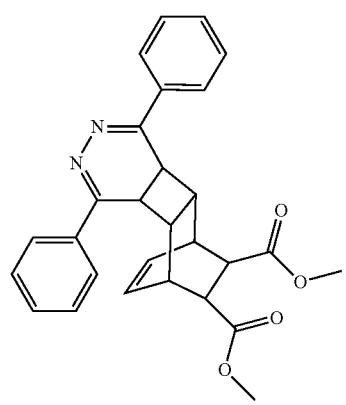

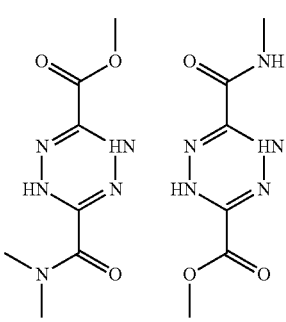

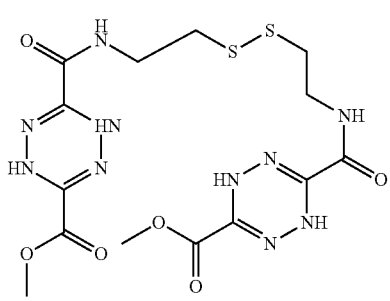

100

-continued

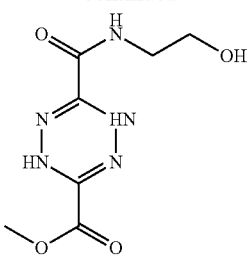

Example 6

Functionalization of the Tetrazines

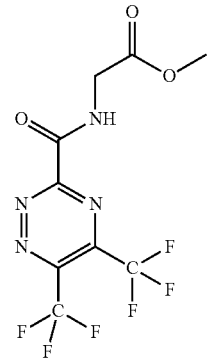 [SMILES: COC(=O)CNC(=O)c1nnc(C(F)(F)F)c(C(F)(F)F)n1]

Reaction of the
5,6-bis-trifluoromethyl-triazine-3-carboxylic acid
methyl ester with glycine methyl ester Glycine methyl ester hydrochloride 3 mmol (375 mg) were suspended in 10 ml dioxan and then 3 mmol Triethylamine (0.42 ml) were added. After 30 minutes, 2 mmol (550 mg) of the bis-trifluoromethyl-triazine-carboxylic acid ester in 10 ml dioxan were added and kept at 80° C. for 5 hours. Concentration was carried out and the residue was chromatographed on silica gel with hexane/acetic ester. 400 mg of the product were obtained. The mass confirms the structure, the compound being obviously present as a monohydrate.

The following compounds were produced and characterized analogously:

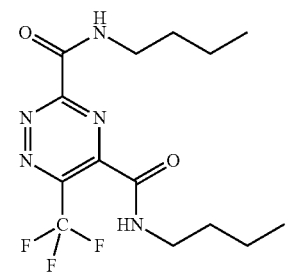

-continued

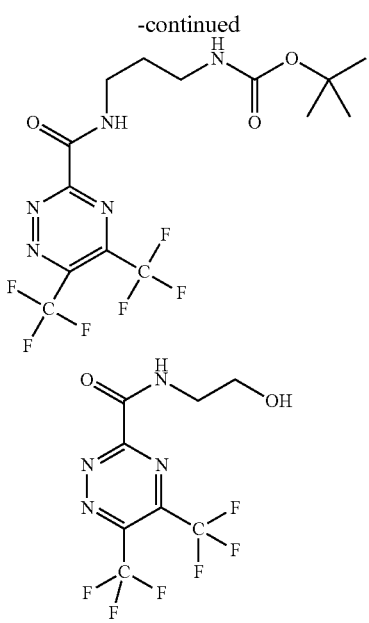

Diels Alder Reaction of the Triazines

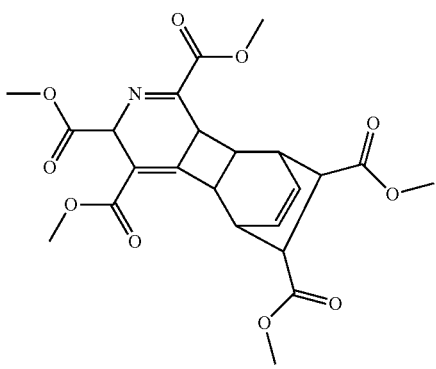

The triazine-tri-carboxylic acid methyl ester 1 mmol (255 mg) was dissolved in 2 ml THF and mixed drop-wise with a solution of 1 mmol (248 mg) of the tricyclic dicarboxylic acid dimethyl ester in 1 ml THF. The generation of nitrogen is observed and the color turns lighter. Concentration is carried out at room temperature after 2 hours and the residue is chromatographed on silica gel with hexane/acetic ester 1:1. 250 mg of the adduct are isolated, corresponding to 50% yield. The mass spectrum confirms the structure, molecule peak at m/e 475.

The invention claimed is:

1. A process for linking two molecules by means of a Diels Alder reaction with inverse electron requirement, comprising the step of:
reacting
(a) a triazine or tetrazine comprising one or more —C(O)NR$_2$ groups as electron-attracting substituents on the ring as a diene component,
wherein R=H, alkyl, aryl, heterocycle, which is optionally substituted with alkyl, OH, SH, halogen, aryl, heterocycle, nitro, carboxyamido or amine group, with
(b) an isolated double bond or triple bond in a heterocarbocyclic ring or an isolated olefinic double bond or triple bond in a linear or branched hydrocarbon chain which optionally contains heteroatoms as a dienophile component,
wherein one or more peptides, saccharides, lipids, oligonucleotides, or nucleic acids are coupled to the diene and/or dienophile component.

2. The process according to claim 1, wherein the dienophile component further contains one or more functionalities selected from the group consisting of alkyl, OH, SH, halogen, aryl, carboxyl, carbonyl, nitro, carboxyamido, keto, sulfoxide, sulfone, sulfonic acid, sulfide, sulfate, phosphoric acid, and amino.

3. The process according to claim 1, wherein the diene is tetrazine-3-trifluoromethyl-6-carboxylic acid amide, triazine tricarboxylic acid monoamide, triazine tricarboxylic acid diamide, or triazine tricarboxylic acid triamide.

4. The process according to claim 1, wherein the dienophile is exo- or endo-norbornene dicarboxylic acid anhydride, cyclobutene dicarboxylic acid anhydride, cyclohexene dicarboxylic acid anhydride, allyl malonic ester, allyl galactose, allyl silsesquioxan, or dicyclopentadienone.

5. The process according to claim 3, wherein the diene is a tetrazine, and the process further comprises oxidizing a corresponding dihydrotetrazine to the tetrazine, before the reacting step.

6. The process according to claim 1, wherein the Diels Alder reaction with inverse electron requirement is carried out in an alcoholic solution at 20 to 100° C.

7. The process according to claim 1, wherein the diene component further contains a electron-attracting substituent selected from the group consisting of:
COOR,
CX$_3$, where X=halogen,
halogen,
CN,
SO$_2$—R or SO$_3$—R,
PR$_2$, and
heterocyclic rings having 1, 2 or 3 N, O or S atoms with a ring size of 5 or 6 ring members, which are substituted with at least one carboxyl, sulfonic acid or phosphone group;
wherein R=H, alkyl, aryl, heterocycle, which is optionally substituted, with alkyl, OH, SH, halogen, aryl, heterocycle, nitro, carboxyamido or amine group.

8. The process according to claim 1, wherein the dienophile component is an isolated double bond or triple bond in a heterocarbocyclic ring.

9. The process according to claim 1, wherein the dienophile component is an isolated olefinic double bond or triple bond in a linear or branched hydrocarbon chain.

* * * * *